(12) United States Patent
Hosono et al.

(10) Patent No.: US 11,639,327 B2
(45) Date of Patent: *May 2, 2023

(54) POLYMERIZABLE COMPOUND, AND LIQUID CRYSTAL COMPOSITION AND LIQUID CRYSTAL DISPLAY DEVICE USING THE SAME

(71) Applicant: DIC Corporation, Tokyo (JP)

(72) Inventors: Ayaki Hosono, Saitama (JP); Masanao Hayashi, Saitama (JP); Tetsuo Kusumoto, Saitama (JP)

(73) Assignee: DIC Corporation, Tokyo (JP)

( * ) Notice: Subject to any disclaimer, the term of this patent is extended or adjusted under 35 U.S.C. 154(b) by 156 days.

This patent is subject to a terminal disclaimer.

(21) Appl. No.: 16/770,067

(22) PCT Filed: Dec. 6, 2018

(86) PCT No.: PCT/JP2018/044883
§ 371 (c)(1),
(2) Date: Jun. 4, 2020

(87) PCT Pub. No.: WO2019/124092
PCT Pub. Date: Jun. 27, 2019

(65) Prior Publication Data
US 2021/0214299 A1    Jul. 15, 2021

(30) Foreign Application Priority Data

Dec. 21, 2017 (JP) .............................. JP2017-245024

(51) Int. Cl.
| | |
|---|---|
| G02F 1/1333 | (2006.01) |
| C07C 69/54 | (2006.01) |
| G02F 1/1337 | (2006.01) |
| C07D 309/04 | (2006.01) |
| C07D 309/12 | (2006.01) |
| C09K 19/06 | (2006.01) |
| C09K 19/12 | (2006.01) |
| C09K 19/30 | (2006.01) |
| C09K 19/32 | (2006.01) |
| C09K 19/34 | (2006.01) |
| C09K 19/04 | (2006.01) |

(52) U.S. Cl.
CPC ............ *C07C 69/54* (2013.01); *C07D 309/04* (2013.01); *C07D 309/12* (2013.01); *C09K 19/063* (2013.01); *C09K 19/12* (2013.01); *C09K 19/3003* (2013.01); *C09K 19/32* (2013.01); *C09K 19/3402* (2013.01); *G02F 1/133726* (2021.01); *C09K 2019/0448* (2013.01); *C09K 2019/123* (2013.01); *C09K 2019/301* (2013.01); *C09K 2019/3004* (2013.01); *G02F 2202/02* (2013.01)

(58) Field of Classification Search
CPC .. C09K 19/063; C09K 19/12; C09K 19/3003; C09K 19/32; C09K 19/3402; C09K 2019/0448; C09K 2019/123; C09K 2019/301; C09K 2019/3004; C09K 2019/3006; C09K 2019/3009; G02F 1/1333; G02F 1/133726; G02F 2202/02; C07D 309/04; C07D 309/12
See application file for complete search history.

(56) References Cited

U.S. PATENT DOCUMENTS

| | | | | |
|---|---|---|---|---|
| 10,190,050 | B2 * | 1/2019 | Lim .................. | G02F 1/133711 |
| 11,174,217 | B2 * | 11/2021 | Hosono .................. | C07F 7/081 |
| 11,390,811 | B2 * | 7/2022 | Yamamoto ......... | C09K 19/3405 |
| 2017/0210994 | A1 | 7/2017 | Lim et al. | |
| 2020/0308488 | A1 * | 10/2020 | Shimizu ................ | C09K 19/46 |
| 2020/0399539 | A1 * | 12/2020 | Hayashi ................ | C09K 19/56 |
| 2021/0026206 | A1 * | 1/2021 | Kurisawa ............ | C09K 19/3003 |
| 2021/0214299 | A1 * | 7/2021 | Hosono ............. | C09K 19/3066 |

FOREIGN PATENT DOCUMENTS

| | | |
|---|---|---|
| CN | 104321408 | 1/2015 |
| CN | 107108453 | 8/2017 |
| JP | 2014524951 | 9/2014 |
| JP | 2015168826 | 9/2015 |
| WO | 2013054682 | 4/2013 |
| WO | 2017041893 | 3/2017 |
| WO | 2017188001 | 11/2017 |

OTHER PUBLICATIONS

"International Search Report (Form PCT/ISA/210) of PCT/JP2018/044883," dated Mar. 12, 2019, with English translation thereof, pp. 1-5.

* cited by examiner

*Primary Examiner* — Geraldina Visconti
(74) *Attorney, Agent, or Firm* — JCIPRNET

(57) ABSTRACT

The present invention provides a compound represented by formula (i), a liquid crystal composition using the compound, and a liquid crystal display device using the liquid crystal composition. The compound represented by formula (i) has a partial structure $K^{i1}$ represented by any of general formulas (K-1) to (K-17) and further has ring B having at least two P-Sp- groups. Therefore, when used for a liquid crystal composition, the compound adsorbs to substrates sandwiching the liquid crystal composition (liquid crystal layer) and allows liquid crystal molecules to be held such that they are aligned in a vertical direction without a PI layer, and improved alignment stability and low-temperature storage stability can be achieved.

7 Claims, No Drawings

POLYMERIZABLE COMPOUND, AND LIQUID CRYSTAL COMPOSITION AND LIQUID CRYSTAL DISPLAY DEVICE USING THE SAME

CROSS-REFERENCE TO RELATED APPLICATION

This application is a 371 application of the International PCT application serial no. PCT/JP2018/044883, filed on Dec. 6, 2018, which claims the priority benefit of Japan Patent Application No. 2017-245024, filed on Dec. 21, 2017. The entirety of each of the above-mentioned patent applications is hereby incorporated by reference herein and made a part of this specification.

TECHNICAL FIELD

The present invention relates to a polymerizable compound and to a liquid crystal composition and a liquid crystal display device that use polymerizable compound.

BACKGROUND ART

In conventional VA (Vertical Alignment) liquid crystal displays, a polyimide alignment film (PI) layer is disposed on electrodes in order to induce vertical alignment of liquid crystal molecules when no voltage is applied and to obtain horizontal alignment of the liquid crystal molecules when a voltage is applied. However, since the formation of the PI layer requires a very large cost, it has recently been contemplated to use a method that can align liquid crystal molecules without the PI layer.

For example, PTL 1 discloses a liquid crystal medium that is based on a mixture of polar compounds having a negative dielectric anisotropy and contains at least one self-aligning additive. It is stated that the liquid crystal medium is highly suitable for use in a display including no alignment layer. In PTL 1, a specific compound having a hydroxy group is used as the self-aligning additive.

CITATION LIST

Patent Literature

PTL 1: Japanese Unexamined Patent Application Publication (Translation of PCT Application) No. 2014-524951

SUMMARY OF INVENTION

Technical Problem

However, studies conducted by the inventors have revealed that, when the self-aligning additive described in PTL 1 is used, anchoring force for vertically aligning liquid crystal molecules and electrooptical properties such as alignment nonuniformity are still insufficient and that there is room for improvement in the storage stability of a liquid crystal composition containing the self-aligning additive.

Accordingly, it is an object of the invention to provide a polymerizable compound that has a polar group, can provide storage stability when added to a liquid crystal composition, and can align liquid crystal molecules without a PI layer. It is another object of the invention to provide a liquid crystal composition that is excellent in storage stability and allows liquid crystal molecules to be aligned vertically without a PI layer and to provide a liquid crystal display device using the liquid crystal composition.

Solution to Problem

The present invention provides a compound represented by general formula (i):

[Chem. 1]

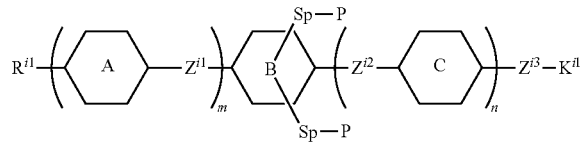

(i)

(wherein
$R^{i1}$ represents a hydrogen atom, P-Sp-, a linear or branched alkyl group having 1 to 30 carbon atoms, or a linear or branched halogenated alkyl group having 1 to 30 carbon atoms, any —$CH_2$— group in the alkyl group or the halogenated alkyl group being optionally replaced by —CH=CH—, —C≡C—, —O—, —NH—, —COO—, —OCO—, or —OCOO—, provided that no —O— groups are adjacent to each other;

ring A and ring C each independently represent a divalent aromatic group, a divalent cyclic aliphatic group, a divalent heterocyclic compound group, a divalent condensed ring, or a divalent condensed polycyclic ring, any hydrogen atom in these ring structures being optionally replaced by $L^{i1}$, $L^{i1}$ representing a halogen atom, a cyano group, a nitro group, P-Sp-, a monovalent organic group having a substituent represented by general formula $K^{i1}$, a linear or branched alkyl group having 1 to 30 carbon atoms, or a linear or branched halogenated alkyl group having 1 to 30 carbon atoms, any —$CH_2$— group in the alkyl group or the halogenated alkyl group being optionally replaced by —CH=CH—, —C≡C—, —O—, —NH—, —COO—, —OCO—, or —OCOO—, provided that no —O— groups are adjacent to each other;

ring B represents a phenylene group or a naphthylene group, ring B having at least two P-Sp- groups;

$Z^{i1}$ and $Z^{i2}$ each independently represent a single bond, —O—, —CH=CH—, —CF=CF—, —C≡C—, —COO—, —OCO—, —OCOO—, —OOCO—, —$CF_2$O—, —$OCF_2$—, —CH=CHCOO—, —OCOCH=CH—, —CH=C($CH_3$)COO—, —OCOC($CH_3$)=CH—, —$CH_2$—CH($CH_3$)COO—, —OCOCH($CH_3$)—$CH_2$—, —$OCH_2CH_2O$—, or an alkylene group having 1 to 10 carbon atoms, one —$CH_2$— group or two or more non-adjacent —$CH_2$— groups in the alkylene group being optionally replaced by —O—, —COO— or —OCO—;

$Z^{i3}$ represents a single bond, —O—, —CH=CH—, —COO—, —OCO—, —OCOO—, —OOCO—, —CH=CHCOO—, —OCOCH=CH—, —CH=C($CH_3$)COO—, —OCOC($CH_3$)=CH—, —$CH_2$—CH($CH_3$)COO—, —OCOCH($CH_3$)—$CH_2$—, or a linear or branched alkylene group having 1 to 20 carbon atoms, one —$CH_2$— group or two or more non-adjacent —$CH_2$— groups in the alkylene group being optionally replaced by —O—, —COO—, or —OCO—; and $K^{i1}$ represents a group represented by any of general formulas (K-1) to (K-17):

[Chem. 2]

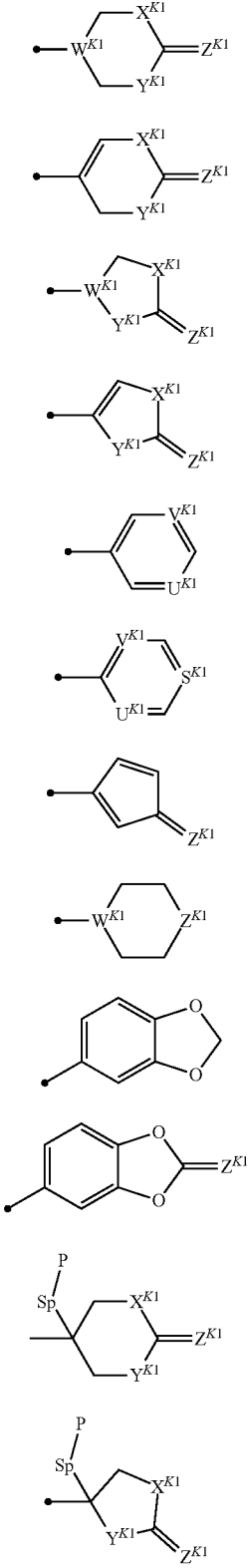

(K-1)
(K-2)
(K-3)
(K-4)
(K-5)
(K-6)
(K-7)
(K-8)
(K-9)
(K-10)
(K-11)
(K-12)

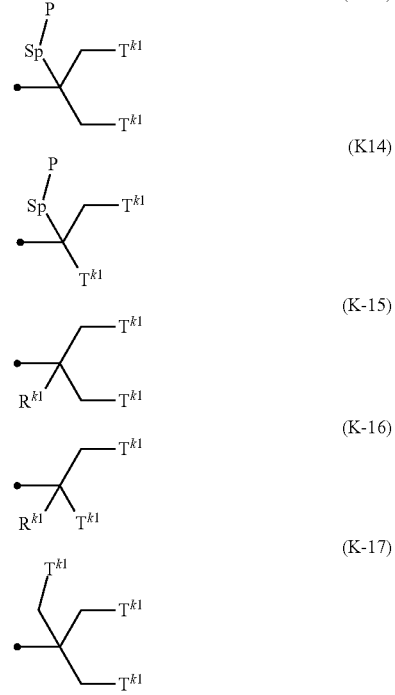

(K-13)
(K14)
(K-15)
(K-16)
(K-17)

wherein $X^{K1}$ and $Y^{K1}$ each independently represent —CH$_2$—, an oxygen atom, or a sulfur atom; $Z^{K1}$ represents an oxygen atom or a sulfur atom; $W^{K1}$, $U^{K1}$, $V^{K1}$, and $S^{K1}$ each independently represent a methine group or a nitrogen atom; $R^{K1}$ represents a hydrogen atom or a linear or branched alkyl group having 1 to 6 carbon atoms; and $T^{K1}$ each independently represent a group represented by any of general formulas (T-1) to (T-6):

[Chem. 3]

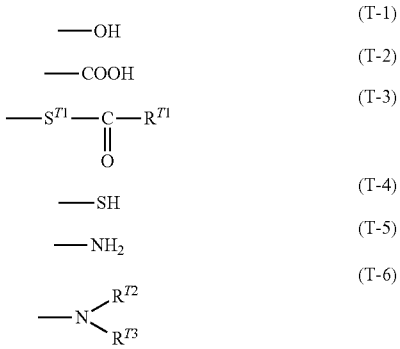

(T-1)
(T-2)
(T-3)
(T-4)
(T-5)
(T-6)

wherein $S^{T1}$ represents a single bond, a linear or branched alkylene group having 1 to 15 carbon atoms, or a linear or branched alkenylene group having 2 to 18 carbon atoms, any —CH$_2$— group in the alkylene group or the alkenylene group being optionally replaced by —O—, —COO—, —C(=O)—, —C(=CH$_2$)—, or —OCO—, provided that no oxygen atoms are directly adjacent to each other; $R^{T1}$ represents an alkyl group having 1 to 5 carbon atoms, any —CH$_2$— group in the alkyl group being optionally replaced by —O—, —COO—, —C(=O)—, —C(=CH$_2$)—, or —OCO—, provided that no oxygen atoms are directly adjacent to each other; and $R^{T2}$ and $R^{T3}$ each independently represent a hydrogen atom or an alkyl group having 1 to 5 carbon atoms, and wherein a plurality of P each represent a polymerizable group; a plurality of Sp each represent a spacer group or a single bond; m represents an integer of 1 to 4; n represents 0 or 1; P may be the same or different; S may be the same or different; when a plurality of A, C, $Z^1$, $Z^2$, and $K^{i1}$ are present, they may be the same or different; and, when $K^{i1}$ represents any of general formulas (K-15), (K-16), and (K-17) and each $T^{k1}$ represents any of (T-1), (T-4), and (T-5), at least one Sp represents a single bond).

The present invention also provides a liquid crystal composition containing one or two or more compounds each having a partial structure represented by general formula (i).

Advantageous Effects of Invention

The present invention can provide a polymerizable compound and a liquid crystal composition that are excellent in storage stability, allow liquid crystal molecules to be aligned vertically without a PI layer, provide a stable tilt angle, and have high reliability and can also provide a liquid crystal display device using the liquid crystal composition.

DESCRIPTION OF EMBODIMENTS

A polymerizable compound in an embodiment is a compound represented by general formula (i).

[Chem. 4]

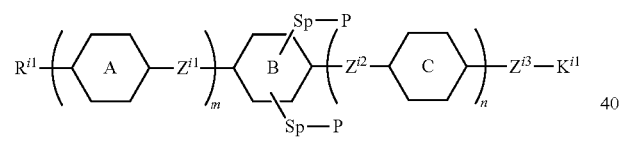

(i)

In general formula (i), $K^{i1}$ represents a group represented by any of general formulas (K-1) to (K-17).

[Chem. 5]

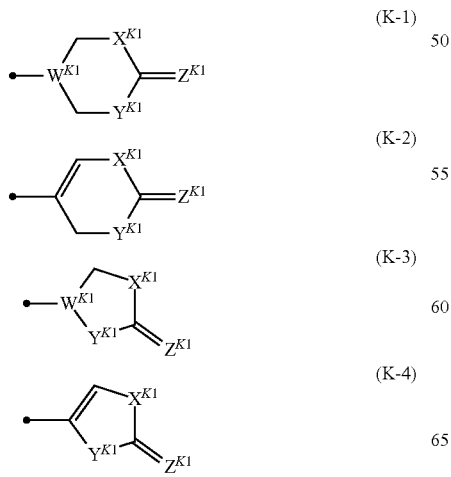

(K-1)

(K-2)

(K-3)

(K-4)

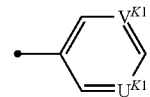

(K-5)

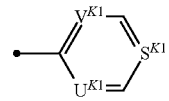

(K-6)

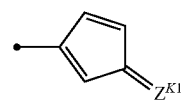

(K-7)

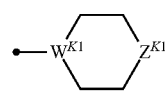

(K-8)

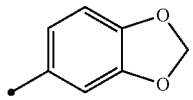

(K-9)

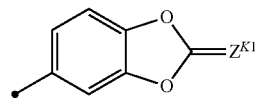

(K-10)

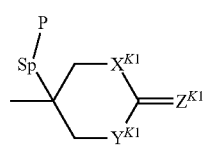

(K-11)

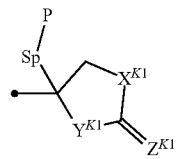

(K-12)

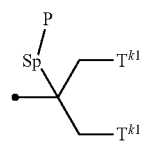

(K-13)

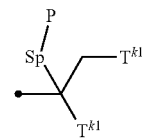

(K14)

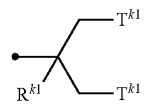

(K-15)

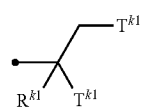

(K-16)

(K-17)

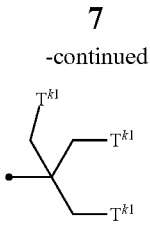

In particular, the compound represented by general formula (i) has a partial structure represented by any of general formulas (K-1) to (K-17). Therefore, when used for a liquid crystal composition, the compound represented by general formula (i) is aligned on substrates sandwiching the liquid crystal composition (liquid crystal layer) and allows liquid crystal molecules to be held such that they are aligned vertically. Therefore, in the liquid crystal composition using the polymerizable compound in the present embodiment, the liquid crystal molecules can be aligned without a PI layer (vertical alignment of the liquid crystal molecules is induced when no voltage is applied, and horizontal alignment of the liquid crystal molecules is obtained when a voltage is applied). As described above, the compound represented by general formula (i) is suitably used for assisting vertical alignment of liquid crystal molecules in a liquid crystal composition.

Moreover, the present inventors have found that, since the polymerizable compound represented by general formula (i) in the present embodiment has the partial structure represented by any of general formulas (K-1) to (K-17) and ring B having at least two P-Sp- groups, not only liquid crystal molecules can be aligned, but also improved alignment stability and low-temperature storage stability can be achieved.

From the above point of view, it is only necessary that the polymerizable compound in the present embodiment include the partial structure represented by any of general formulas (K-1) to (K-17) at a terminal of the molecule, preferably a terminal of the main chain of the molecule and include a structure which includes ring B and to which the partial structure represented by any of general formulas (K-1) to (K-17) is bonded. No particular limitation is imposed on the rest of the chemical structure, so long as the functions of the liquid crystal composition are not impeded.

In formula (i), ring B represents a phenylene group or a naphthylene group. Since ring B has at least two P-Sp- groups, vertical alignment is not disturbed even when a polymerization reaction is initiated by UV irradiation. Therefore, a stiff polymer layer can be formed, and low-temperature storage stability can be improved. Preferably, in general formula (i), P each independently represent a substituent selected from the group consisting of general formula (P-1) to general formula (P-14) below. From the viewpoint of ease of handling and reactivity, formulas (P-1) and (P-2) are more preferable.

[Chem. 6]

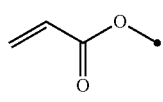
(P-1)

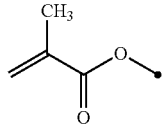
(P-2)

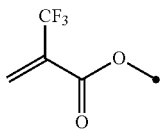
(P-3)

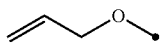
(P-4)

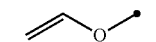
(P-5)

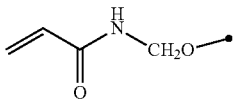
(P-6)

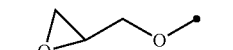
(P-7)

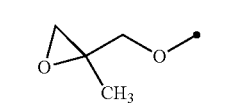
(P-8)

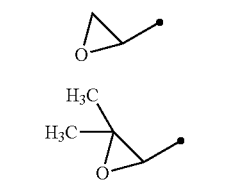
(P-9)

(P-10)

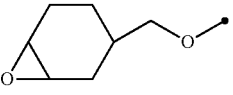
(P-11)

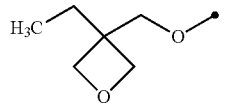
(P-12)

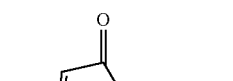
(P-13)

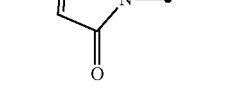
(P-14)

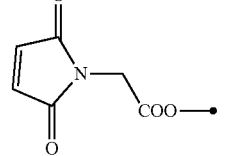

(wherein, in each formula, a black dot at the right end represents a bond.)

In formula (i), each Sp represents preferably a linear alkylene group having 1 to 18 carbon atoms or a single bond, more preferably a linear alkylene group having 2 to 15 carbon atoms or a single bond, and still more preferably a linear alkylene group having 2 to 8 carbon atoms or a single bond. However, when $K^{i1}$ represents (K-15), (K-16), or (K-17), the compound tends to have low crystallinity and tends to be in oil form, and this may cause a problem during production. Therefore, at least one Sp represents a single bond. Moreover, from the viewpoint of the solubility in a liquid crystal compound and the formation of a pretilt angle in a liquid crystal display device produced, when $K^{i1}$ represents (K-15), (K-16), or (K-17), at least one Sp represents a single bond.

The partial structure represented by any of general formulas (K-1) to (K-17) is preferably a partial structure represented by any of general formulas (K-1), (K-3), (K-6), (K-li), (K-12), and (K-13) when importance is placed on the alignment of the liquid crystal and is preferably a partial structure represented by any of general formulas (K-8), (K-11), and (K-12) when importance is placed on the solubility in the liquid crystal compound. From the viewpoint of improving the alignment of the liquid crystal, $X^{K1}$ and $Y^{K1}$ are each preferably an oxygen atom. $Z^{K1}$ represents an oxygen atom or a sulfur atom. From the viewpoint of improving the voltage holding ratio (VHR), $Z^{K1}$ is preferably an oxygen atom. $W^{K1}$ represents a methine group or a nitrogen atom and represents preferably a methine group. $U^{K1}$, $V^{K1}$, and $Z^{K1}$ each represent a methine group or a nitrogen atom. From the viewpoint of improving the alignment of the liquid crystal, $U^{K1}$, $V^{K1}$, and $Z^{K1}$ are each preferably a nitrogen atom.

$T^{K1}$ each independently represent any of general formulas (T-1) to (T-6).

[Chem. 7]

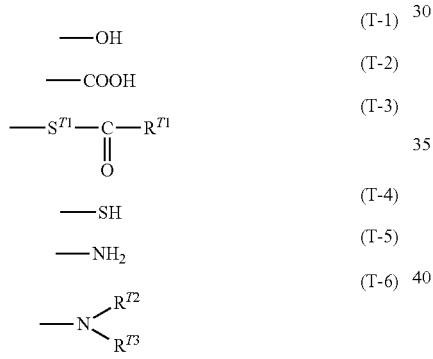

Preferably, $T^{K1}$ are each a group represented by any of general formulas (T-1), (T-3), and (T-4). In general formula (T-3), $S^{T1}$ represents preferably a single bond, a linear or branched alkylene group having 1 to 10 carbon atoms, or a linear or branched alkenylene group having 2 to 10 carbon atoms, more preferably a linear or branched alkyl group having 1 to 7 carbon atoms or a linear or branched alkenylene group having 2 to 7 carbon atoms, and still more preferably a linear alkyl group having 1 to 3 carbon atoms. Preferably, any —CH$_2$— group in the alkyl and alkylene groups is replaced by —O—, —C(=O)—, or —C(=CH$_2$)—, provided that no oxygen atoms are directly adjacent to each other. In general formula (T-3), $R^{T1}$ represents a linear or branched alkyl group having 1 to 5 carbon atoms. Preferably, any —CH$_2$— group in the alkyl group is replaced by —O—, —C(=O)—, —C(=CH$_2$)—, or —OCO—, provided that no oxygen atoms are directly adjacent to each other. $R^{T1}$ is preferably a linear alkyl group having 1 to 3 carbon atoms. Preferably, in general formula (T-3), at least two secondary carbon atoms each include —C(=O).

In general formula (T-6), $R^{T2}$ and $R^{T3}$ each independently represent a hydrogen atom or an alkyl group having 1 to 5 carbon atoms and each represent preferably a hydrogen atom. Preferred examples of general formulas (K-1) to (K-17) include (K-1-1) to (K-18-1) below. From the viewpoint of alignment and reactivity, formulas (K-1-1), (K-1-3), (K-3-1), (K-11-1), (K-12-1), (K-13-1), (K-15-1), and (K-18-1) are preferred, and formulas (K-1-1), (K-3-1), (K-11-1), and (K-13-1) are particularly preferred.

[Chem. 8]

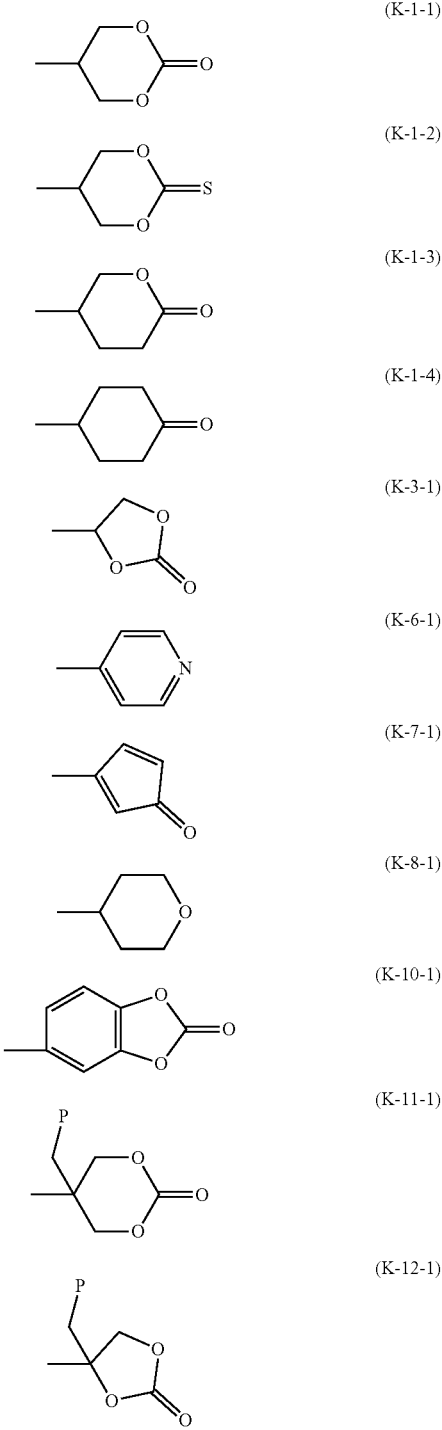

-continued

[Chem. 9]

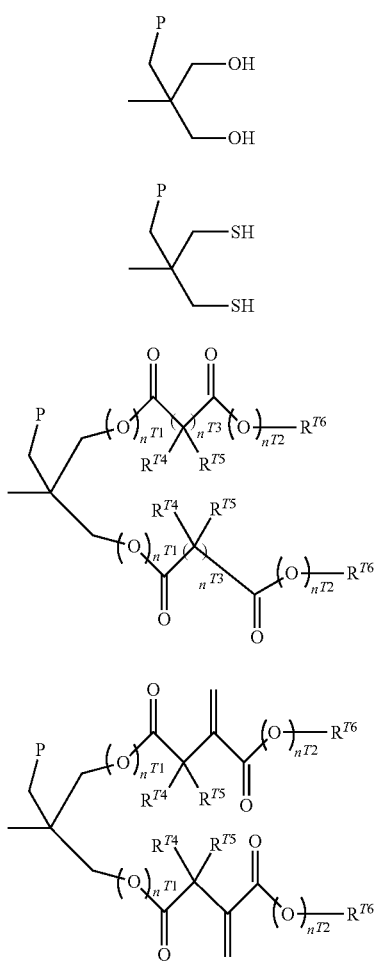

(K-13-1)
(K-13-2)
(K-13-3)
(K-13-4)

[Chem. 10]

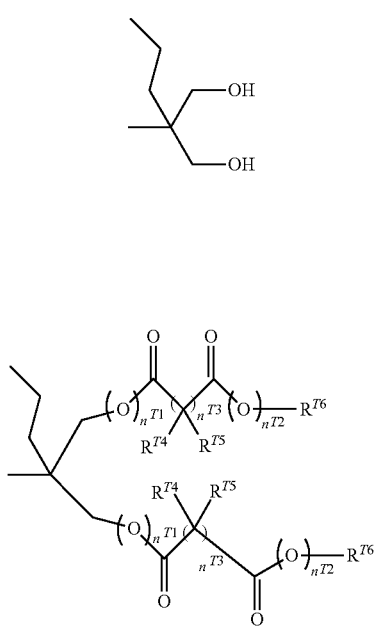

(K-15-1)
(K-15-2)

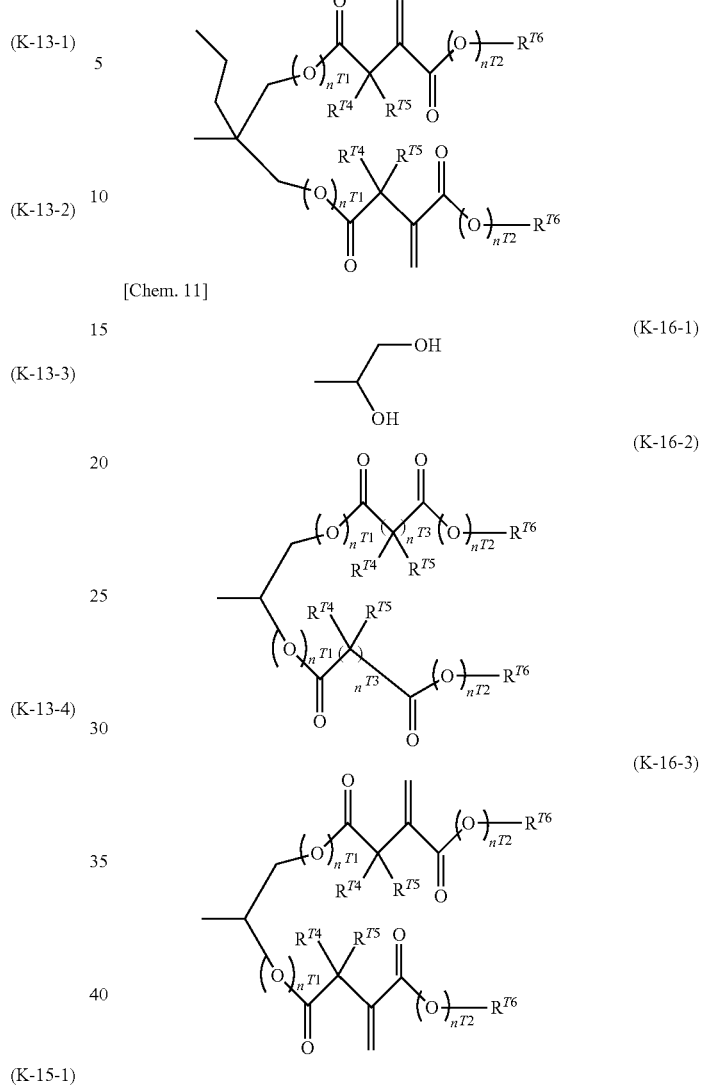

(K-15-3)

[Chem. 11]

(K-16-1)
(K-16-2)
(K-16-3)

(wherein P represents a polymerizable group; a plurality of $R^{T4}$s, a plurality of $R^{T5}$s, and a plurality of $R^{T6}$s each independently represent an alkyl group having 1 to 3 carbon atoms; a plurality of $n^{T1}$s and a plurality of $n^{T2}$s each independently represent 0 or 1; a plurality of $n^{T2}$s each independently represent an integer of 1 to 3; and $R^{T4}$s, $R^{T5}$s, $R^{T6}$s, $n^{T1}$s, $n^{T2}$s, and $n^{T3}$s may be the same or different.)

In general formula (i), $Z^{i3}$ represents preferably a single bond, —O—, —CH=CH—, —COO—, —OCO—, —OCOO—, —OCOO—, —CH=CHCOO—, —OCOCH=CH—, —CH=C(CH$_3$)COO—, —OCOC (CH$_3$)=CH—, —CH$_2$—CH(CH$_3$)COO—, —OCOCH (CH$_3$)—CH$_2$—, a linear alkylene group having 1 to 20 carbon atoms, a branched alkylene group having 1 to 20 carbon atoms, or a group obtained by replacing one —CH$_2$— group or two or more non-adjacent —CH$_2$— groups in one of the alkylene groups by —O—, —COO—, or —OCO—. $Z^{i3}$ is more preferably —COO—, —OCO—, —OCH$_2$CH$_2$O—, a linear or branched alkylene group having 1 to 6 carbon atoms, a group obtained by replacing one —CH$_2$— group in an ethylene group by —O— (—CH$_2$O— or —OCH$_2$—), or a group obtained by replacing one —CH$_2$— group in an ethylene group with —COO— or —OCO— (—CH$_2$—CH$_2$COO— or —OCOCH$_2$—CH$_2$—).

$Z^{i3}$ represents preferably —$Z^{i31}$—$S^{i1}$— ($Z^{i31}$— represents —O—, —COO—, —OCO—, or an alkylene group having 1 to 6 carbon atoms, one —CH$_2$— group or two or more non-adjacent —CH$_2$— groups in the alkylene group being optionally replaced by —O—, —COO—, or —OCO—; and $S^{i1}$ represents an alkyl group having 1 to 6 carbon atoms).

In formula (i), $Z^1$ and $Z^2$ each represent preferably a single bond, —CH═CH—, —CF═CF—, —C≡C—, —COO—, —OCO—, —CF$_2$O—, —OCF$_2$—, —CH═CHCOO—, —OCOCH═CH—, —OCH$_2$CH$_2$O—, an alkylene group having 1 to 10 carbon atoms, or a group obtained by replacing one —CH$_2$— group or two or more non-adjacent —CH$_2$— groups in the alkylene group by —O—, —COO—, or —OCO—, more preferably a single bond, —COO—, —OCO—, —CH═CHCOO—, —OCOCH═CH—, —OCH$_2$CH$_2$O—, a linear or branched alkylene group having 1 to 6 carbon atoms, or a group obtained by replacing one —CH$_2$— group or two or more non-adjacent —CH$_2$— groups in the alkylene group by —O—, —OCO—, or —OCO—, and still more preferably a single bond, —COO—, —OCO—, —OCH$_2$CH$_2$O—, an alkylene group having 2 carbon atoms (an ethylene group (—CH$_2$CH$_2$—)), a group obtained by replacing one —CH$_2$— group in an ethylene group by —O— (—CH$_2$O— or —OCH$_2$—), or a group obtained by replacing one —CH$_2$— group in an ethylene group by —COO— or —OCO— (—CH$_2$—CH$_2$COO— or —OCOCH$_2$—CH$_2$—).

$R^{i1}$ represents preferably a hydrogen atom, P-Sp-, a linear or branched alkyl group having 1 to 20 carbon atoms, or a halogenated alkyl group, any —CH$_2$— group in each alkyl group being optionally replaced by —CH═CH—, —C≡C—, —O—, —COO—, —OCO—, or —OCOO—, provided that no —O— groups are adjacent to each other. $R^{i1}$ represents more preferably a linear or branched alkyl group having 1 to 18 carbon atoms, any —CH$_2$— group in the alkyl group being optionally replaced by —CH═CH—, —O—, or —OCO— (provided that no —O— groups are adjacent to each other). From the viewpoint of improving the alignment of the liquid crystal compound, the number of carbon atoms in $R^{i1}$ is preferably 3 or more, more preferably 4 or more, and still more preferably 5 or more.

Ring A and ring C are each preferably a divalent cyclic aromatic group, a divalent heterocyclic aromatic group, a divalent cyclic aliphatic group, or a divalent heterocyclic aliphatic group and are each specifically preferably a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a chroman-3,7-diyl, a 1,2,3,4-tetrahydronaphthalene-2,6-diyl group, or a 1,3-dioxane-2,5-diyl group, and these cyclic structures are preferably unsubstituted or substituted with $L^{i1}$. $L^{i1}$ is preferably an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or P-Sp- and more preferably an alkyl group having 1 to 6 carbon atoms, an alkoxy group having 1 to 6 carbon atoms, or a group substituted with a halogen atom. When $L^{i1}$ represents a monovalent organic group having a substituent represented by general formula $K^{i1}$, $L^{i1}$ represents preferably —$Z^{i3}$—$K^{i3}$ ($Z^{i3}$ and $K^{i3}$ have the same meanings as $Z^{i3}$ and $K^{i3}$ in general formula (i)). Ring A and ring C are each more preferably one of a 1,4-phenylene group, a 2,6-naphthalene group, and a 1,4-cyclohexyl group that are optionally substituted with an alkyl group having 1 to 12 carbon atoms, a halogenated alkyl group having 1 to 12 carbon atoms, an alkoxy group having 1 to 12 carbon atoms, a halogen atom, or P-Sp-. Moreover, ring C represents preferably a ring structure selected from a 1,3-phenylene group, a 1,3-cyclohexylene group, and a naphthalene 2,5-diyl group.

Ring B represents preferably a 1,4-phenylene group and more preferably has two P-Sp- groups. No particular limitation is imposed on the positions of the P-Sp- groups in Ring B. Ring B is preferably any of the following groups.

[Chem. 12]

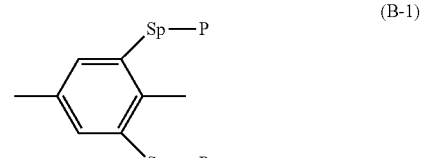
(B-1)

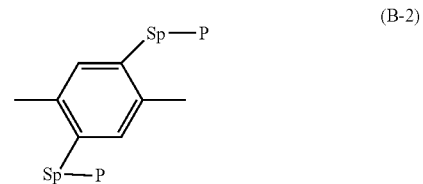
(B-2)

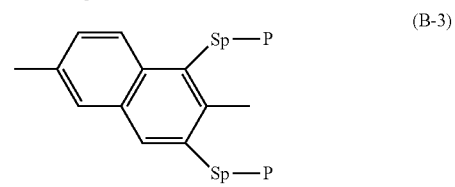
(B-3)

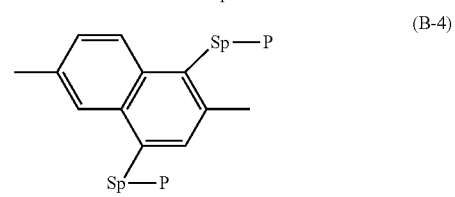
(B-4)

m represents preferably an integer of 1 to 4 and more preferably an integer of 2 to 3. n represents 0 or 1.

Particularly preferably, general formula (i) represents general formula (i-1) below.

[Chem. 13]

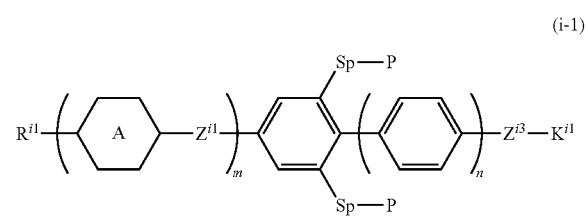
(i-1)

(wherein $R^{i1}$, $Z^{i1}$, $Z^{i3}$, $K^{i1}$, Sp, P, m, and n each independently have the same meanings as $R^{i1}$, $Z^{i1}$, $Z^{i3}$, $K^{i1}$, Sp, P, m, and n, respectively, in general formula (i).)

Specific examples of general formula (i) include, but not limited to, formulas (R-1-1) to (R-1-23) below.

[Chem. 14]
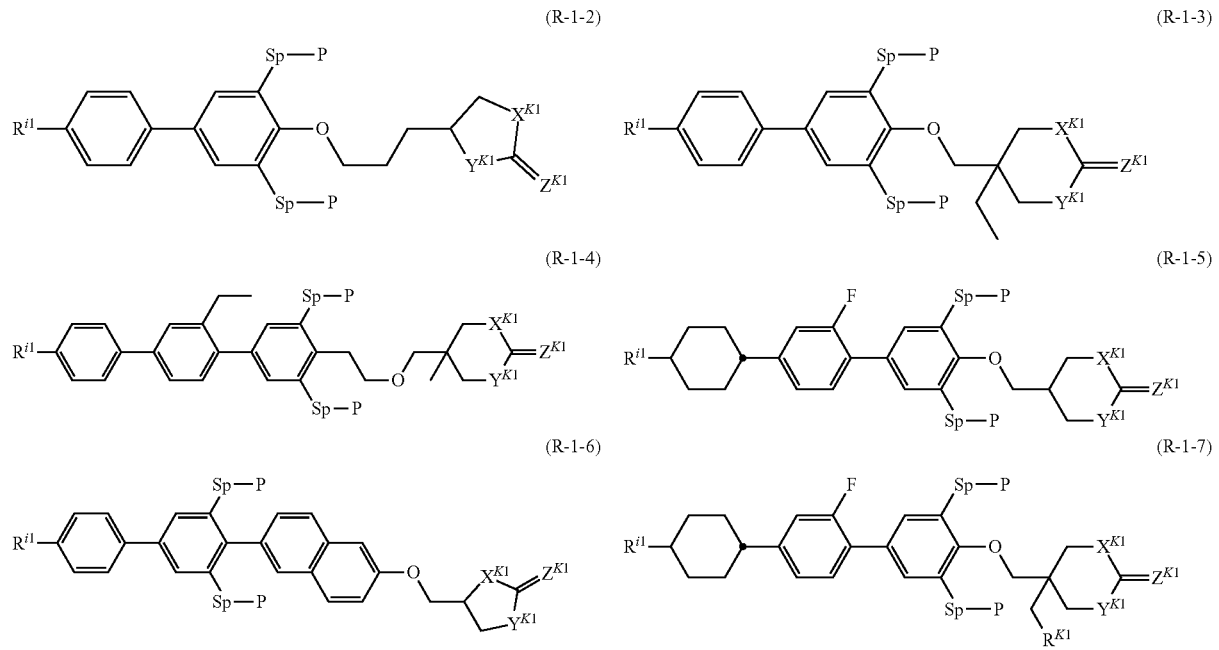
[Chem. 15]
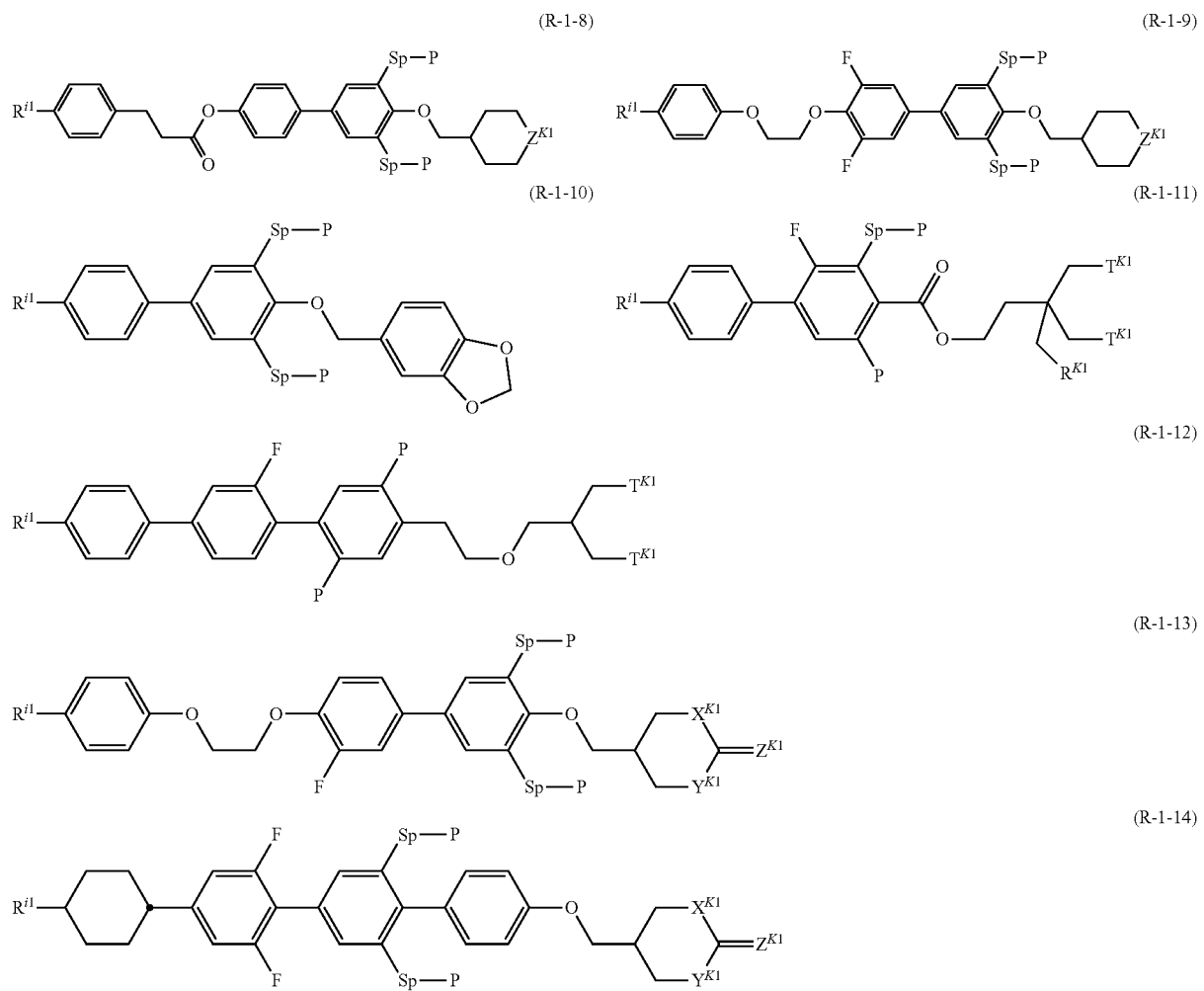

-continued
[Chem. 16]
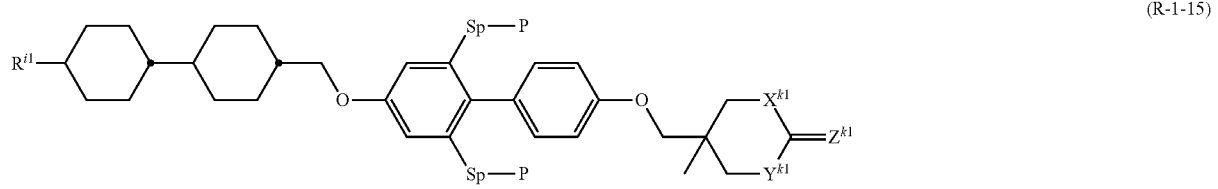
(R-1-15)
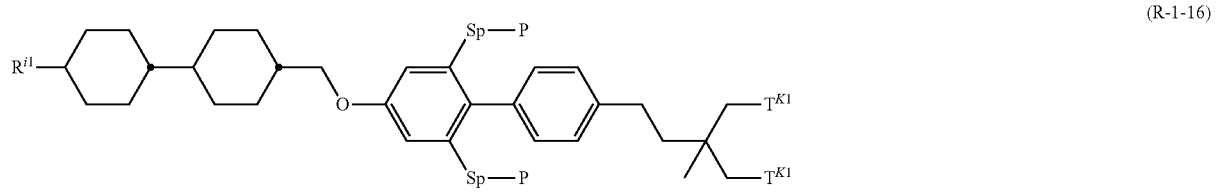
(R-1-16)
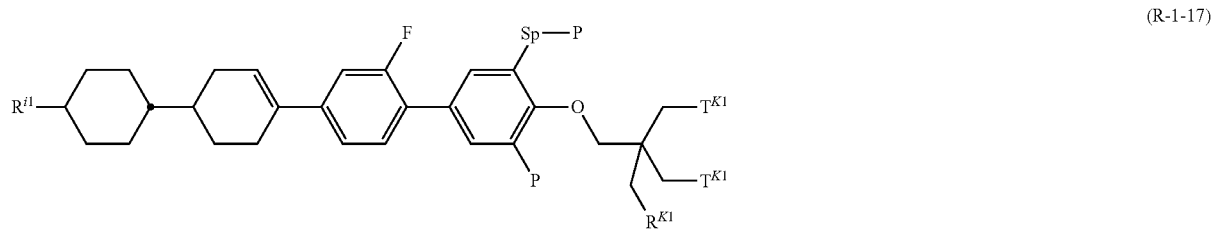
(R-1-17)
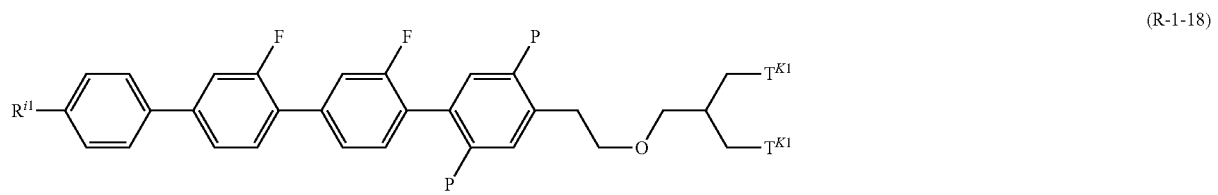
(R-1-18)
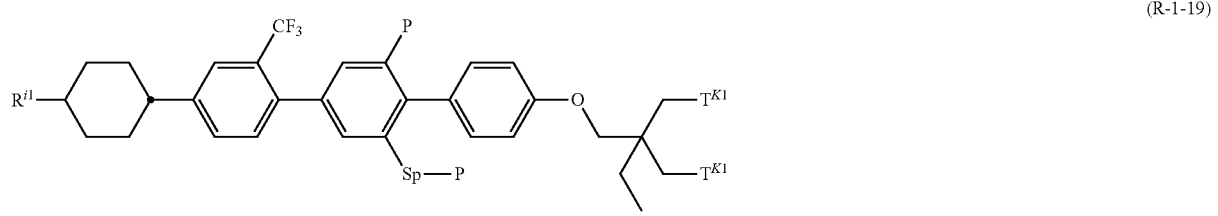
(R-1-19)
[Chem. 17]
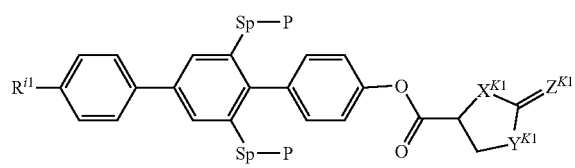
(R-1-20)
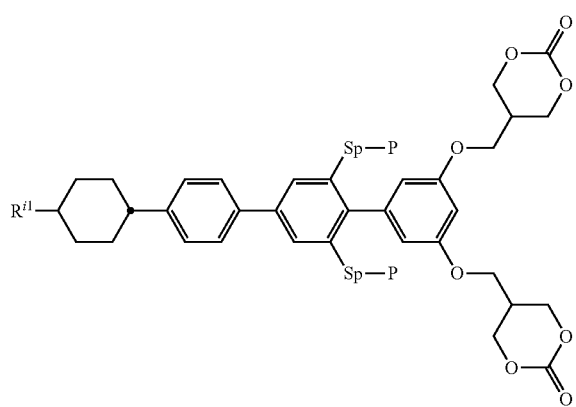
(R-1-21)

(R-1-22)

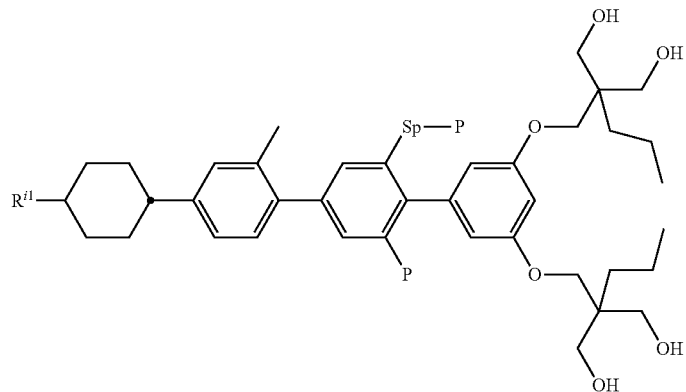

(R-1-23)

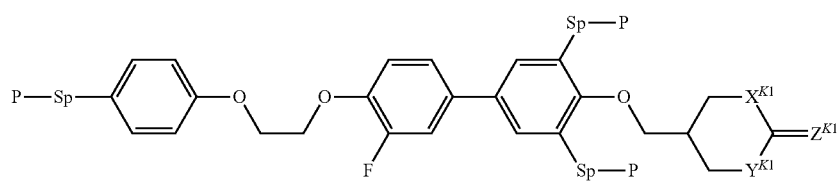

(wherein $R^{i1}$, $X^{K1}$, $Y^{K1}$, $Z^{K1}$, $T^{K1}$, Sp, P, m, and n each independently have the same meanings as $R^{i1}$, $X^{K1}$, $Y^{K1}$, $Z^{K1}$, $T^{K1}$, Sp, P, m, and n, respectively, in general formula (i).)

In general formula (i-1), formulas (R-1-1) to (R-1-23), etc., preferable groups for each symbol are the same as those for general formula (i).

One or two or more compounds represented by general formula (i) in the present invention may be added to a liquid crystal composition. In addition to the compound represented by general formula (i), a well-known polymerizable compound, a well-known antioxidant, etc. used for a liquid crystal composition may be further added. Specific examples of the compound (i) include (P-1-1) to (P-1-21) below.

[Chem. 18]

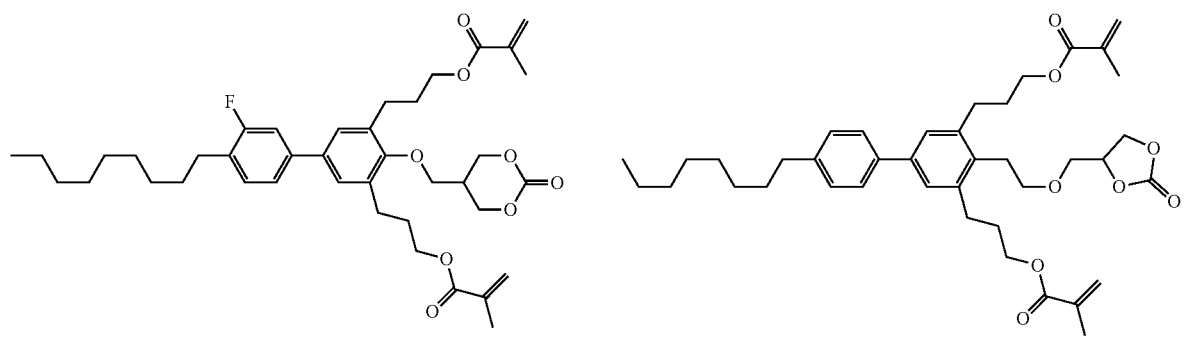

(P-1-1)     (P-1-2)

(P-1-3)
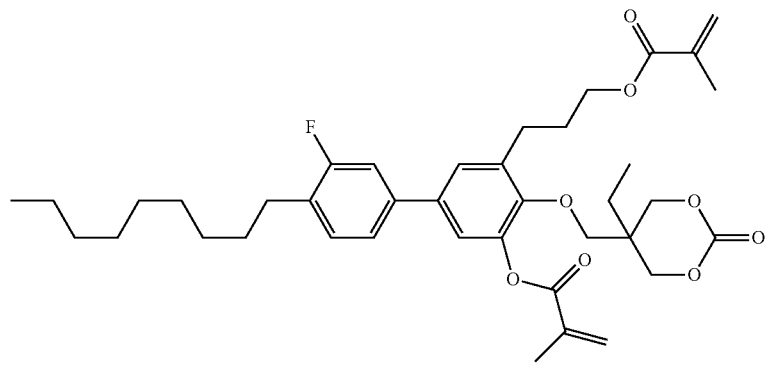
(P-1-4)
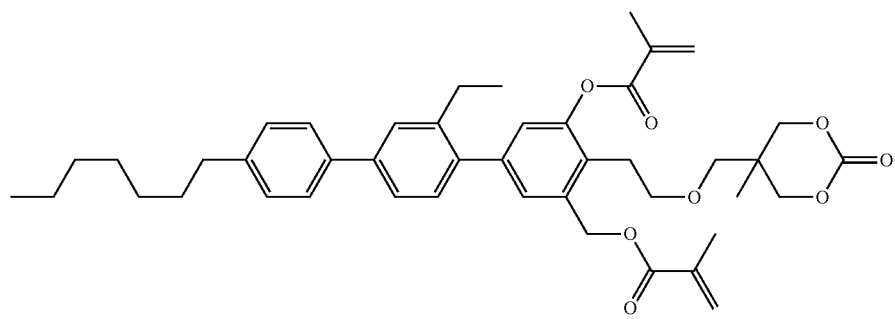
[Chem. 19]
(P-1-5)
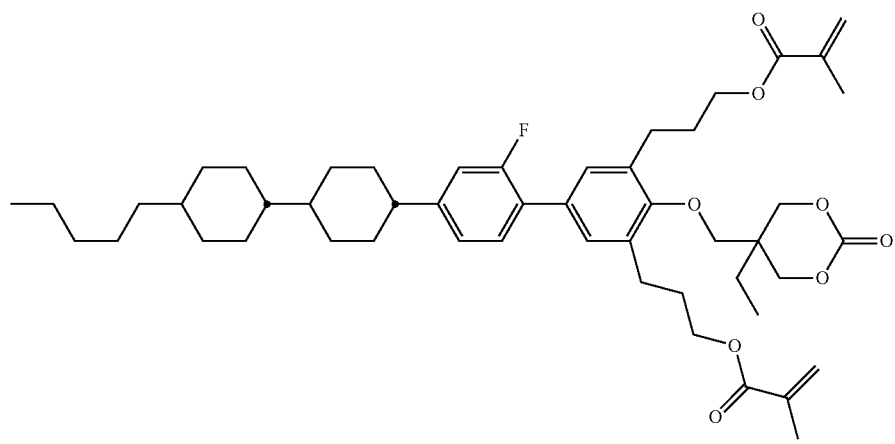
(P-1-6)
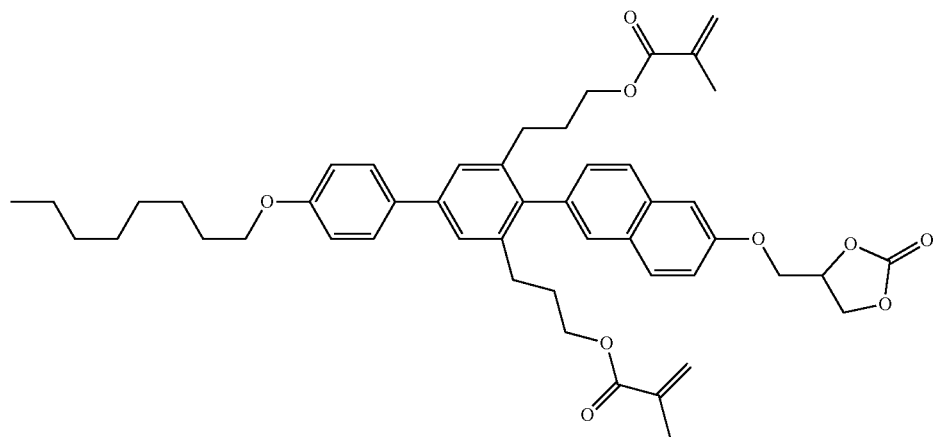

-continued
(P-1-7)
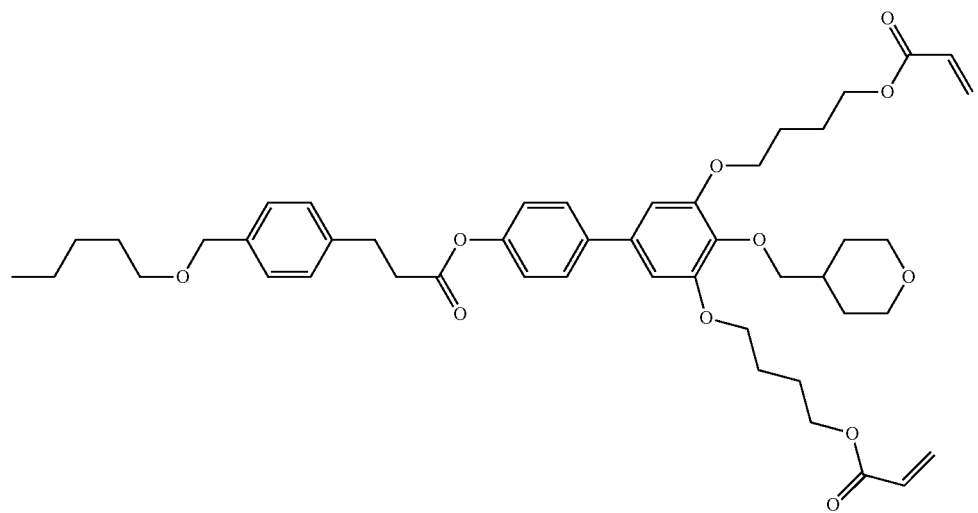
(P-1-8)
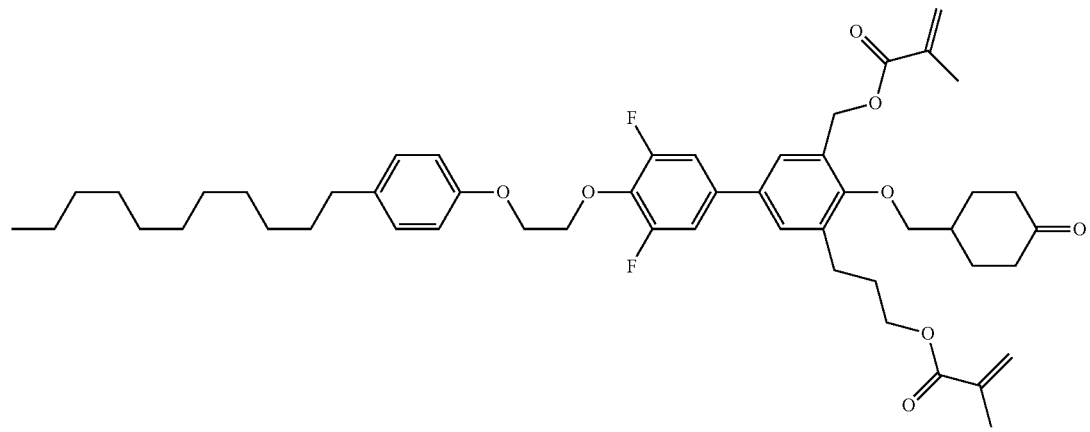
[Chem. 20]
(P-1-9)
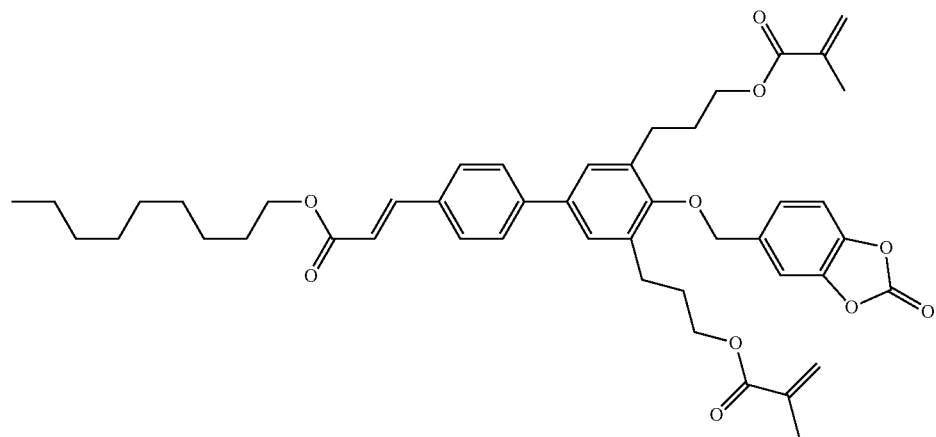

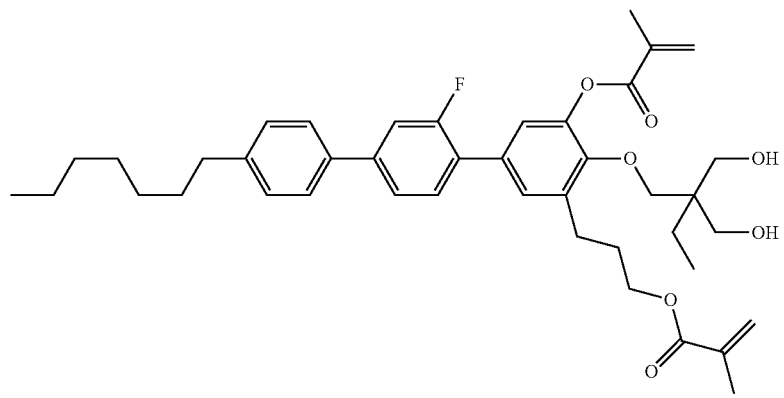
(P-1-10)
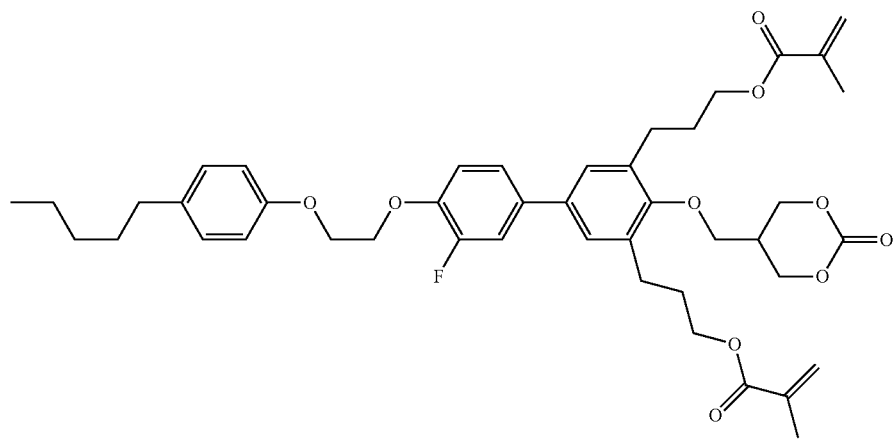
(P-1-11)
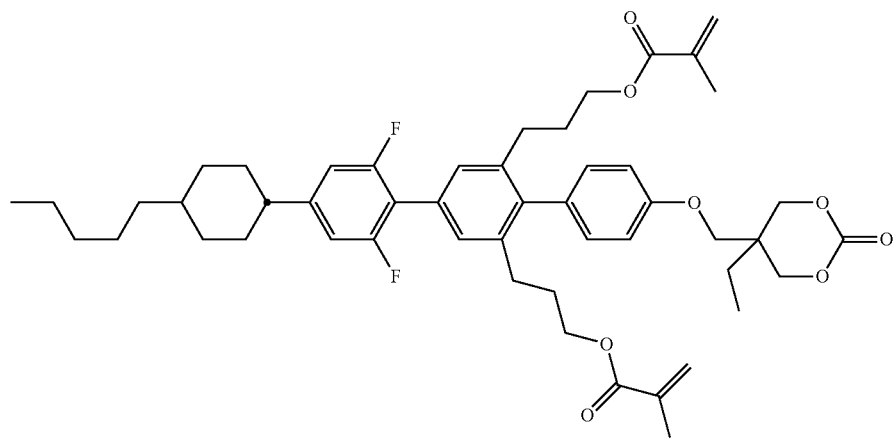
(P-1-12)

(P-1-13)
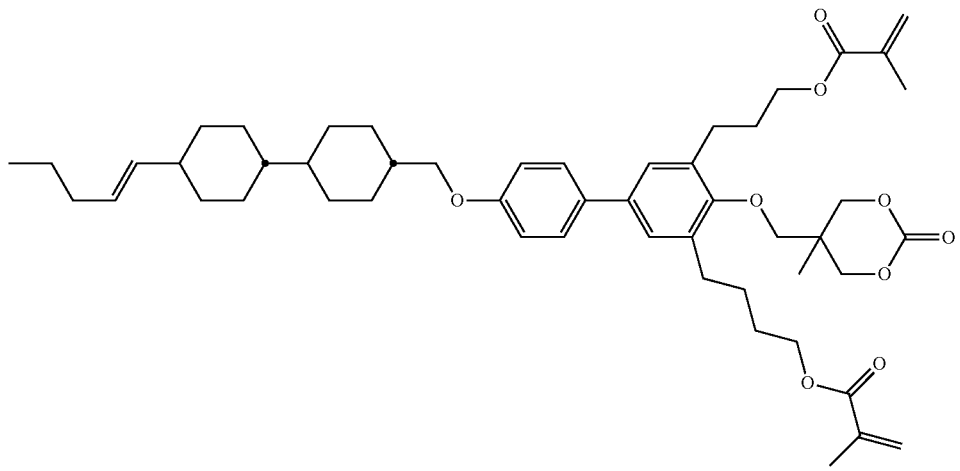
(P-1-14)
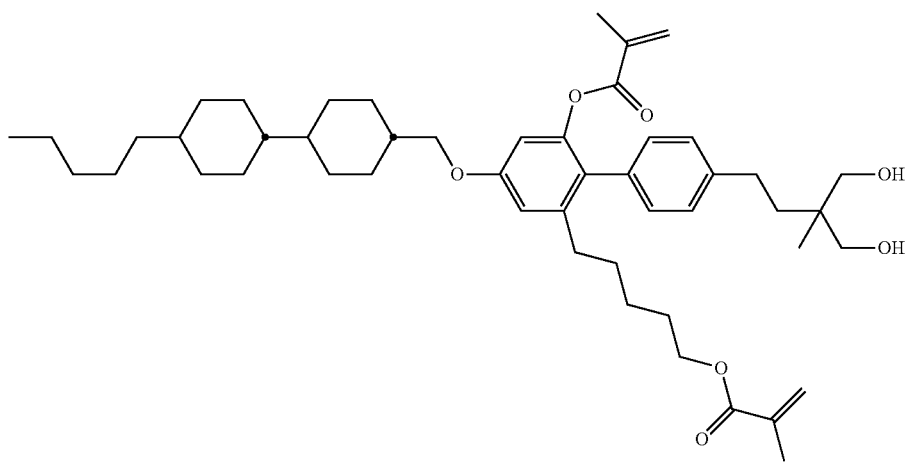
(P-1-15)
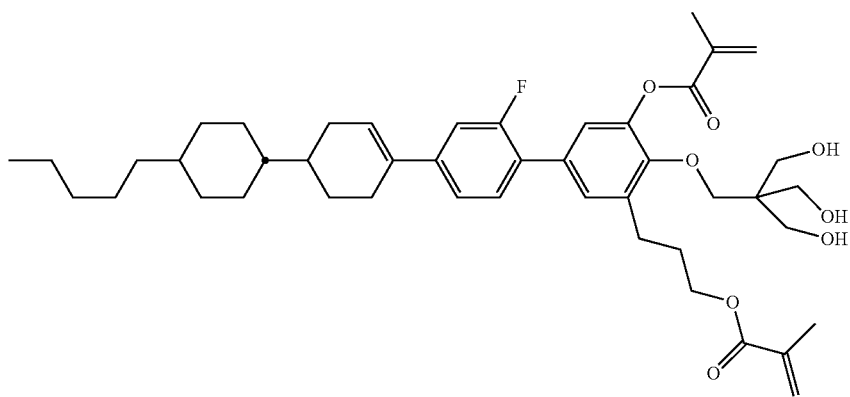

(P-1-16)
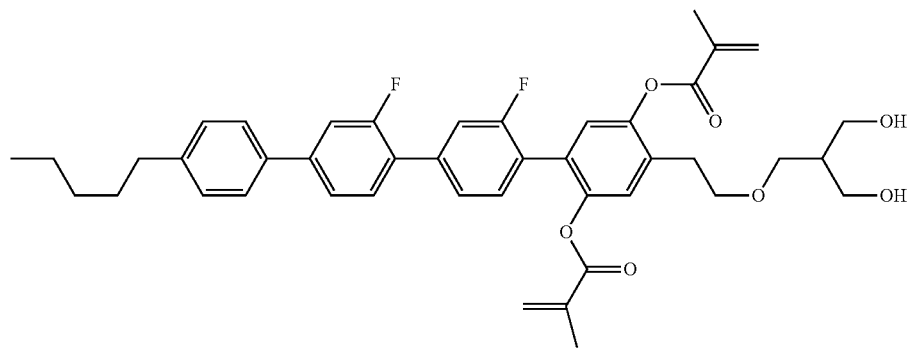
[Chem. 22]
(P-1-17)
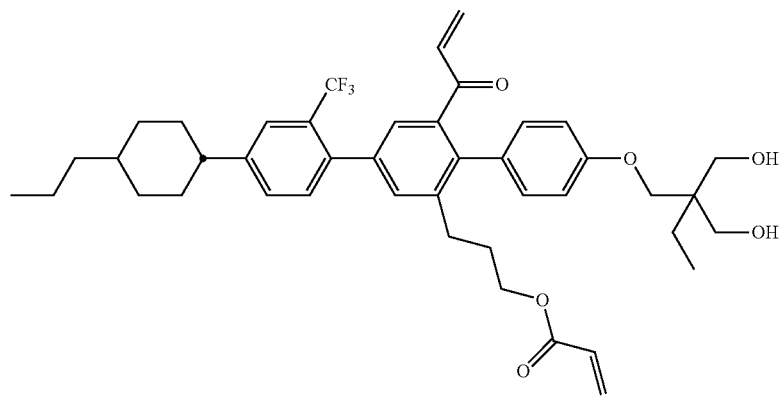
(P-1-18)
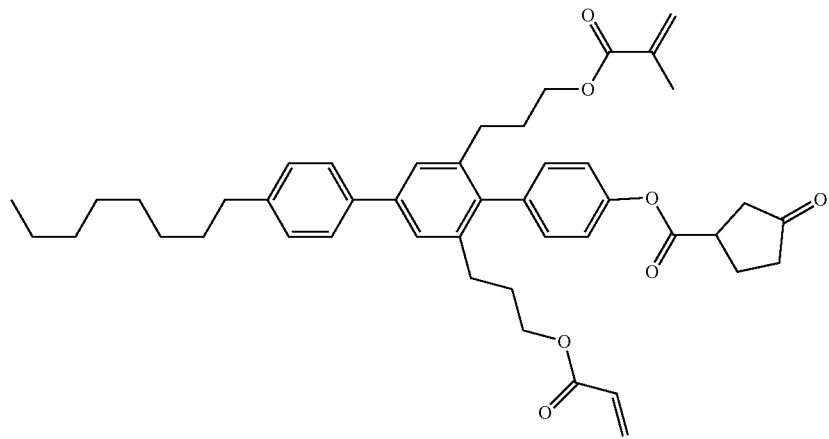

(P-1-19)
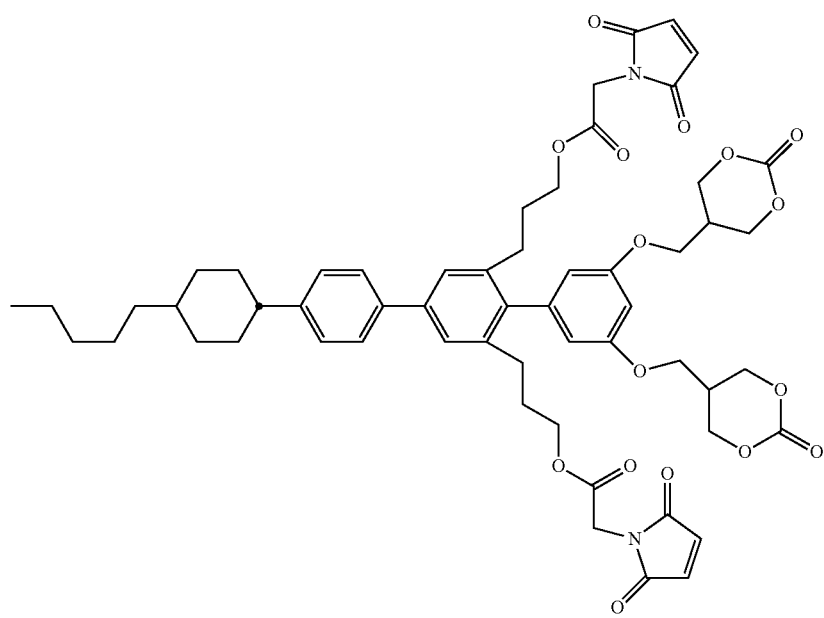
[Chem. 23]
(P-1-20)
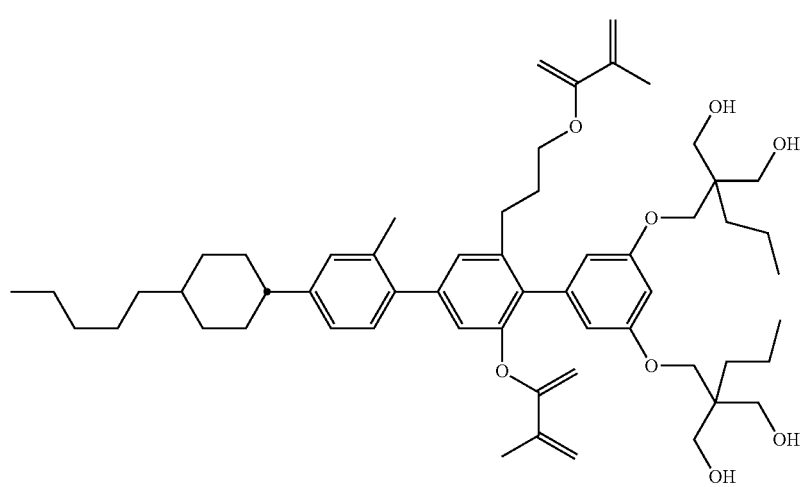
(P-1-21)
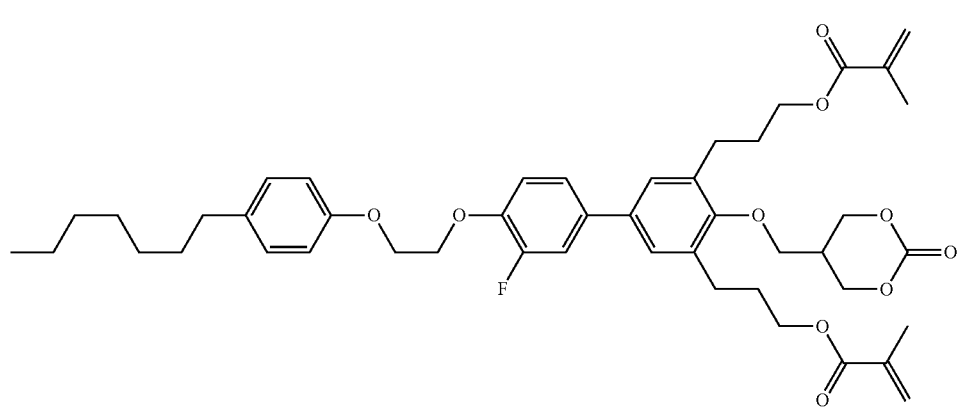

(Production Method 1) Production of Compound Represented by General Formula (P-1-2)

4-Octylphenylboronic acid and compound (SS-1) having a structure shown below are subjected to the Suzuki coupling reaction using a palladium catalyst to obtain (S-1).

Next, an esterification reaction with methacrylic acid and a pyran removing reaction using hydrochloric acid are performed to obtain structure (S-3) below. Then etherification by the Mitsunobu reaction between (S-3) and glycerol 1,2-carbonate is performed, and target compound (P-1-2) can thereby be obtained.

[Chem. 24]

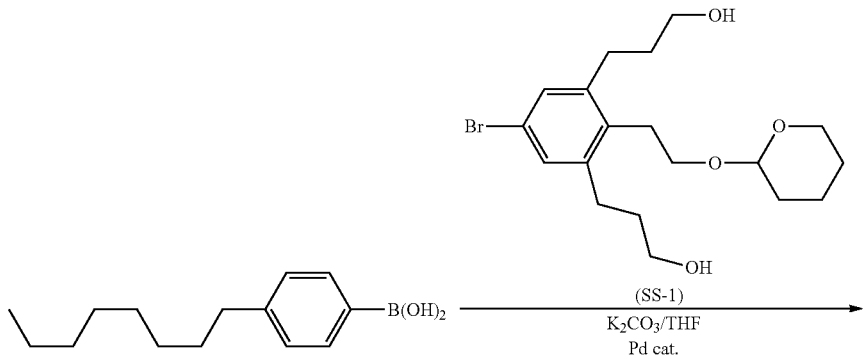

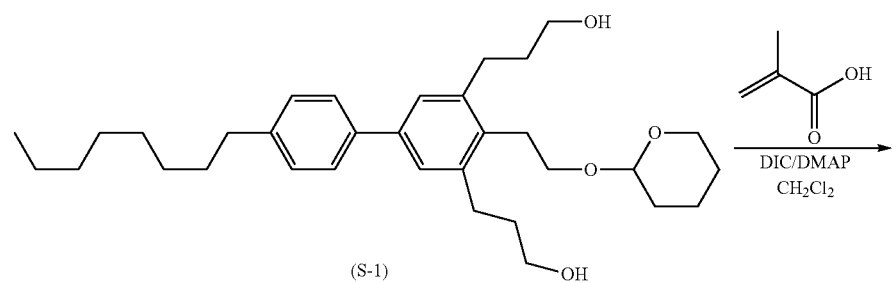

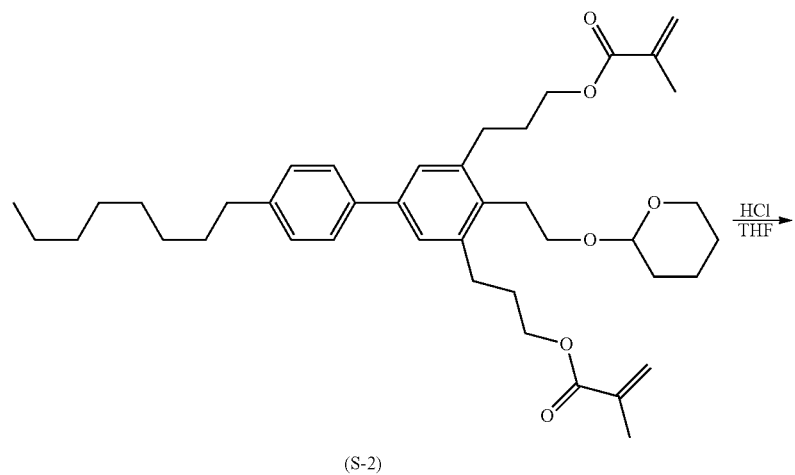

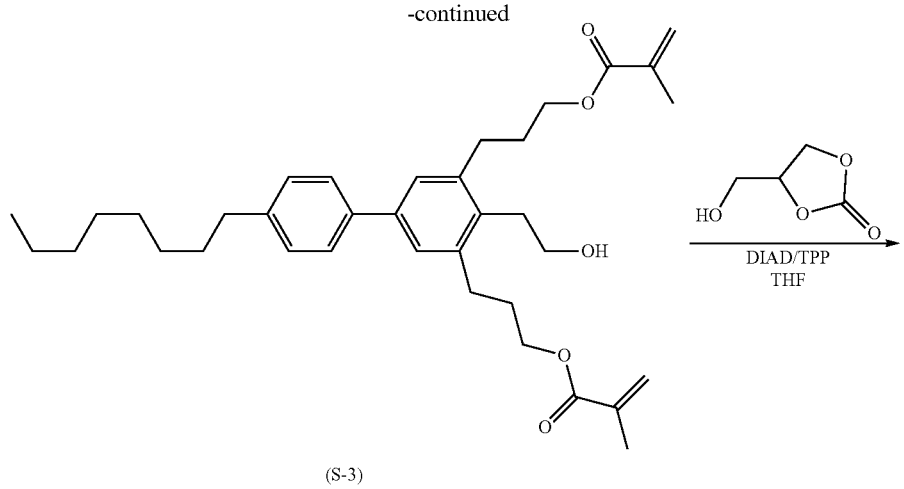

(S-3)

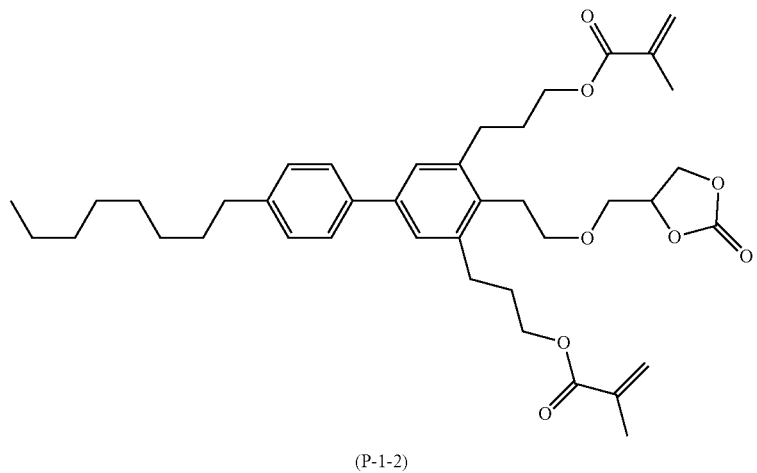

(P-1-2)

(Production Method 2) Production of Compound Represented by General Formula (P-1-4)

(3-Ethyl-4'-heptyl-[1,1'-biphenyl]-4-yl)boronic acid and compound (SS-2) having a structure shown below are subjected to the Suzuki coupling reaction using a palladium catalyst to obtain (S-4). Next, an esterification reaction with methacrylic acid and a deacetalization reaction using hydrochloric acid are performed to obtain structure (S-6) below. Then (S-6) is reacted with ethyl chloroformate, and target compound (P-1-4) can thereby be obtained.

[Chem. 25]

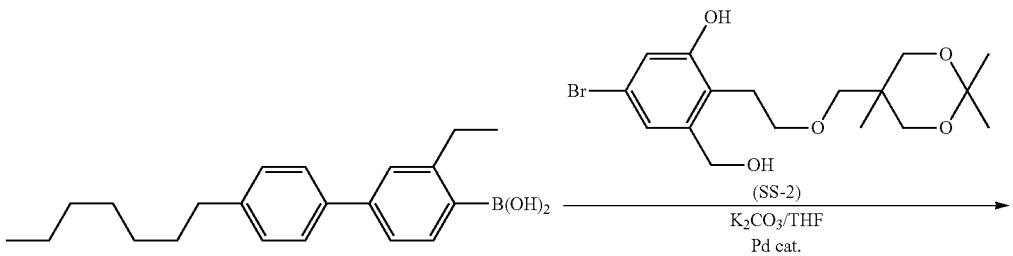

-continued

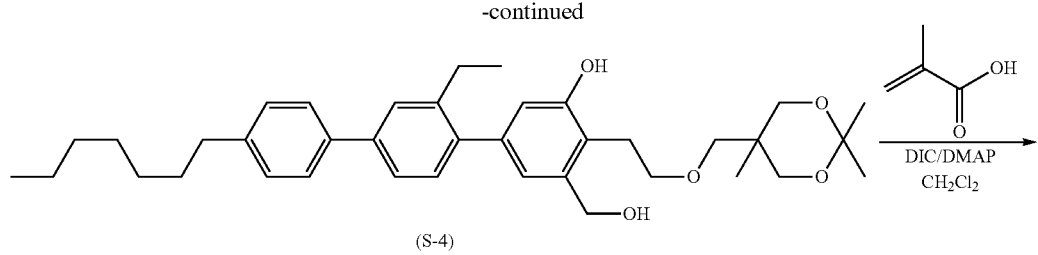
(S-4)

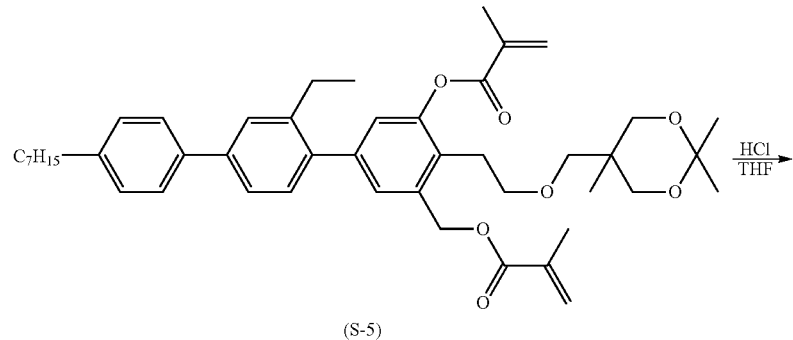
(S-5)

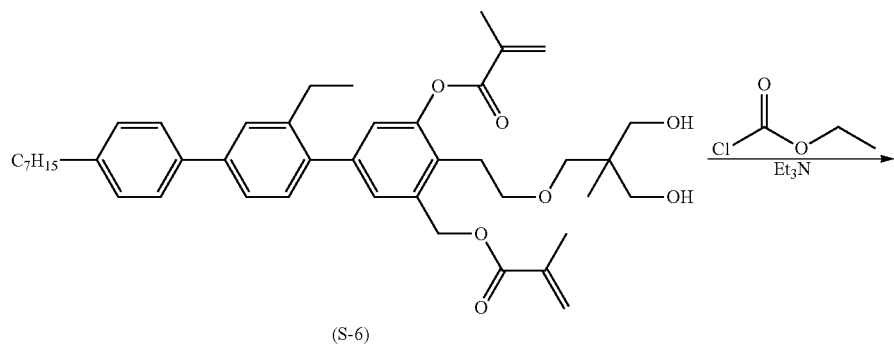
(S-6)

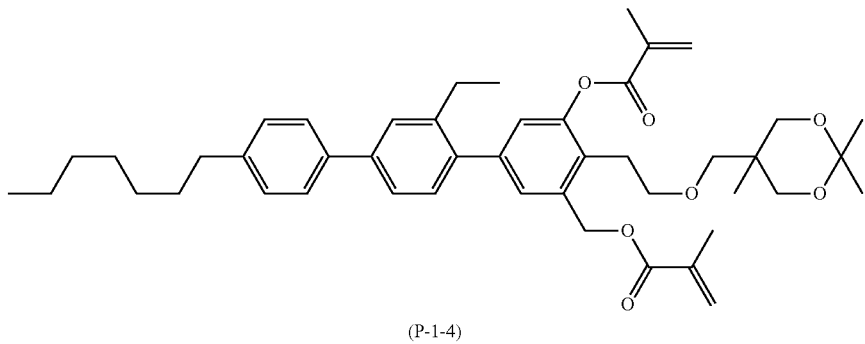
(P-1-4)

(Production Method 3) Production of Compound Represented by General Formula (P-1-8)

Etherification by the Mitsunobu reaction between 4-undecylphenol and ethylene glycol mono-tertiary butyl ether is performed to obtain 1-(2-t-butyloxyethoxy)-4-undecylphenyl. Next, formic acid is used to remove the tertiary butyl group, and compound (S-7) in which a hydroxyl group has been mesylated by methanesulfonic acid chloride is obtained. The compound obtained and compound (SS-3) below are etherified to obtain compound (S-8). Compound (S-8) is reduced using sodium borohydride to convert an aldehyde group to a hydroxyl group and esterified with methacrylic acid to obtain compound (S-9). Then hydrochloric acid is used to remove a pyran ring. The resulting compound and 4-(hydroxymethyl)cyclohexan-1-one are etherified by the Mitsunobu reaction, and target compound (P-1-8) can thereby be obtained.

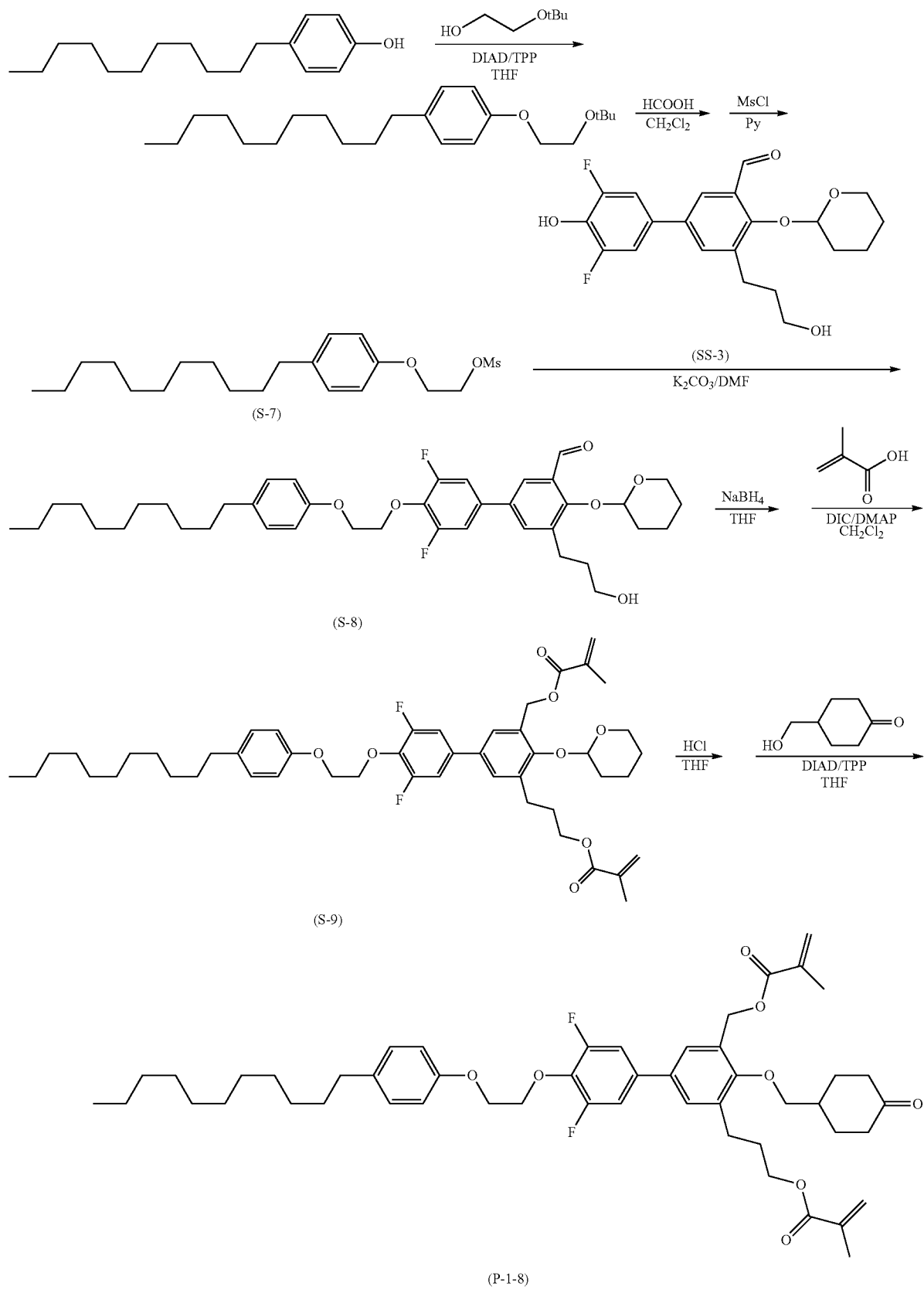

(Production Method 4) Production of Compound Represented by General Formula (P-1-10)

(3-Fluoro-4'-heptyl-1,1'-biphenyl-4-yl)boronic acid and compound (SS-4) having a structure shown below are subjected to the Suzuki coupling reaction using a palladium catalyst to obtain (S-10). Then an esterification reaction with methacrylic acid and deacetalization using hydrochloric acid are performed, and target compound (P-1-10) can thereby be obtained.

[Chem. 27]

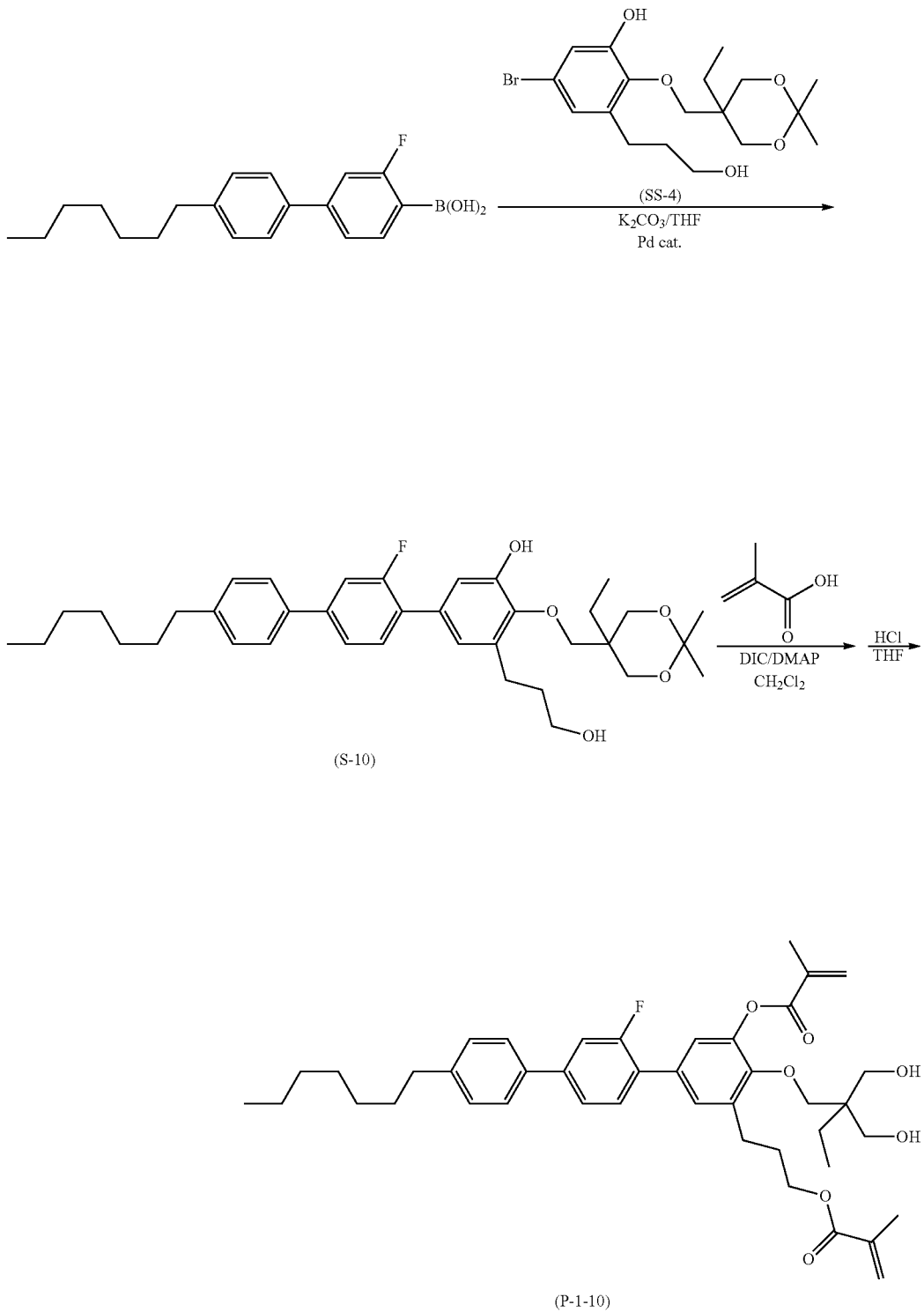

(Production Method 5) Production of Compound Represented by General Formula (P-1-15)

4'-Pentyl-(1,1'-bicyclohexan)-4-one, 4-bromo-2-fluoro-anisole, and compound (SS-5) having a structure shown below are subjected to the Grignard reaction, and the resulting compound is subjected to thermal dehydration to obtain (S-11) having a cyclohexene skeleton introduced therein. Then hydrobromic acid is used to remove a methoxy group to obtain compound (S-12). Compound (S-12) is triflated with trifluoromethanesulfonic anhydride, and the resulting compound and compound (SS-5) shown below are subjected to the Suzuki coupling reaction using a palladium catalyst. An esterification reaction with methacrylic acid and a deprotection process using sulfuric acid are performed, and target compound (P-1-15) can thereby be obtained.

represented by general formula (i) and contained in the liquid crystal composition is the same as the above-described compound (i), e.g., any of the compounds represented by formulas (R-1-1) to (R-1-23), and the description thereof will be omitted.

The content of compound (i) is preferably 0.01 to 50% by mass. In terms of allowing liquid crystal molecules to be aligned more preferably, the lower limit of the content of compound (i) is preferably 0.01% by mass or more, 0.1% by mass or more, 0.5% by mass or more, 0.7% by mass or more, or 1% by mass or more based on the total mass of the liquid crystal composition. In terms of obtaining good response characteristics, the upper limit of the content of compound (i) is preferably 50% by mass or less, 30% by mass or less, 10% by mass or less, and is more preferably 7% by mass or

[Chem. 28]

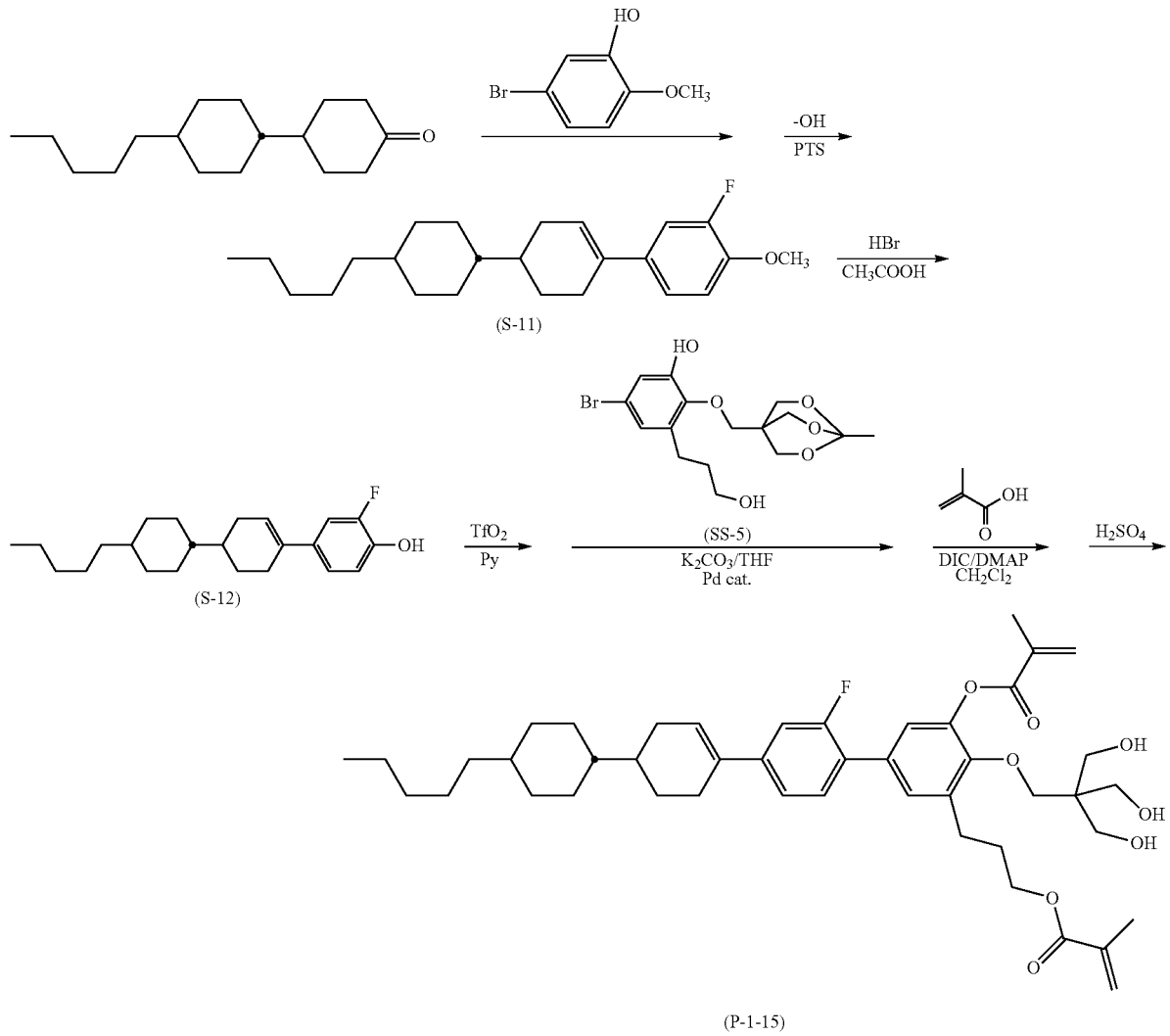

less, 5% by mass or less, 4% by mass or less, or 3% by mass or less based on the total mass of the liquid crystal composition.

The liquid crystal composition may further contain a compound selected from the group consisting of compounds represented by general formulas (N-1), (N-2), and (N-3):

(Liquid Crystal Composition)

A liquid crystal composition in an embodiment contains one or two or more compounds each having the partial structure represented by general formula (i) above. Preferably, this liquid crystal composition has negative dielectric anisotropy ($\Delta\varepsilon$). Each compound having the partial structure

[Chem. 29]

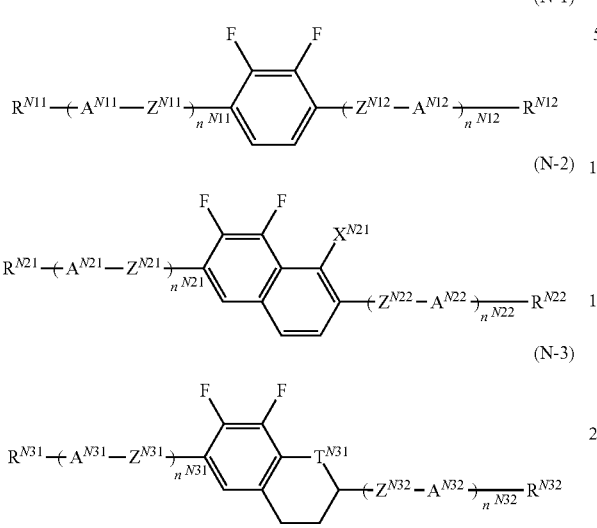

as a non-polymerizable liquid crystal compound.

In formulas (N-1), (N-2), and (N-3), $R^{N11}$, $R^{N12}$, $R^{N21}$, $R^{N22}$, $R^{N31}$, and $R^{N32}$ each independently represent an alkyl group having 1 to 8 carbon atoms, one —$CH_2$— group or two or more non-adjacent —$CH_2$— groups in the alkyl group being each independently optionally replaced by —CH=CH—, —C≡C—, —O—, —CO—, —COO—, or —OCO—;

$A^{N11}$, $A^{N12}$, $A^{N21}$, $A^{N22}$, $A^{N31}$, and $A^{N32}$ each independently represent a group selected from the group consisting of (a) a 1,4-cyclohexylene group (one —$CH_2$— group or two or more non-adjacent —$CH_2$— groups present in the 1,4-cyclohexylene group are optionally replaced by —O—), (b) a 1,4-phenylene group (one —CH= group or two or more non-adjacent —CH= groups present in the 1,4-phenylene group are optionally replaced by —N=), (c) a naphthalene-2,6-diyl group, a 1,2,3,4-tetrahydronaphthalene-2,6-diyl group, or a decahydronaphthalene-2,6-diyl group (one —CH= group or two or more non-adjacent —CH= groups present in the naphthalene-2,6-diyl group or the 1,2,3,4-tetrahydronaphthalene-2,6-diyl group are optionally replaced by —N=), and (d) a 1,4-cyclohexenylene group, groups (a), (b), (c), and (d) being each independently substituted with a cyano group, a fluorine atom, or a chlorine atom;

$Z^{N11}$, $Z^{N12}$, $Z^{N21}$, $Z^{N22}$, $Z^{N31}$, and $Z^{N32}$ each independently represent a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—;

$X^{N21}$ represents a hydrogen atom or a fluorine atom;

$T^{N31}$ represents —$CH_2$— or an oxygen atom;

$n^{N11}$, $n^{N12}$, $n^{N21}$, $n^{N22}$, $n^{N31}$, and $n^{N32}$ each independently represent an integer of 0 to 3, provided that $n^{N11}+n^{N12}$, $n^{N21}+n^{N22}$, and $n^{N31}+n^{N32}$ each independently represent 1, 2, or 3; and when a plurality of $A^{N11}$s to $A^{N32}$s and $Z^{N11}$s to $Z^{N32}$s are present, they may be the same or different.

Preferably, the compound represented by any of general formulas (N-1), (N-2), and (N-3) is a compound in which Δε is negative and its absolute value is larger than 3.

In general formulas (N-1), (N-2), and (N-3), $R^{N11}$, $R^{N12}$, $R^{N21}$, $R^{N22}$, $R^{N31}$, and $R^{N32}$ each independently represent more preferably an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, preferably an alkyl group having 1 to 5 carbon atoms, an alkoxy group having 1 to 5 carbon atoms, an alkenyl group having 2 to 5 carbon atoms, or an alkenyloxy group having 2 to 5 carbon atoms, still more preferably an alkyl group having 1 to 5 carbon atoms or an alkenyl group having 2 to 5 carbon atoms, yet more preferably an alkyl group having 2 to 5 carbon atoms or an alkenyl group having 2 to 3 carbon atoms, and particularly preferably an alkenyl group having 3 carbon atoms (propenyl group).

When a ring structure to which one group of $R^{N11}$, $R^{N12}$, $R^{N21}$, $R^{N22}$, $R^{N31}$, and $R^{N32}$ is bonded is a phenyl group (aromatic group), the one group is preferably a linear alkyl group having 1 to 5 carbon atoms, a linear alkoxy group having 1 to 4 carbon atoms, or an alkenyl group having 4 to 5 carbon atoms. When a ring structure to which one group of $R^{N11}$, $R^{N12}$, $R^{N21}$, $R^{N22}$, $R^{N31}$, and $R^{N32}$ is bonded is a saturated ring structure such as cyclohexane, pyran, or dioxane, the one group is preferably a linear alkyl group having 1 to 5 carbon atoms, a linear alkoxy group having 1 to 4 carbon atoms, or a linear alkenyl group having 2 to 5 carbon atoms. To stabilize a nematic phase, the total number of carbon atoms and, if present, oxygen atoms is preferably 5 or less, and the one group is preferably linear.

The alkenyl group is preferably a group selected from groups represented by formula (R1) to formula (R5) (a black dot in each formula represents a bond).

[Chem. 30]

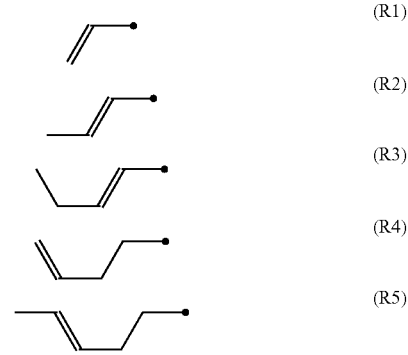

When there is a need to increase Δn, $A^{N11}$, $A^{N12}$, $A^{N21}$, $A^{N22}$, $A^{N31}$, and $A^{N32}$ each independently represent preferably an aromatic group. When there is a need to improve the speed of response, $A^{N11}$, $A^{N12}$, $A^{N21}$, $A^{N22}$, $A^{N31}$, and $A^{N32}$ each independently represent preferably an aliphatic group, preferably a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably any of the following structures:

[Chem. 31]

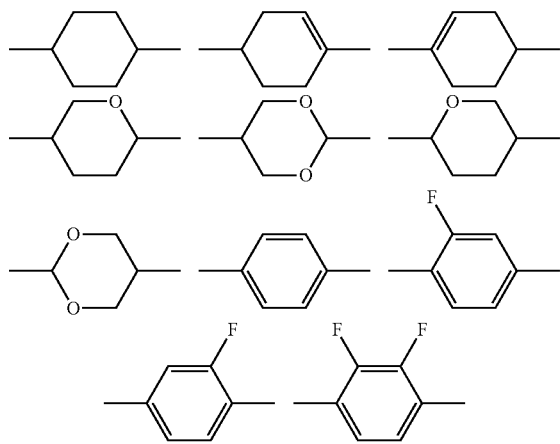

and still more preferably a trans-1,4-cyclohexylene group, a 1,4-cyclohexenylene group, or a 1,4-phenylene group.

$Z^{N11}$, $Z^{N12}$, $Z^{N21}$, $Z^{N22}$, $Z^{N31}$, and $Z^{N32}$ each independently represent —CH$_2$O—, —CF$_2$O—, —CH$_2$CH$_2$—, —CF$_2$CF$_2$—, or a single bond, more preferably —CH$_2$O—, —CH$_2$CH$_2$—, or a single bond, and particularly preferably —CH$_2$O— or a single bond.

$X^{N21}$ is preferably a fluorine atom.

$T^{N31}$ is preferably an oxygen atom.

$n^{N11}+n^{N12}$, $n^{N21}+n^{N22}$, and $n^{N31}+n^{N32}$ are each preferably 1 or 2. A combination of $n^{N11}=1$ and $n^{N12}=0$, a combination of $n^{N11}=2$ and $n^{N12}=0$, a combination of $n^{N11}=1$ and $n^{N12}=1$, a combination of $n^{N11}=2$ and $n^{N122}=1$, a combination of $n^{N21}=1$ and $n^{N22}=0$, a combination of $n^{N21}=2$ and $n^{N22}=0$, a combination of $n^{N31}=1$ and $n^{N32}=0$, and a combination of $n^{N31}=2$ and $n^{N32}=0$ are preferred.

A preferred lower limit of the content of the compound represented by formula (N-1) relative to the total mass of the composition in the present embodiment is 1% by mass or more, 10% by mass or more, 20% by mass or more, 30% by mass or more, 40% by mass or more, 50% by mass or more, 55% by mass or more, 60% by mass or more, 65% by mass or more, 70% by mass or more, 75% by mass or more, and 80% by mass or more. A preferred upper limit of the content is 95% by mass or less, 85% by mass or less, 75% by mass or less, 65% by mass or less, 55% by mass or less, 45% by mass or less, 35% by mass or less, 25% by mass or less, and 20% by mass or less.

A preferred lower limit of the content of the compound represented by formula (N-2) relative to the total mass of the composition in the present embodiment is 1% by mass or more, 10% by mass or more, 20% by mass or more, 30% by mass or more, 40% by mass or more, 50% by mass or more, 55% by mass or more, 60% by mass or more, 65% by mass or more, 70% by mass or more, 75% by mass or more, and 80% by mass or more. A preferred upper limit of the content is 95% by mass or less, 85% by mass or less, 75% by mass or less, 65% by mass or less, 55% by mass or less, 45% by mass or less, 35% by mass or less, 25% by mass or less, and 20% by mass or less.

A preferred lower limit of the content of the compound represented by formula (N-3) relative to the total mass of the composition in the present embodiment is 1% by mass or more, 10% by mass or more, 20% by mass or more, 30% by mass or more, 40% by mass or more, 50% by mass or more, 55% by mass or more, 60% by mass or more, 65% by mass or more, 70% by mass or more, 75% by mass or more, and 80% by mass or more. A preferred upper limit of the content is 95% by mass or less, 85% by mass or less, 75% by mass or less, 65% by mass or less, 55% by mass or less, 45% by mass or less, 35% by mass or less, 25% by mass or less, and 20% by mass or less.

When it is necessary that the response speed of the composition in the present embodiment be high while the viscosity of the composition is kept low, it is preferable that the lower limit is low and the upper limit is low. When it is necessary that the temperature stability of the composition in the present embodiment be high while the Tni of the composition is kept high, it is preferable that the lower limit is low and the upper limit is low. When there is a need for high dielectric anisotropy in order to keep driving voltage low, it is preferable that the lower limit is high and the upper limit is high.

Examples of the compound represented by general formula (N-1) include a group of compounds represented by general formulas (N-1a) to (N-1g) below.

[Chem. 32]

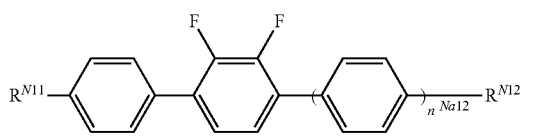
(N-1a)

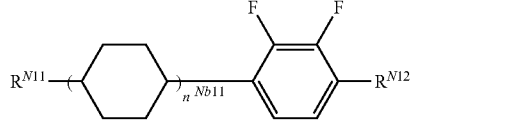
(N-1b)

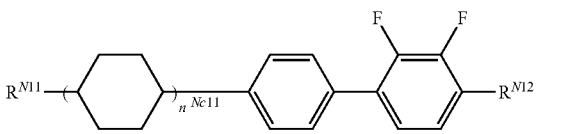
(N-1c)

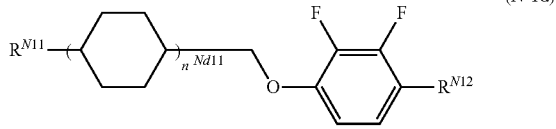
(N-1d)

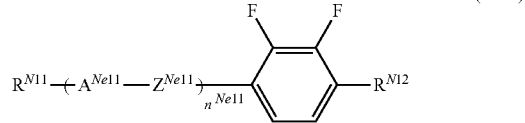
(N-1e)

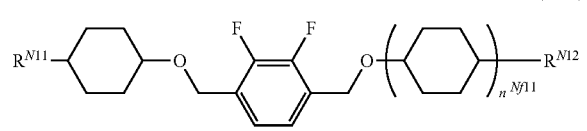
(N-1f)

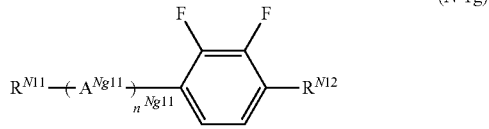
(N-1g)

(wherein $R^{N11}$ and $R^{N12}$ have the same meanings as $R^{N11}$ and $R^{N12}$ in general formula (N-1); $n^{Na11}$ represents 0 or 1; $n^{Nb11}$ represents 0 or 1; $n^{Nc11}$ represents 0 or 1; $n^{Nd11}$ represents or 1; $n^{Ne11}$ represents 1 or 2; $n^{Nf11}$ represents 1 or 2; Ng represents 1 or 2; each $A^{Ne11}$ group represents a trans-1,4-cyclohexylene group or a 1,4-phenylene group; each $A^{Ng11}$ group represents a trans-1,4-cyclohexylene group, a 1,4-cyclohexenylene group, or a 1,4-phenylene group, provided that at least one $A^{Ng11}$ group represents a 1,4-cyclohexenylene group; and each $Z^{Ne11}$ group represents a single bond or ethylene, provided that at least one $Z^{Ne11}$ group represents ethylene.)

More specifically, the compound represented by general formula (N-1) is preferably a compound selected from a group of compounds represented by general formulas (N-1-1) to (N-1-21).

The compound represented by general formula (N-1-1) is the following compound.

[Chem. 33]

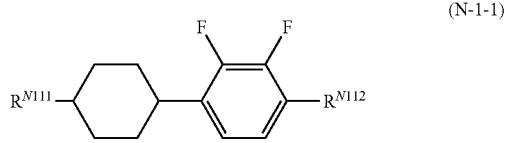

(N-1-1)

(wherein $R^{N111}$ and $R^{N112}$ each independently have the same meanings as $R^{N11}$ and $R^{N12}$ in general formula (N-1).)

$R^{N111}$ is preferably an alkyl group having 1 to 5 carbon atoms or an alkenyl group having 2 to 5 carbon atoms and more preferably a propyl group, a pentyl group, or a vinyl group. $R^{N112}$ is preferably an alkyl group having 1 to 5 carbon atoms, an alkenyl group having 4 to 5 carbon atoms, or an alkoxy group having 1 to 4 carbon atoms and more preferably an ethoxy group or a butoxy group.

[Chem. 34]

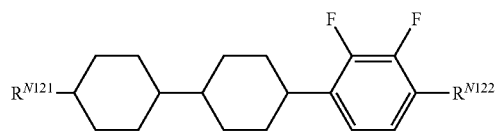

(N-1-2)

(wherein $R^{N121}$ and $R^{N122}$ each independently have the same meanings as $R^{N11}$ and $R^{N12}$ in general formula (N-1).)

[Chem. 35]

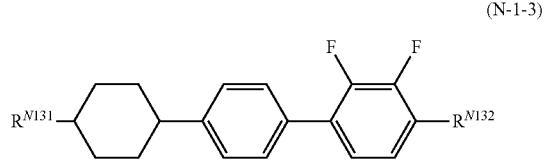

(N-1-3)

(wherein $R^{N131}$ and $R^{N132}$ each independently have the same meanings as $R^{N11}$ and $R^{N12}$ in general formula (N-1).)

[Chem. 36]

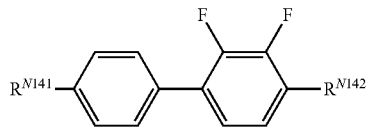

(N-1-4)

(wherein $R^{N141}$ and $R^{N142}$ each independently have the same meanings as $R^{N11}$ and $R^{N12}$ in general formula (N-1).)

[Chem. 37]

(N-1-5)

(wherein $R^{N151}$ and $R^{N152}$ each independently have the same meanings as $R^{N11}$ and $R^{N12}$ in general formula (N-1).)

The compound represented by general formula (N-1-10) is the following compound.

[Chem. 38]

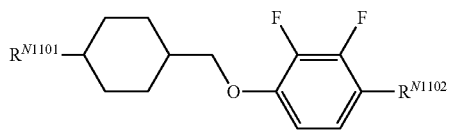

(N-1-10)

(wherein $R^{N1101}$ and $R^{N1102}$ each independently have the same meanings as $R^{N11}$ and $R^{N12}$ in general formula (N-1).)

[Chem. 39]

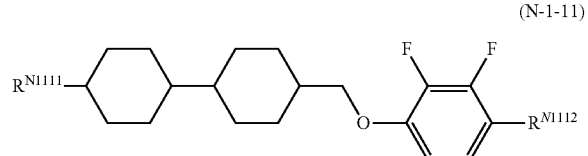

(N-1-11)

(wherein $R^{N1111}$ and $R^{N1112}$ each independently have the same meanings as $R^{N11}$ and $R^{N12}$ in general formula (N-1).)

[Chem. 40]

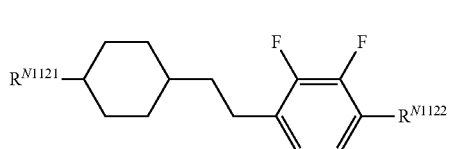

(N-1-12)

(wherein $R^{N1121}$ and $R^{N1122}$ each independently have the same meanings as $R^{N11}$ and $R^{N12}$ in general formula (N-1).)

[Chem. 41]

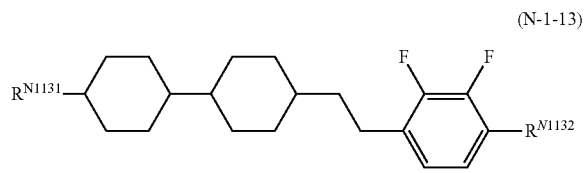

(N-1-13)

(wherein $R^{N1131}$ and $R^{N1132}$ each independently have the same meanings as $R^{N11}$ and $R^{N12}$ in general formula (N-1).)

[Chem. 42]

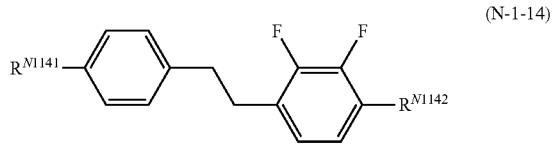

(N-1-14)

(wherein $R^{N1141}$ and $R^{N1142}$ each independently have the same meanings as $R^{N11}$ and $R^{N12}$ in general formula (N-1).)

[Chem. 43]

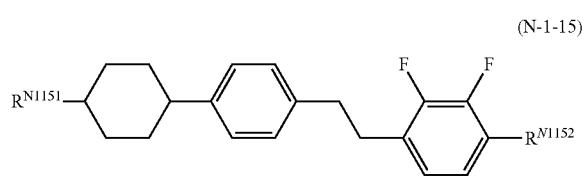

(N-1-15)

(wherein $R^{N111}$ and $R^{N1152}$ each independently have the same meanings as $R^{N11}$ and $R^{N12}$ in general formula (N-1).)

[Chem. 44]

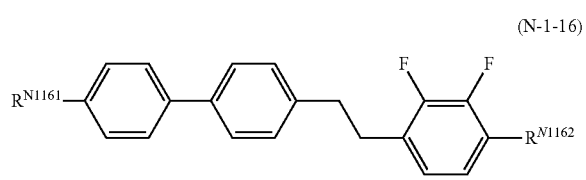

(N-1-16)

(wherein $R^{N1161}$ and $R^{N1162}$ each independently have the same meanings as $R^{N11}$ and $R^{N12}$ in general formula (N-1).)

[Chem. 45]

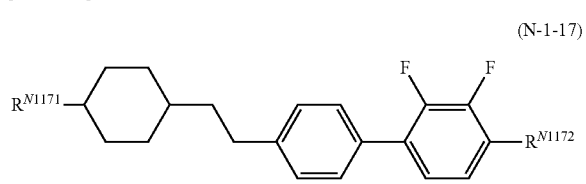

(N-1-17)

(wherein $R^{N1171}$ and $R^{N1172}$ each independently have the same meanings as $R^{N11}$ and $R^{N12}$ in general formula (N-1).)

[Chem. 47]

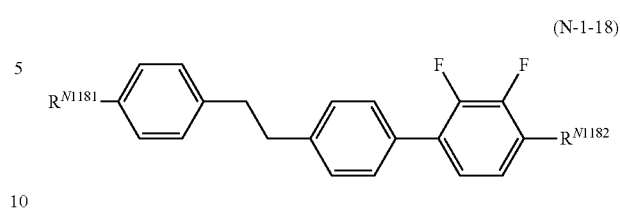

(N-1-18)

(wherein $R^{N1181}$ and $R^{N1182}$ each independently have the same meanings as $R^{N11}$ and $R^{N12}$ in general formula (N-1).)

[Chem. 47]

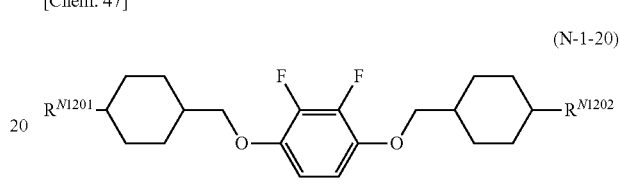

(N-1-20)

(wherein $R^{N1201}$ and $R^{N1202}$ each independently have the same meanings as $R^{N11}$ and $R^{N12}$ in general formula (N-1).)

[Chem. 48]

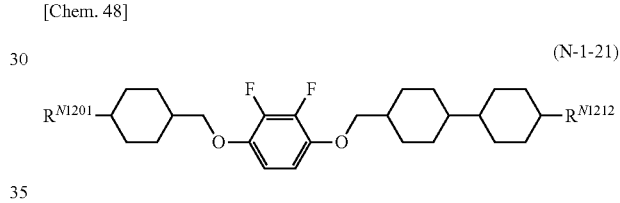

(N-1-21)

(wherein $R^{N1211}$ and $R^{N1212}$ each independently have the same meanings as $R^{N11}$ and $R^{N12}$ in general formula (N-1).)

The compounds represented by general formula (N-1) to general formula (N-3) can each be used alone or can be used in combination of two or more. No particular limitation is imposed on the types of compounds to be combined. Compounds are appropriately combined and used according to the required properties such as low-temperature solubility, transition temperature, electrical reliability, and birefringence. In one embodiment, the number of types of compounds used is, for example, one, two, three, four, or five or more.

When importance is placed on improvement in $\Delta\varepsilon$, it is preferable to set the content to be higher. When importance is placed on low-temperature solubility, setting the content to be higher is highly effective. When importance is placed on $T_{NI}$, setting the content to be lower is highly effective. To improve droplet stains and image-sticking characteristics, it is preferable to set the content within an intermediate range.

A preferred lower limit of the content of the compounds represented by general formula (N-1) to general formula (N-3) relative to the total mass of the composition in the present embodiment is 5% by mass or more, 10% by mass or more, 13% by mass or more, 15% by mass or more, 17% by mass or more, 20% by mass or more, 23% by mass or more, 25% by mass or more, 27% by mass or more, 30% by mass or more, 33% by mass or more, and 35% by mass or more. A preferred upper limit of the content relative to the total mass of the composition in the present embodiment is 50% by mass or less, 40% by mass or less, 38% by mass or less, 35% by mass or less, 33% by mass or less, 30% by mass or less, 28% by mass or less, 25% by mass or less, 23% by mass or less, 20% by mass or less, 18% by mass or less, 15% by mass or less, 13% by mass or less, 10% by mass or less, 8% by mass or less, 7% by mass or less, 6% by mass or less, 5% by mass or less, and 3% by mass or less.

The compound represented by general formula (N-1-1) is preferably a compound selected from a group of compounds represented by formula (N-1-1.1) to formula (N-1-1.22), more preferably one of compounds represented by formulas (N-1-1.1) to (N-1-1.4), and still more preferably one of compounds represented by formula (N-1-1.1) and formula (N-1-1.3).

[Chem. 49]

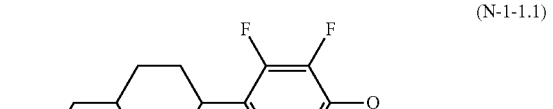
(N-1-1.1)

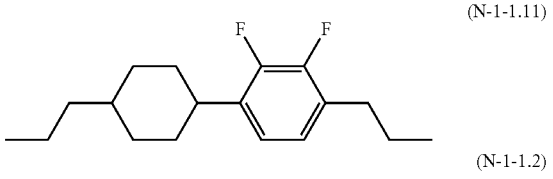
(N-1-1.11)

(N-1-1.2)

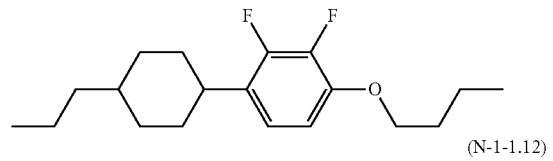
(N-1-1.12)

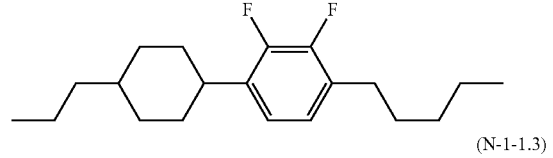
(N-1-1.3)

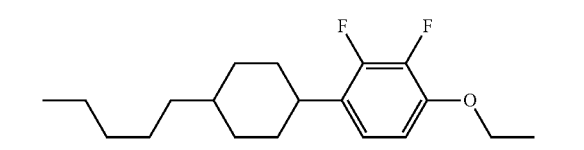
(N-1-1.13)

(N-1-1.4)

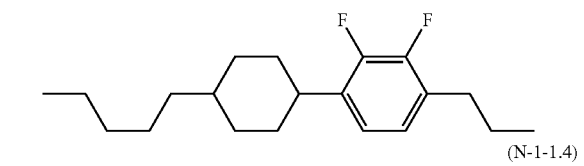
(N-1-1.14)

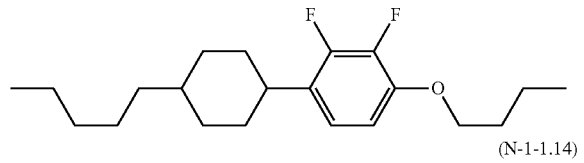

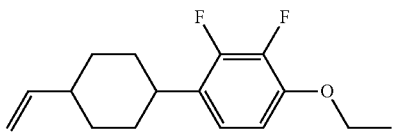
(N-1-1.20)

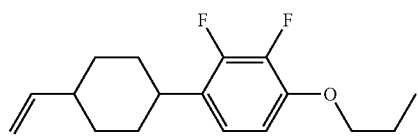
(N-1-1.21)

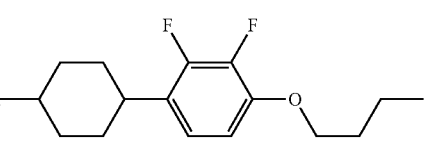
(N-1-1.22)

The compounds represented by formulas (N-1-1.1) to (N-1-1.22) can each be used alone or can be used in combination. A preferred lower limit of the content of one of these compounds that is used alone or a combination of any of these compounds relative to the total mass of the composition in the present embodiment is 5% by mass or more, and a preferred upper limit relative to the total mass of the composition in the present embodiment is 50% by mass or less.

The liquid crystal composition may contain, as a non-polymerizable liquid crystal compound, a nonpolar liquid crystal compound having a dielectric anisotropy of about 0. Examples of the nonpolar liquid crystal compound include a compound represented by general formula (LC6) below.

[Chem. 50]

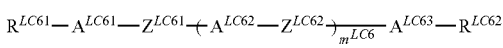
(LC6)

(wherein $R^{LC61}$ and $R^{LC62}$ each independently represent an alkyl group having 1 to 15 carbon atoms, one or two or more —$CH_2$— groups in the alkyl group being optionally replaced by —O—, —CH=CH—, —CO—, —OCO—, —COO—, or —C≡C—, provided that no oxygen atoms are directly adjacent to each other, one or two or more hydrogen atoms in the alkyl group being optionally replaced by halogen; $A^{LC61}$ to $A^{LC63}$ each independently represent any of the following:

[Chem. 51]

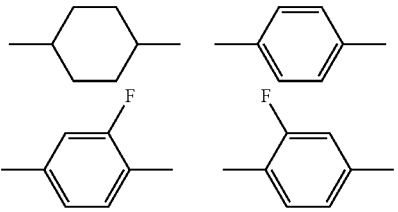

(in these structures, one or two or more —$CH_2CH_2$— groups in the cyclohexylene group are optionally replaced by —CH=CH—, —$CF_2O$—, or —$OCF_2$—, and one or two or more CH groups in the 1,4-phenylene group are optionally replaced by a nitrogen atom); $Z^{LC61}$ and $Z^{LC62}$ each independently represent a single bond, —CH=CH—, —C≡C—, —CH$_2$CH$_2$—, —(CH$_2$)$_4$—, —COO—, —OCH$_2$—, —CH$_2$O—, —OCF$_2$—, or —CF$_2$O—; and $m^{Lc6}$ represents 0 to 3. However, compounds represented by general formula (LC1) to general formula (LC5) and general formula (i) are excluded.)

$R^{LC61}$ and $R^{LC62}$ each independently represent preferably an alkyl group having 1 to 7 carbon atoms, an alkoxy group having 1 to 7 carbon atoms, or an alkenyl group having 2 to 7 carbon atoms, the alkenyl group representing most preferably any of the following structures:

[Chem. 52]

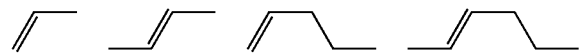

(wherein the right end of each structure is bonded to a ring structure);

$A^{LC61}$ to $A^{LC63}$ each independently represent preferably any of the following structures:

[Chem. 53]

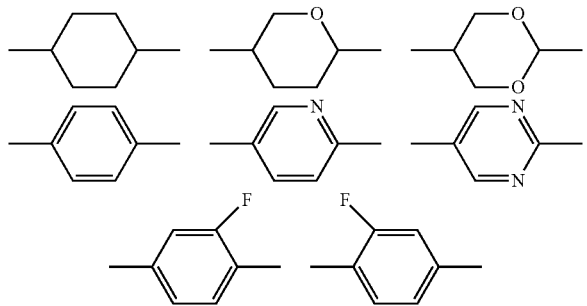

$Z^{LC61}$ and $Z^{LC62}$ each independently represent preferably a single bond, —CH$_2$CH$_2$—, —COO—, —OCH$_2$—, —CH$_2$O—, —OCF$_2$—, or —CF$_2$O—.

General formula (LC6) is more preferably one or two or more compounds selected from the group consisting of compounds represented by general formula (LC6-a) to general formula (LC6-m):

[Chem. 54]

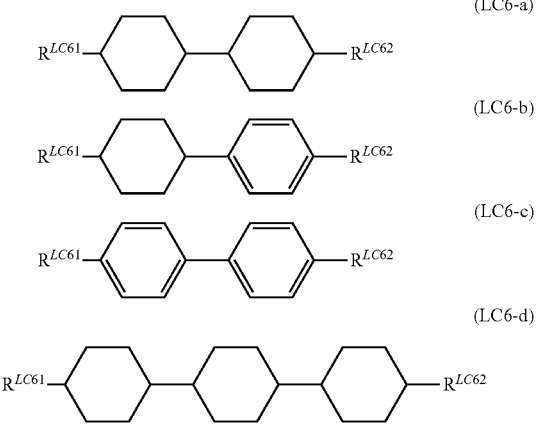

(LC6-a)

(LC6-b)

(LC6-c)

(LC6-d)

(LC6-e)

(LC6-f)

(LC6-g)

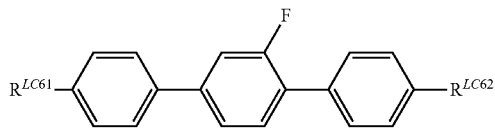

(LC6-h)

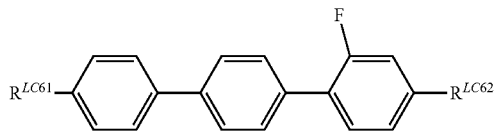

(LC6-i)

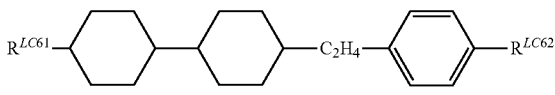

(LC6-j)

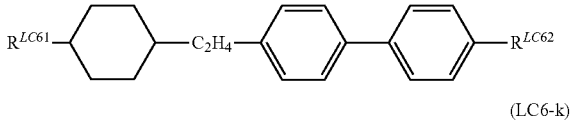

(LC6-k)

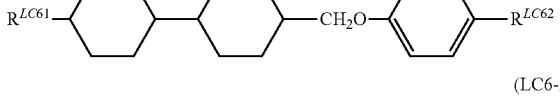

(LC6-l)

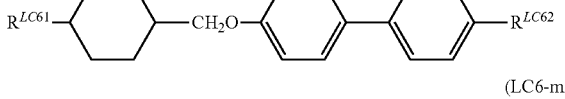

(LC6-m)

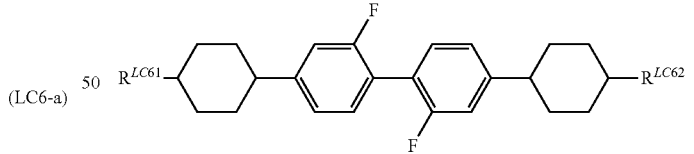

(wherein $R^{LC61}$ and $R^{LC62}$ each independently represent an alkyl group having 1 to 7 carbon atoms, an alkoxy group having 1 to 7 carbon atoms, an alkenyl group having 2 to 7 carbon atoms, or an alkenyloxy group having 2 to 7 carbon atoms).

The liquid crystal composition of the present invention may further contain another polymerizable compound different from the compound represented by general formula (i). The polymerizable compound may be a well-known polymerizable compound used for liquid crystal compositions. Examples of the polymerizable compound include a compound represented by general formula (P):

[Chem. 55]

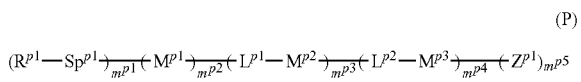
(P)

In formula (P), $Z^{p1}$ represents a fluorine atom, a cyano group, a hydrogen atom, an alkyl group which has 1 to 15 carbon atoms and in which any hydrogen atom is optionally replaced by a halogen atom, an alkoxy group which has 1 to 15 carbon atoms and in which any hydrogen atom is optionally replaced by a halogen atom, an alkenyl group which has 1 to 15 carbon atoms and in which any hydrogen atom is optionally replaced by a halogen atom, an alkenyloxy group which has 1 to 15 carbon atoms and in which any hydrogen atom is optionally replaced by a halogen atom, or -$Sp^{p2}$-$R^{p2}$;

$R^{p1}$ and $R^{p2}$ each independently represent any of the following formula (R-I) to formula (R-VIII):

[Chem. 56]

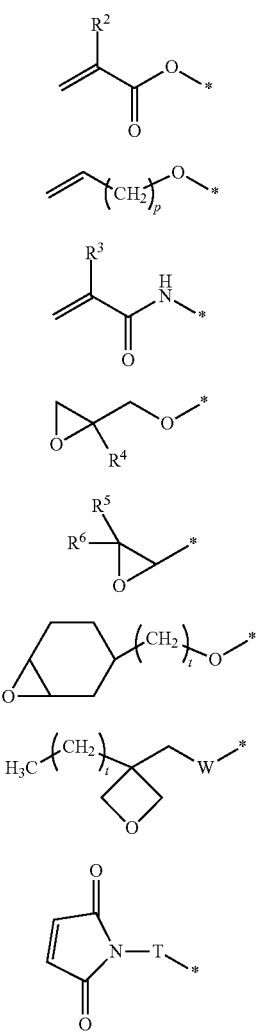

(R-I)
(R-II)
(R-III)
(R-IV)
(R-V)
(R-VI)
(R-VII)
(R-VIII)

(wherein
* represents a bond to $Sp^{p1}$;
$R^2$ to $R^6$ each independently represent a hydrogen atom, an alkyl group having 1 to 5 carbon atoms, or a halogenated alkyl group having 1 to 5 carbon atoms;

W represents a single bond, —O—, or a methylene group;
T represents a single bond or —COO—; and
p, t, and q each independently represent 0, 1, or 2);
$Sp^{p1}$ and $Sp^{p2}$ each represent a spacer group;
$L^{p1}$ and $L^{p2}$ each independently represent a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^a$—, —NR$^a$—CO—, —SCH$_2$—, —CH$_2$S—, —CH=CR$^a$—COO—, —CH=CR$^a$—OCO—, —COO—CR$^a$=CH—, —OCO—CR$^a$=CH—, —COO—CR$^a$=CH—COO—, —COO—CR$^a$=CH—OCO—, —OCO—CR$^a$=CH—COO—, —OCO—CR$^a$=CH—OCO—, —(CH$_2$)$_z$—C(=O)—O—, —(CH$_2$)$_z$—O—(C=O)—, —O—(C=O)—(CH$_2$)$_z$—, —(C=O)—O—(CH$_2$)$_z$—, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C— (wherein $R^a$ each independently represent a hydrogen atom or an alkyl group having 1 to 4 carbon atoms, and z represents an integer of 1 to 4);

$M^{p2}$ represents a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a 1,2,3,4-tetrahydronaphthalene-2,6-diyl group, a 1,3-dioxane-2,5-diyl group, or a single bond, $M^{p2}$ being unsubstituted or optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{p1}$;

$M^{p1}$ represents any of the following formulas (i-11) to (ix-11):

[Chem. 57]

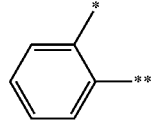
(i-11)

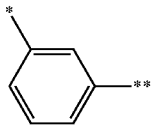
(ii-11)

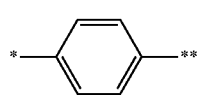
(iii-11)

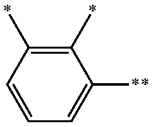
(iv-11)

(v-11)

(vi-11)

(vii-11)

(viii-11)

(ix-11)

(wherein * represents a bond to $Sp^{p1}$, and ** represents a bond to $L^{p1}$, $L^{p2}$, or $Z^{p1}$);

any hydrogen atom in $M^{p1}$ is optionally replaced by an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{p1}$;

$M^{p3}$ represents any of the following formulas (i-13) to (ix-13):

[Chem. 58]

(i-13)

(ii-13)

(iii-13)

(iv-13)

(v-13)

(vi-13)

(vii-13)

(viii-13)

(ix-13)

(wherein * represents a bond to $Z^{p1}$, and ** represents a bond to $L^{p2}$);

any hydrogen atom in $M^{p3}$ is optionally replaced by an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{p1}$;

$m^{p2}$ to $m^{p4}$ each independently represent 0, 1, 2, or 3;

$m^{p1}$ and $m^{p5}$ each independently represent 1, 2, or 3;

when a plurality of $Z^{p1}$ are present, they may be the same or different; when a plurality of $R^{p1}$ are present, they may be the same or different; when a plurality of $R^{p2}$ are present, they may be the same or different; when a plurality of $Sp^{p1}$ are present, they may be the same or different; when a plurality of $Sp^{p2}$ are present, they may be the same or different; when a plurality of $L^{p1}$ are present, they may be the same or different; and when a plurality of $M^{p2}$ are present, they may be the same or different.

When the liquid crystal composition in the present embodiment further contains the polymerizable compound represented by general formula (P) in addition to the compound (i), the pretilt angle of liquid crystal molecules can be preferably formed. Specific examples of the polymerizable compound represented by general formula (P) include (P-2-1) to (P-2-20).

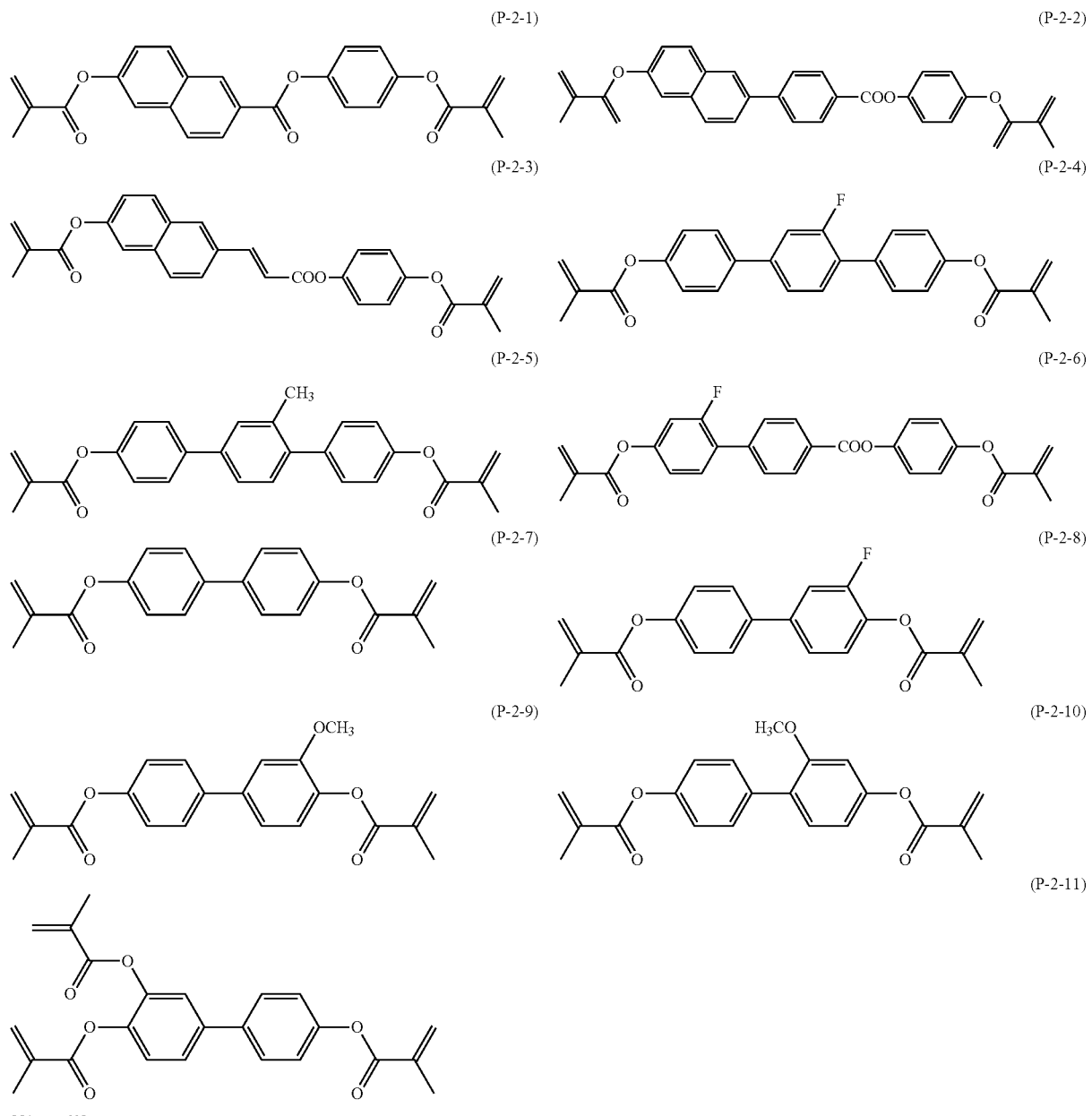

(P-2-16)

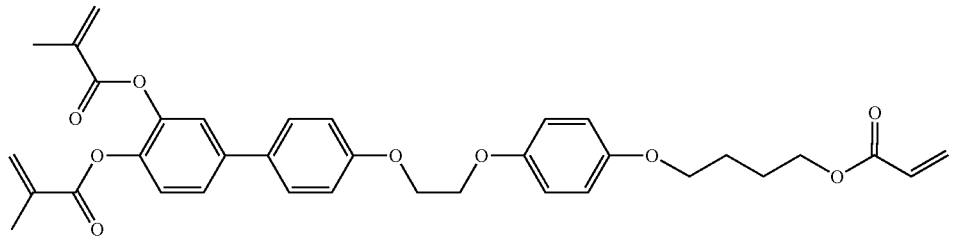

(P-2-17)

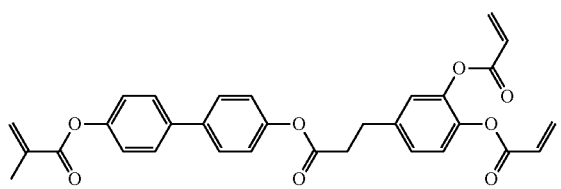

(P-2-18)

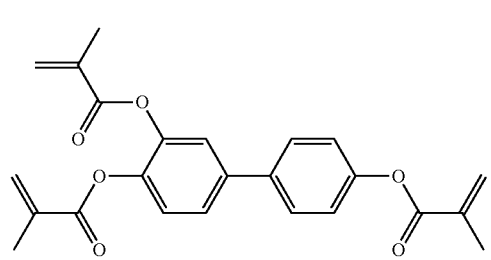

(P-2-19)

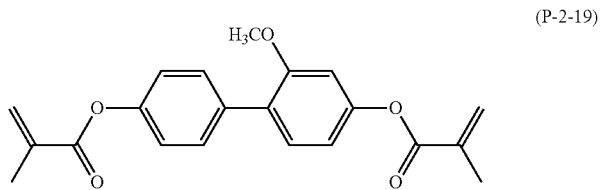

(P-2-20)

(Liquid Crystal Display Device)

The liquid crystal composition in the present embodiment is used for a liquid crystal display device. The liquid crystal display device may be an active matrix driving liquid crystal display device. The liquid crystal display device may be a PSA, PSVA, VA, IPS, FFS, or ECB liquid crystal display device and is preferably a PSA liquid crystal display device.

In the liquid crystal display device in the present embodiment, the liquid crystal composition containing the compound represented by general formula (i) is used. It is therefore unnecessary to provide an alignment film such as a polyimide alignment film on a liquid crystal layer 4 side of each of a first substrate 2 and a second substrate 3. Specifically, in the liquid crystal display device in the present embodiment, at least one of the two substrates may have a structure in which an alignment film such as a polyimide alignment film is not provided.

EXAMPLES

The present invention will next be described more specifically by way of Examples, but the invention is not limited to these Examples.

Example 1

A reaction vessel equipped with a stirrer, a condenser, and a thermometer was charged with 20 g of 3-fluoro-4-nonylphenylboronic acid, 10.6 g of bromophenol, 17 g of potassium carbonate, 200 mg of tetrakis triphenylphosphine palladium, and 150 mL of ethanol, and the mixture was allowed to react at 90° C. for 5 hours. After completion of the reaction, the reaction vessel was cooled, and 300 mL of acetic acid ethyl ester was added. The organic layer was washed with water and then saturated saline, and the solvent was removed by evaporation. The residue was recrystallized from toluene to thereby obtain 18 g of a compound represented by (1).

[Chem. 61]

(1)

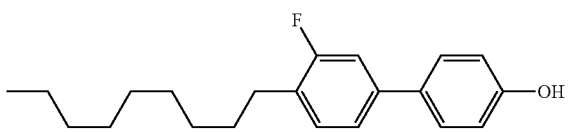

Next, a reaction vessel equipped with a stirrer, a dropping funnel, and a thermometer was charged with 18 g of compound (1) and 200 mL of dichloromethane, and a solution of 27 g of bromine in dichloromethane was slowly added dropwise at room temperature. After completion of the dropwise addition, the mixture was allowed to further react at room temperature for 2 hours. After completion of the reaction, 200 mL of 10% sodium sulfite was added. Then the organic layer was washed with water and then saturated saline, and the solvent was removed by evaporation. Then the residue was dissolved in toluene and purified on a silica gel column to obtain 22 g of a compound represented by formula (2).

[Chem. 62]

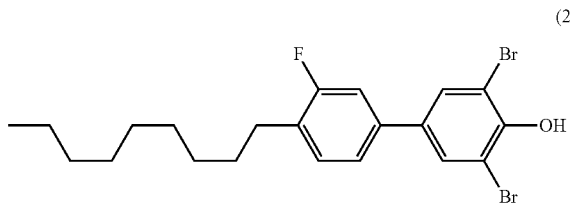

(2)

Next, a reaction vessel equipped with a stirrer, a condenser, and a thermometer was charged with 22 g of the above compound (2), 15 g of triphenylphosphine, 5.6 g of glycerol 1,2-carbonate, and 100 mL of N,N-dimethylformamide, and cooled to 10° C. or lower. Then 12 g of diisopropyl diazocarboxylate was slowly added dropwise. After completion of the dropwise addition, the reaction vessel was returned to room temperature, and the mixture was allowed to react for 3 hours. After completion of the reaction, water was slowly added, and the mixture was washed with 100 mL of dichloromethane, water, and saturated saline. The solvent was removed by evaporation, and the residue was purified on a silica gel column to obtain 23.5 g of a compound represented by (3).

[Chem. 63]

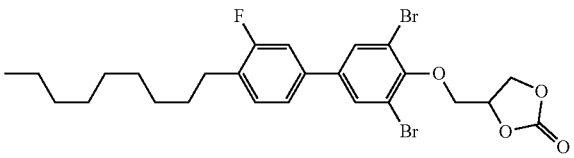

(3)

Then a reaction vessel equipped with a stirrer, a condenser, and a thermometer was charged with 23.5 g of the above compound (3), 1 g of copper iodide, 2.5 g of tetrakis triphenylphosphine palladium, 150 mL of tetrahydrofuran, and 20 mL of water, and the mixture was stirred at room temperature. Next, 30 mL of ethanolamine was added, and the reaction vessel was heated to 65° C. Then 7.0 g of propargyl alcohol was slowly added dropwise. After completion of the dropwise addition, the mixture was allowed to react for 1 hour. After completion of the reaction, the reaction vessel was cooled, and 100 mL of toluene was added. The organic layer was washed with a saturated ammonium chloride solution, water, and saturated saline, and the solvent was removed by evaporation. Then 200 mL of tetrahydrofuran and 20 mL of ethanol were added, and the resulting mixture was placed in an autoclave. 2 g of 5% palladium on carbon (wet) was added, and the mixture was subjected to catalytic hydrogen reduction at a hydrogen pressure of 0.5 kPa. After completion of the reaction, the palladium on carbon was removed by filtration, and the product was purified on a silica gel column to obtain 16 g of a compound represented by formula (4).

[Chem. 64]

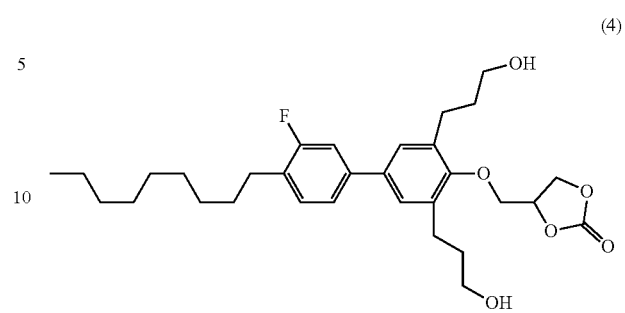

(4)

A reaction vessel equipped with a stirrer, a dropping funnel, and a thermometer was charged with 16 g of the above compound (4), 6.2 g of methacrylic acid, 200 mg of dimethylaminopyridine, and 100 mL of dichloromethane and cooled to 10° C. or lower. Then 6.7 g of diisopropylcarbodiimide was slowly added dropwise. After completion of the dropwise addition, the reaction vessel was returned to room temperature, and the mixture was allowed to react for 3 hours. After completion of the reaction, water was slowly added, and the mixture was washed with 100 mL of dichloromethane, water, and saturated saline. The solvent was removed by evaporation, and the residue was purified on a silica gel column to obtain 12 g of an oily target compound represented by (P-1-22).

[Chem. 65]

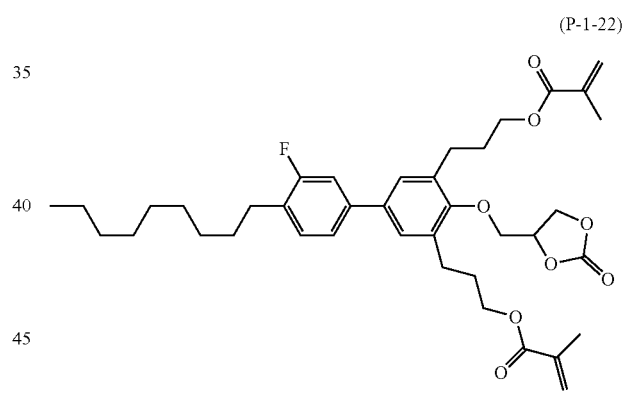

(P-1-22)

(Values of Physical Properties)

$^1$H-NMR (solvent: deuterated chloroform): δ: 0.88 (t, 3H), 1.26 (m, 12H), 1.52-1.59 (m, 2H), 1.87-1.92 (m, 4H), 1.97 (s, 3H), 2.63 (t, 6H), 3.98-4.03 (m, 2H), 4.18-4.26 (m, 4H), 4.68-4.70 (m, 1H), 6.38 (d, 2H), 6.48 (d, 2H), 7.15 (d, 1H), 7.33-7.37 (m, 1H), 7.52 (d, 1H), 7.72 (s, 2H)

$^{13}$C-NMR (solvent: deuterated chloroform): δ: 14.1, 17.9, 22.7, 26.6, 27.9, 28.9, 29.6, 30.2, 31.2, 62.5, 65.2, 68.7, 71.5, 114.7, 122.3, 123.5, 127.8, 128.4, 135.5, 138.6, 146.7, 151.7, 155.3, 155.6, 161.0

Example 2

A reaction vessel equipped with a stirrer, a condenser, and a thermometer was charged with 30 g of 3-fluoro-4'-heptyl-[1,1'-biphenyl]-4-yl)boronic acid, 20 g of 4-bromo-2-(3-hydroxypropyl)phenol, 18 g of potassium carbonate, 200 mg of tetrakis triphenylphosphine palladium, and 200 mL of ethanol, and the mixture was allowed to react at 90° C. for 5 hours. After completion of the reaction, the reaction vessel was cooled, and 300 mL of ethyl acetate and 100 mL of tetrahydrofuran were added. The organic layer was washed with water and then saturated saline, and the solvent was removed by evaporation. The residue was recrystallized from toluene to obtain 32 g of a compound represented by (5).

[Chem. 66]

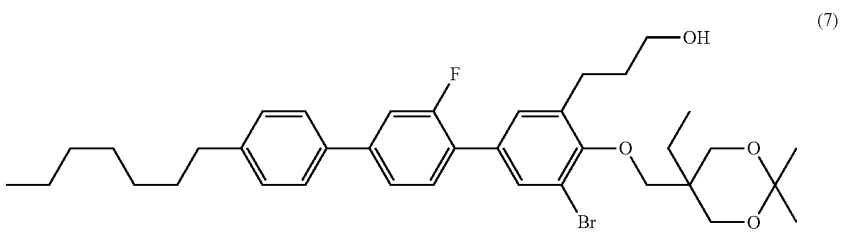

(5)

Next, a reaction vessel equipped with a stirrer, a dropping funnel, and a thermometer was charged with 32 g of compound (5), 1.5 g of diisopropylamine, and 150 mL of dichloromethane and cooled to 10° C. 30 mL of a solution of 13.5 g of N-bromosuccinimide in acetonitrile was slowly added dropwise. After completion of the dropwise addition and after completion of the reaction, 10% sodium hydrogen sulfite was added. The organic layer was washed with water and then saturated saline, and the solvent was removed by evaporation. Then the residue was purified on an alumina column to obtain 33 g of a compound represented by formula (6).

[Chem. 67]

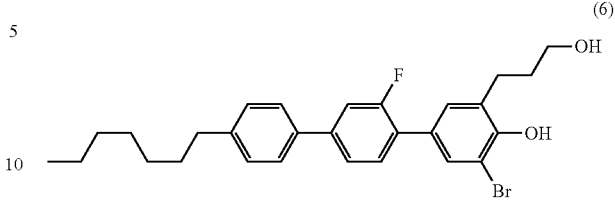

(6)

A reaction vessel equipped with a stirrer, a condenser, and a thermometer was charged with 33 g of compound (6), 14 g of potassium carbonate, 21.5 g of (5-ethyl-2,2'-dimethyl-1,3-dioxane-5-yl)methyl methanesulfonate, and 200 mL of N,N-dimethylformamide, and the mixture was allowed to react at 90° C. for 5 hours. After completion of the reaction, the reaction vessel was cooled, and 300 mL of ethyl acetate was added. The organic layer was washed with water and then saturated saline, and the solvent was removed by evaporation. Then the residue was dispersed in toluene, washed, and then purified on an alumina column to obtain 34.5 g of a compound represented by formula (7).

[Chem. 68]

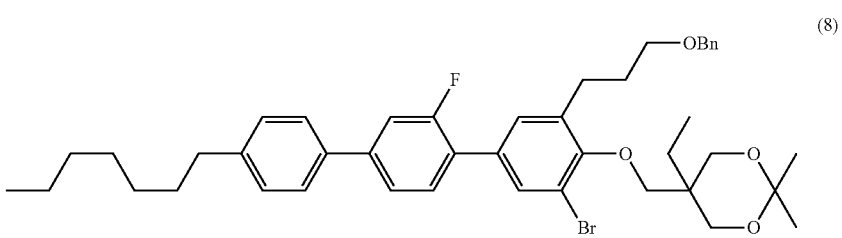

(7)

Then a reaction vessel equipped with a stirrer and a thermometer was charged with 34.5 g of the above compound (7), 8 g of triethylamine, and 100 mL of dichloromethane, and 11.8 g of benzyl bromide was slowly added dropwise at room temperature. After completion of the reaction, the reaction vessel was cooled, and 100 mL of tetrahydrofuran and 200 mL of ethyl acetate were added. The organic layer was washed with water and then saturated saline, and the solvent was removed by evaporation. Then the residue was dispersed in toluene to wash the residue and then purified on an alumina column to obtain 36 g of a target compound represented by formula (8).

[Chem. 69]

(8)

A reaction vessel equipped with a stirrer, a dropping funnel, and a thermometer was charged with 36 g of compound (8), 13.6 g of triisoproyl borate, and 250 mL of tetrahydrofuran and cooled to −70° C. While the temperature was maintained at −70° C., 40 mL of a 1.55 mol/L n-butyl-lithium hexane solution was slowly added dropwise, and the mixture was allowed to react. After completion of the reaction, 200 mL of a 10% ammonium chloride solution was slowly added, and then 100 mL of toluene was added. The organic layer was washed with water and then saturated saline. The organic layer was returned to the reaction mixture. Then 10 mL of 30% hydrogen peroxide water was added dropwise at room temperature, and the resulting mixture was allowed to further react under stirring for 3 hours. The reaction mixture was washed with 200 mL of water, and the organic layer was washed with 10% sodium sulfite, water, and saturated saline. The solvent was removed by evaporation. 200 mL of tetrahydrofuran and 20 mL of ethanol were added, and the mixture was placed in an autoclave. 2 g of 5% palladium on carbon (wet) was added, and the mixture was subjected to catalytic hydrogen reduction at a hydrogen pressure of 0.5 kPa. After completion of the reaction, the palladium on carbon was removed by filtration. Then the product was dispersed in toluene to wash the product and then purified on an alumina column to obtain 19 g of a compound represented by formula (9).

[Chem. 70]

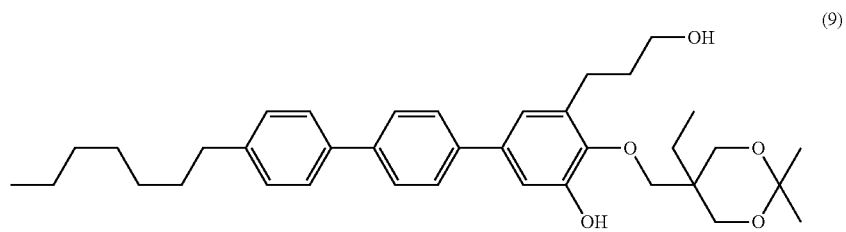

(9)

A reaction vessel equipped with a stirrer, a dropping funnel, and a thermometer was charged with 19 g of the above compound (9), 7.6 g of methacrylic acid, 800 mg of dimethylaminopyridine, and 100 mL of dichloromethane and cooled to 10° C. or lower. Then 10 g of diisopropyl-carbodiimide was slowly added dropwise. After completion of the dropwise addition, the reaction vessel was returned to room temperature, and the mixture was allowed to react for 3 hours. After completion of the reaction, water was slowly added, and the mixture was washed with 100 mL of dichloromethane, water, and saturated saline. The solvent was removed by evaporation, and the residue was dissolved in 100 mL of tetrahydrofuran. Then 20 mL of 2N hydrochloric acid was added at room temperature, and the mixture was stirred for 6 hours. After completion of the reaction, 200 mL of ethyl acetate was added. The mixture was washed with water and saturated saline, and the solvent was removed by evaporation. The concentrate was purified on a silica gel column using dichloromethane/ethyl acetate to obtain 17 g of a target compound represented by (P-1-23).

[Chem. 71]

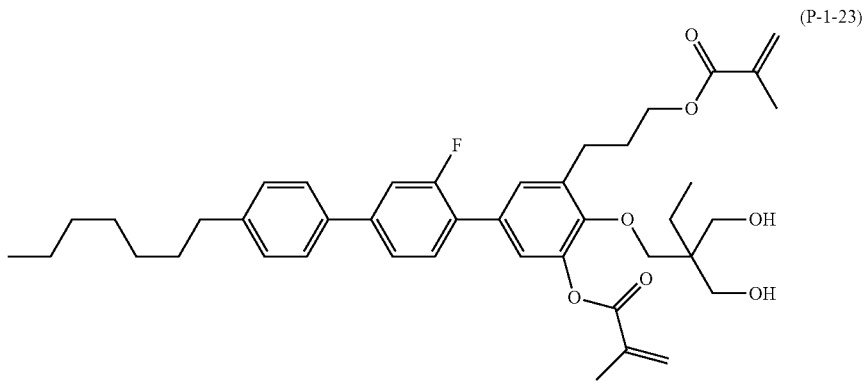

(P-1-23)

(Values of Physical Properties)
 Melting point 53° C.
 $^1$H-NMR (solvent: deuterated chloroform): δ: 0.83-0.88 (m, 6H), 1.27 (s, 8H), 1.63-1.69 (m, 4H), 1.91 (m, 2H), 1.97 (s, 6H), 2.63 (t, 4H), 3.39 (s, 4H), 3.80 (s, 4H), 3.94 (s, 4H), 4.18-4.22 (m, 4H), 5.60 (s, 1H), 6.14 (m, 3H), 7.02 (m, 1H), 7.28 (d, 2H), 7.38 (s, 1H), 7.61-7.64 (m, 3H), 7.65 (d, 1H), 7.94 (m, 1H)
 $^{13}$C-NMR (solvent: deuterated chloroform): δ: 14.1, 17.9, 22.7, 25.5, 26.3, 27.9, 29.3, 30.1, 31.2, 35.5, 43.0, 63.3, 65.2, 122.7, 125.3, 127.1, 128.0, 129.7, 130.5, 135.0, 139.0, 158.3, 166.0

Example 3

A reaction vessel equipped with a stirrer, a dropping funnel, and a thermometer was charged with 10 g of compound (P-1-23) in Example 2 and 100 mL of dichloromethane and cooled to 10° C. or lower. Then 2 g of ethyl chloroformate was slowly added dropwise. After completion of the dropwise addition, the mixture was stirred for 30 minutes. Then 2 g of triethylamine was added dropwise. After completion of the reaction, the organic layer was washed with water and then saturated saline, and the solvent was removed by evaporation. Then the residue was purified on a silica gel column to obtain 9 g of a target compound represented by compound (P-1-24).

[Chem. 72]

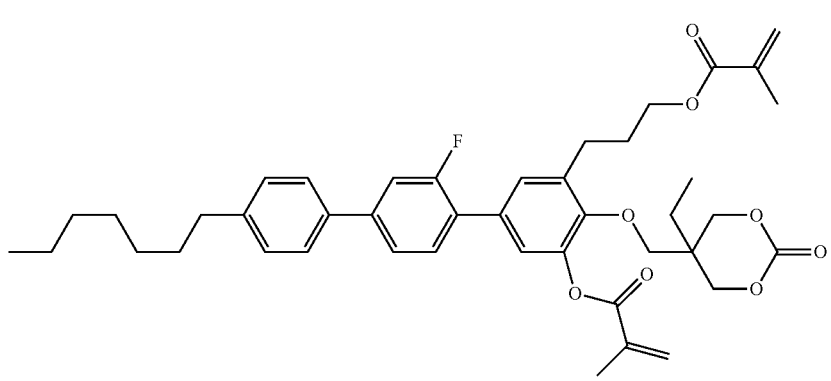

(P-1-24)

Melting point 75° C.
 $^1$H-NMR (solvent: deuterated chloroform): δ: 0.83-0.88 (m, 6H), 1.27 (s, 8H), 1.63-1.69 (m, 4H), 1.91 (m, 2H), 1.97 (s, 6H), 2.63 (t, 4H), 3.80 (s, 2H), 3.89 (d, 4H), 4.11-4.20 (m, 2H), 5.60 (s, 1H), 6.14 (m, 3H), 7.02 (m, 1H), 7.28 (d, 2H), 7.38 (s, 1H), 7.61-7.64 (m, 3H), 7.65 (d, 1H), 7.94 (m, 1H)
 $^{13}$C-NMR (solvent: deuterated chloroform): δ: 14.1, 17.9, 22.7, 25.5, 26.3, 27.9, 29.3, 30.1, 31.2, 35.5, 62.5, 70.7, 77.6, 122.7, 125.3, 127.1, 128.0, 129.7, 130.5, 135.0, 139.5, 152.5, 158.3, 166.0

Example 4

A reaction vessel equipped with a stirrer, a condenser, and a thermometer was charged with 24 g of 4-benzyloxyphenylboronic acid, 17 g of 4-bromophenol, 27 g of potassium carbonate, 150 mg of tetrakis triphenylphosphine palladium, and 200 mL of ethanol, and the mixture was allowed to react at 90° C. for 5 hours. After completion of the reaction, the reaction vessel was cooled, and 300 mL of ethyl acetate and 100 mL of tetrahydrofuran were added. The organic layer was washed with water and then saturated saline, and the solvent was removed by evaporation. Then the residue was dispersed in toluene to wash the residue to obtain 24 g of a compound represented by (10).

[Chem. 73]

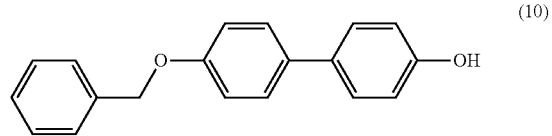

(10)

Next, 24 g of compound (10) was dissolved in 250 mL of dichloromethane, and a solution of 15 g of bromine in dichloromethane was added dropwise at room temperature. After completion of the dropwise addition, the mixture was allowed to react at room temperature for 2 hours. After completion of the reaction, 250 mL of 10% sodium sulfite was added. The organic layer was washed with water and then saturated saline, and the solvent was removed by evaporation. Then the residue was dissolved in toluene and purified on a silica gel column to obtain 33 g of a compound represented by formula (11).

[Chem. 74]

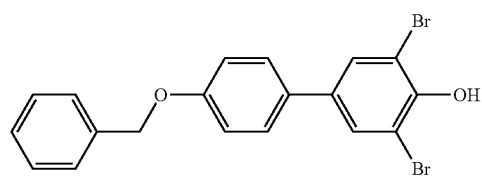

(11)

A reaction vessel equipped with a stirrer, a condenser, and a thermometer was charged with 33 g of the above compound (11), 8.9 g of tetrahydropyran-4-methanol, 24 g of triphenylphosphine, and 150 mL of tetrahydrofuran and cooled to 10° C. or lower. Then 18.5 g of diisopropyl diazocarboxylate was slowly added dropwise. After completion of the dropwise addition, the reaction vessel was returned to room temperature, and the mixture was allowed to react for 3 hours. After completion of the reaction, water was slowly added, and the mixture was washed with 100 mL of dichloromethane, water, and saturated saline. The solvent was removed by evaporation, and the residue was purified on a silica gel column to obtain 34.5 g of a compound represented by (3).

[Chem. 75]

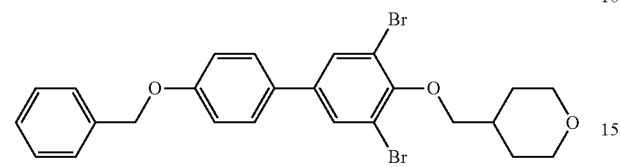

(12)

Then a reaction vessel equipped with a stirrer, a condenser, and a thermometer was charged with 34.5 g of the above compound (12), 1.2 g of copper iodide, 3.2 of tetrakis triphenylphosphine palladium, 150 mL of tetrahydrofuran, and 20 mL of water, and the mixture was stirred at room temperature. Then 40 mL of ethanolamine was added, and the reaction vessel was heated to 65° C. Then 11 g of 2-(prop-2-en-1-yloxy)tetrahydro-2H-pyran was slowly added dropwise. After completion of the dropwise addition, the mixture was allowed to react for 1 hour. After completion of the reaction, the reaction vessel was cooled, and 100 mL of toluene was added. The organic layer was washed with a saturated ammonium chloride solution, water, and saturated saline, and the solvent was removed by evaporation. Then 300 mL of tetrahydrofuran and 30 mL of ethanol were added, and the mixture was placed in an autoclave. 4 g of 5% palladium on carbon (wet) was added, and the mixture was subjected to catalytic hydrogen reduction at a hydrogen pressure of 0.5 kPa. After completion of the reaction, palladium on carbon was removed by filtration, and the product was purified on a silica gel column to obtain 28 g of a compound represented by formula (13).

[Chem. 76]

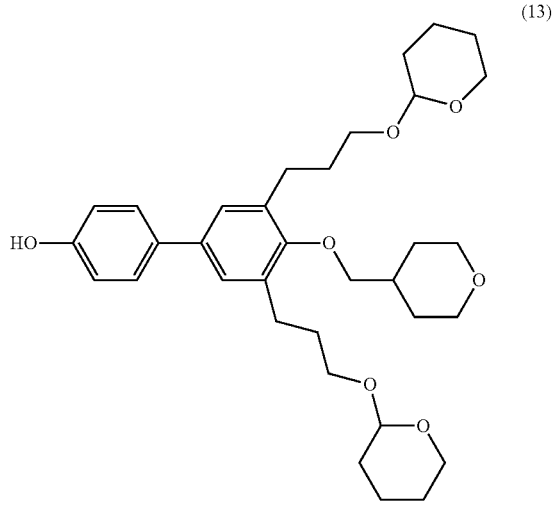

(13)

A reaction vessel equipped with a stirrer, a condenser, and a thermometer was charged with 28 g of compound (13), 14 g of 3-(4-(butoxymethyl)phenyl)propionic acid, 300 mg of dimethylaminopyridine, and 100 mL of dichloromethane and cooled to 10° C. or lower. Then 7.4 g of diisopropyl-carbodiimide was slowly added dropwise. After completion of the dropwise addition, the reaction vessel was returned to room temperature, and the mixture was allowed to react for 3 hours. After completion of the reaction, water was slowly added, and the mixture was washed with 100 mL of dichloromethane, water, and saturated saline. The solvent was removed by evaporation, and the residue was dissolved in 100 mL of tetrahydrofuran. 20 mL of 2N hydrochloric acid was added at room temperature, and the mixture was stirred for 6 hours. After completion of the reaction, 200 mL of ethyl acetate was added, and the mixture was washed with water and saturated saline. Then the solvent was removed by evaporation. The concentrate was purified on a silica gel column using dichloromethane/ethyl acetate to obtain 27 g of a compound represented by (14).

[Chem. 77]

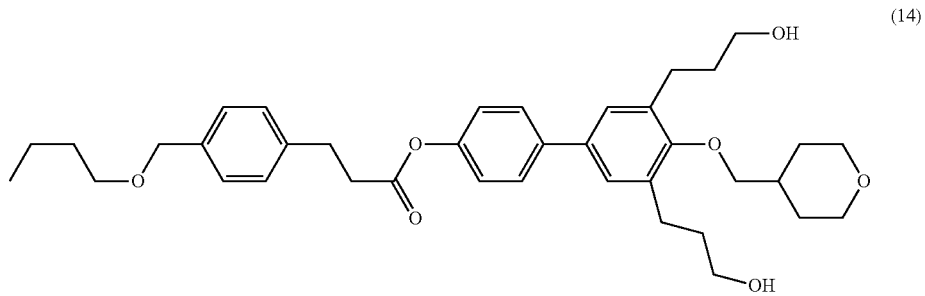

(14)

A reaction vessel equipped with a stirrer, a dropping funnel, and a thermometer was charged with 27 g of the above compound (14), 5.2 g of triethylamine, and 80 mL of dichloromethane and cooled to 10° C. or lower. Then 4.7 g of acrylic acid chloride was slowly added dropwise. After completion of the dropwise addition, the reaction vessel was returned to room temperature, and the mixture was allowed to react for 3 hours. After completion of the reaction, water was slowly added, and the mixture was washed with 100 mL of dichloromethane, water, and saturated saline. The solvent was removed by evaporation, and the residue was purified on a silica gel column using dichloromethane to obtain 17 g of a target compound represented by (P-1-25).

was washed with water and then saturated saline, and the solvent was removed by evaporation. Then the residue was transferred to a reaction vessel equipped with a stirrer, a dropping funnel, and a thermometer. 100 mL of dichloromethane was added, and the reaction vessel was cooled to 10° C. 15 mL of a solution of 9.2 g of N-bromosuccinimide in acetonitrile was slowly added dropwise. After completion of the dropwise addition and after completion of the reaction, 10% sodium hydrogen sulfite was added. The organic layer was washed with water and then saturated saline, and the solvent was removed by evaporation. Then the residue was purified on a silica gel column to obtain 13 g of a compound represented by formula (15).

[Chem. 78]

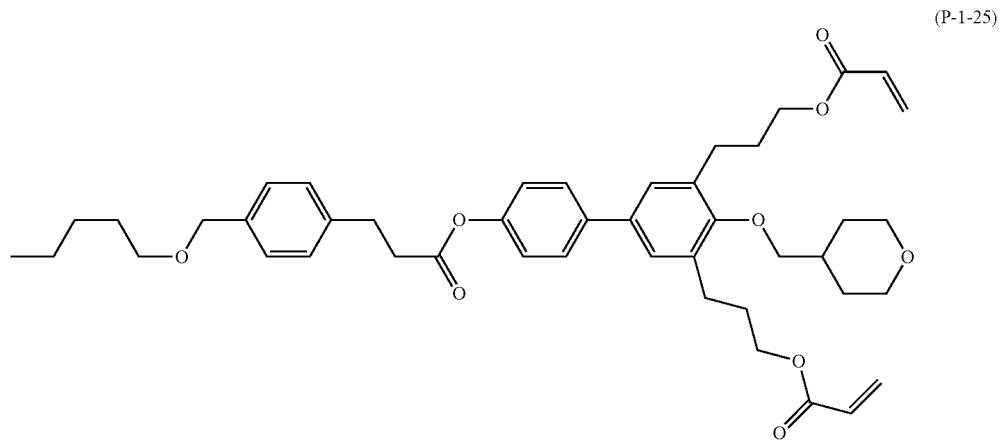

(P-1-25)

(Values of Physical Properties)

$^1$H-NMR (solvent: deuterated chloroform): δ: 0.88 (t, 3H), 1.28-1.34 (m, 6H), 1.48-1.54 (m, 4H), 1.83-1.86 (m, 2H), 2.10 (m, 1H), 2.65 (t, 4H), 2.73 (m, 2H), 2.82 (m, 2H), 3.35 (t, 2H), 3.55-3.65 (m, 4H), 3.70 (d, 2H), 4.18-4.20 (m, 4H), 4.80 (s, 2H), 5.83 (d, 2H), 6.12-6.13 (m, 2H), 6.41 (d, 2H), 7.08-7.18 (m, 6H), 7.74 (d, 4H)

$^{13}$C-NMR (solvent: deuterated chloroform): δ: 14.1, 22.7, 26.6, 28.1, 29.7, 30.6, 30.8, 34.5, 63.7, 64.9, 68.7, 73.0, 75.5, 122.1, 127.3, 127.6, 128.1, 129.1, 131.5, 133.7, 134.6, 150.2, 166.0

[Chem. 79]

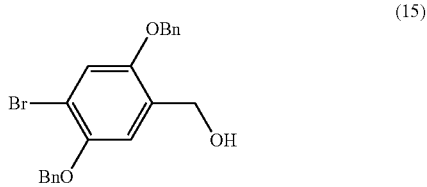

(15)

Example 5

A reaction vessel equipped with a stirrer, a dropping funnel, and a thermometer was charged with 900 mg of sodium borohydride and 10 mL of ethanol and cooled to 10° C. or lower. Then 30 ml of a solution of 15 g of 2,5-bis (benzyloxy)benzaldehyde in tetrahydrofuran was slowly added dropwise. After completion of the dropwise addition, the mixture was stirred for 1 hour, and 30 mL of 10% hydrochloric acid was slowly added. Then the mixture was extracted with 100 mL of ethyl acetate. The organic layer A reaction vessel equipped with a stirrer, a condenser, and a thermometer was charged with 14 g of the above compound (15), 11.5 g of 3-fluoro-4-(1-octyloxy)phenylboronic acid, 7 g of potassium carbonate, 100 mg of tetrakis triphenylphosphine palladium, and 100 mL of ethanol, and the mixture was allowed to react at 90° C. for 5 hours. After completion of the reaction, the reaction vessel was cooled, and 200 mL of acetic acid ethyl ester was added. The organic layer was washed with water and then saturated saline, and the solvent was removed by evaporation. The residue was dispersed in toluene to wash the residue to obtain 14 g of a compound represented by (16).

[Chem. 80]

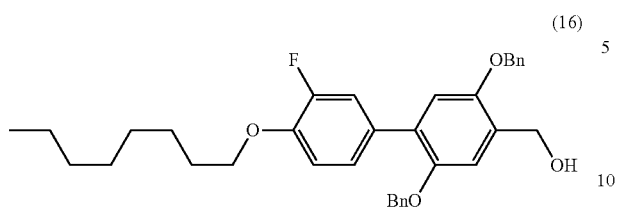

(16)

A reaction vessel equipped with a stirrer, a dropping funnel, and a thermometer was charged with 14 g of the above compound (16), 40 mg of TEMPO, 190 mg of potassium bromide, and 50 mL of dichloromethane and cooled to 10° C. or lower. Next, 10 mL of an aqueous solution of 2.2 g of sodium hypochlorite was slowly added dropwise. After completion of the dropwise addition, the mixture was allowed to react at room temperature for 2 hours under stirring. After completion of the reaction, 100 mL of a 10% sodium sulfite solution and 100 mL of dichloromethane were added. The organic layer was washed with water and then saturated saline, and the solvent was removed by evaporation to obtain 13 g of a compound represented by formula (17).

[Chem. 81]

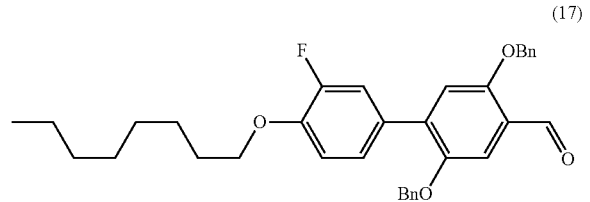

(17)

Next, a reaction vessel equipped with a stirrer, a dropping funnel, and a thermometer was charged with 13 g of the above compound (17) and 40 mL of dichloromethane and cooled to 10° C. or lower. Then 20 mL of a solution of 4.2 g of meta-chloroperoxybenzoic acid in dichloromethane was slowly added dropwise. After completion of the dropwise addition, the mixture was stirred at room temperature for 2 hours and allowed to react. After completion of the reaction, 100 mL of a 10% sodium sulfite solution and 100 mL of dichloromethane were added. The organic layer was washed with water and then saturated saline, and the solvent was removed by evaporation. The concentrate was dissolved in 100 mL of tetrahydrofuran. Then 20 mL of a 10% sodium hydroxide solution was added, and the mixture was stirred at room temperature for 3 hours. After completion of the reaction, the mixture was neutralized with 10% hydrochloric acid, and 150 mL of ethyl acetate was added. The organic layer was washed with water and saturated saline, and the solvent was removed by evaporation to obtain 9 g of a compound represented by formula (18).

[Chem. 82]

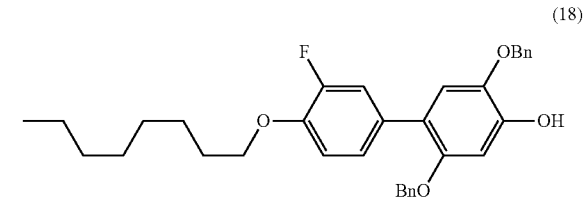

(18)

A reaction vessel equipped with a stirrer, a condenser, and a thermometer was charged with 9 g of compound (18), 3.5 g of potassium carbonate, 5.7 g of (2,2-dimethyl-1,3-dioxane-5-yl)methyl methanesulfonate, and 100 mL of N,N-dimethylformamide, and the mixture was allowed to react at 90° C. for 5 hours. After completion of the reaction, the reaction vessel was cooled, and 200 mL of ethyl acetate was added. The organic layer was washed with water and then saturated saline, and the solvent was removed by evaporation. Then the residue was dispersed in toluene to wash the residue and then purified on an alumina column to obtain 9.3 g of a compound represented by formula (19).

[Chem. 83]

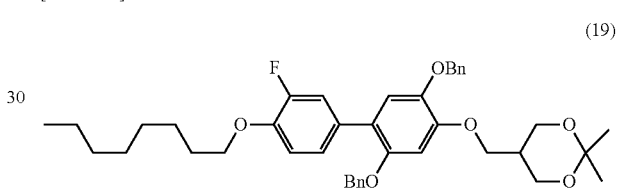

(19)

Then 9 g of compound (19), 50 mL of tetrahydrofuran, and 5 mL of ethanol were added, and the mixture was placed in an autoclave. Then 1 g of 5% palladium on carbon (wet) was added, and the mixture was subjected to catalytic hydrogen reduction at a hydrogen pressure of 0.5 kPa. After completion of the reaction, the palladium on carbon was removed by filtration, and the product was purified on an alumina column to obtain 6.2 g of a compound represented by formula (20).

[Chem. 84]

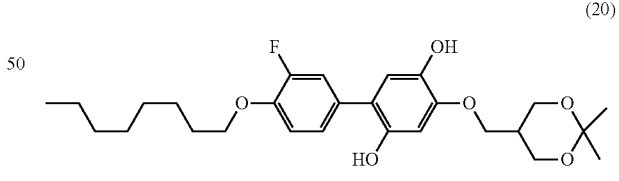

(20)

A reaction vessel equipped with a stirrer, a dropping funnel, and a thermometer was charged with 6.2 g of the above compound (20), 3.3 g of methacrylic acid, 50 mg of dimethylaminopyridine, and 30 mL of dichloromethane and cooled to 10° C. or lower. Then 4.5 g of diisopropylcarbodiimide was slowly added dropwise. After completion of the dropwise addition, the reaction vessel was returned to room temperature, and the mixture was allowed to react for 3 hours. After completion of the reaction, water was slowly added, and the mixture was washed with 50 mL of dichloromethane, water, and saturated saline. The solvent was removed by evaporation, and the residue was dissolved in 50 mL of tetrahydrofuran. 10 mL of 1N hydrochloric acid was added at room temperature, and the mixture was stirred for 3 hours. After completion of the reaction, 100 ml of ethyl acetate was added, and the mixture was washed with water and saturated saline. Then the solvent was removed by evaporation. The concentrate was purified on a silica gel column using dichloromethane/ethyl acetate to obtain 5.8 g of a target compound represented by (P-1-26).

[Chem. 85]

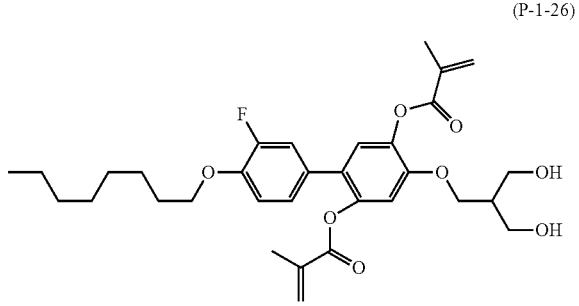

(P-1-26)

(Values of Physical Properties)
Melting point 42° C.
$^1$H-NMR (solvent: deuterated chloroform): δ: 0.88 (t, 3H), 1.28-1.31 (m, 8H), 1.34-1.38 (m, 4H) 1.49 (m, 1H), 1.83-1.86 (m, 6H), 1.97 (s, 6H), 2.63 (t, 2H), 2.72 (m, 1H), 3.77-3.89 (m, 4H), 4.05 (m, 2H), 4.20 (t, 2H), 4.38 (s, 2H), 5.60 (s, 1H), 6.14 (d, 2H), 6.95 (m, 2H), 7.20-7.27 (m, 1H), 7.82 (m, 1H)
$^{13}$C-NMR (solvent: deuterated chloroform): δ: 14.1, 17.3, 22.7, 25.9, 26.3, 27.9, 29.6, 30.6, 31.8, 37.1, 31.0, 31.1, 45.3, 62.5, 64.5, 68.7, 74.1, 114.0, 114.9, 125.3, 129.1, 129.7, 135.5, 136.0, 138.6, 158.3, 157.2, 166.0

Example 6

A reaction vessel equipped with a stirrer, a dropping funnel, and a thermometer was charged with 5 g of compound (P-1-26) in Example 5 and 50 mL of dichloromethane and cooled to 10° C. or lower. Next, 1.5 g of ethyl chloroformate was slowly added dropwise. After completion of the dropwise addition, the mixture was stirred for 30 minutes. Next, 1.1 g of triethylamine was added dropwise. After completion of the reaction, the organic layer was washed with water and then saturated saline, and the solvent was removed by evaporation. Then the residue was purified on a silica gel column to obtain 4.4 g of a target compound represented by compound (P-1-27).

[Chem. 86]

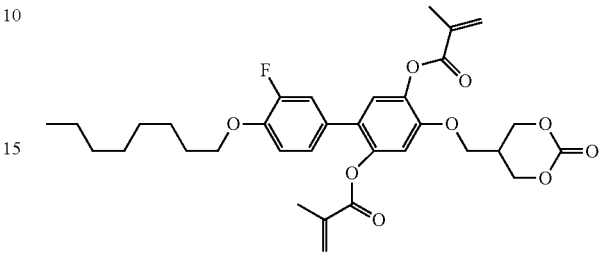

(P-1-27)

(Values of Physical Properties)
Melting point 118° C.
$^1$H-NMR (solvent: deuterated chloroform): δ: 0.88 (t, 3H), 1.28-1.34 (m, 10H), 1.80-1.85 (m, 2H), 1.94 (s, 3H), 2.07 (s, 3H), 2.67-2.70 (m, 1H), 4.01 (t, 2H), 4.10 (d, 2H), 4.34-4.39 (m, 2H), 4.49-4.53 (m, 2H), 5.68 (s, 1H), 5.81 (s, 1H), 6.19 (s, 1H), 6.37 (s, 1H), 6.81 (s, 1H), 6.95 (t, 1H), 7.11 (d, 1H), 7.13-7.15 (m, 2H)
$^{13}$C-NMR (solvent: deuterated chloroform): δ: 14.1, 17.9, 22.7, 25.9, 26.3, 27.9, 29.6, 30.6, 31.9, 68.7, 73.6, 75.4, 114.0, 122.3, 128.1, 133.3, 135.5, 139.4, 138.6, 146.7, 149.2, 151.7, 152.3, 157.2, 166.0

Example 7

A reaction vessel equipped with a stirrer, a dropping funnel, and a thermometer was charged with 10 g of compound (P-1-23) in Example 2, 3.2 g of triethylamine, and 100 mL of dichloromethane and cooled to 10° C. or lower. Next, 4.2 g of methyl malonyl chloride was slowly added dropwise. After completion of the dropwise addition, the mixture was stirred at room temperature for 2 hours. After completion of the reaction, the organic layer was washed with water and then saturated saline, and the solvent was removed by evaporation. Then the residue was purified on a silica gel column to obtain 8 g of a target compound represented as compound (P-1-28).

[Chem. 87]

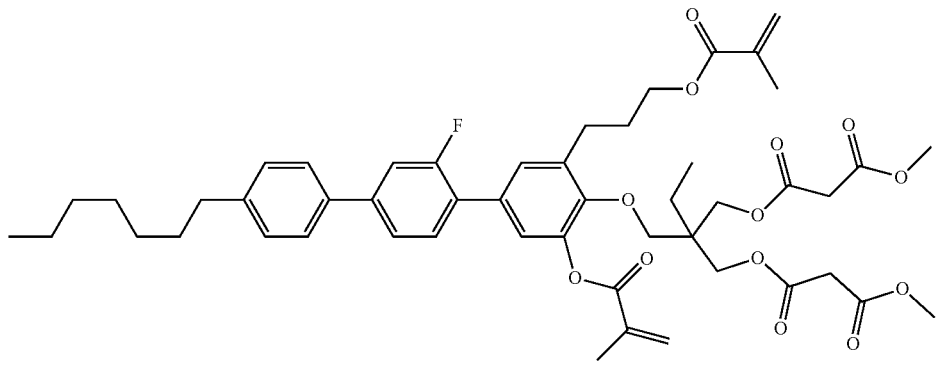

(P-1-28)

¹H-NMR (solvent: deuterated chloroform): δ: 0.83-0.88 (m, 6H), 1.27 (s, 8H), 1.63-1.69 (m, 4H), 1.91 (m, 2H), 1.97 (s, 6H), 2.63 (t, 6H), 3.21 (s, 4H), 3.80 (s, 2H), 3.94 (s, 4H), 4.11-4.20 (m, 2H), 5.60 (s, 1H), 6.14 (m, 3H), 7.02 (m, 1H), 7.28 (d, 2H), 7.38 (s, 1H), 7.61-7.64 (m, 3H), 7.65 (d, 1H), 7.94 (m, 1H)

¹³C-NMR (solvent: deuterated chloroform): δ: 14.1, 17.9, 22.7, 25.5, 26.3, 27.9, 29.3, 30.1, 31.2, 35.5, 36.4, 40.5, 51.5, 65.2, 70.7, 77.6, 122.7, 125.3, 127.1, 128.0, 129.7, 130.5, 135.0, 139.5, 152.5, 158.3, 166.0, 166.8

(Example 8) Preparation of Liquid Crystal Composition

A composition composed of the following compounds at the following mixing ratio:

[Chem. 88]

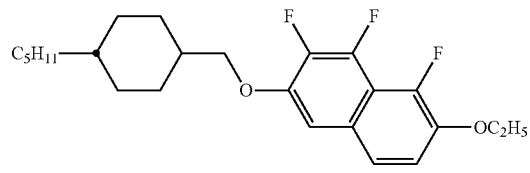

10%

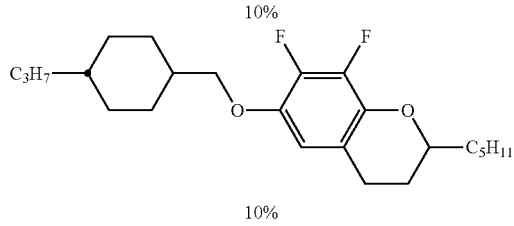

10%

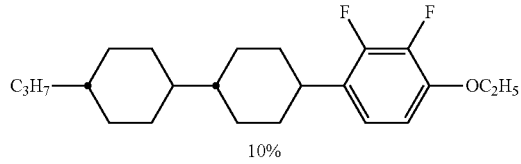

10%

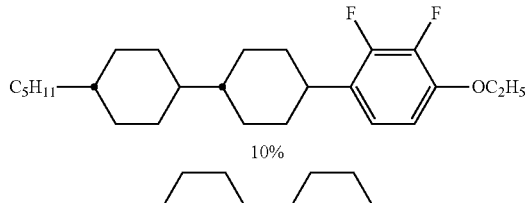

10%

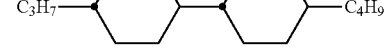

15%

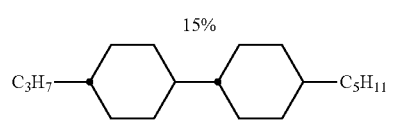

15%

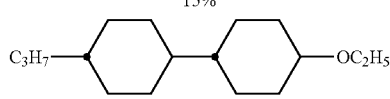

5%

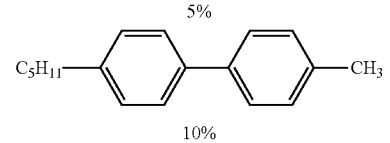

10%

-continued

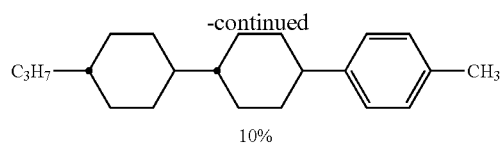

10%

0.3 Parts by mass the following polymerizable compound (P-2-8) was added to 100 parts by mass of the above liquid crystal composition LC-1, and the composition obtained was used as (LC-1).

[Chem. 89]

(P-2-8)

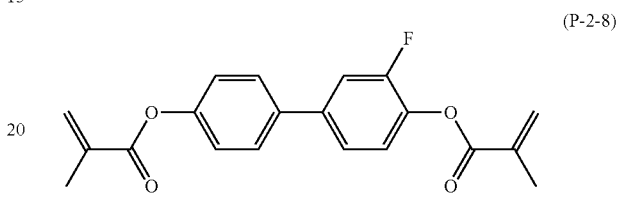

0.6 Parts by mass of compound (P-1-27) synthesized in Example 1 was added to 100 parts by mass of (LC-1) to prepare liquid crystal composition (LC-1M1).

Liquid crystal composition (LC-1M1) was subjected to the following evaluation tests.

(Evaluation Test for Vertical Alignment)

A first substrate (common electrode substrate) that includes a transparent electrode layer composed of a transparent common electrode and a color filter layer and includes no alignment film was produced, and a second substrate (pixel electrode substrate) that includes a pixel electrode layer having transparent pixel electrodes driven by active elements and includes no alignment film was produced. The liquid crystal composition was dropped onto the first substrate and sandwiched between the first and second substrates. A sealing material was cured under the conditions of normal pressure and 120° C. for 1 hour to obtain a liquid crystal cell having a cell gap of 3.2 μm. Then the liquid crystal cell was observed under a polarizing microscope to evaluate vertical alignment and alignment nonuniformity such as droplet stains using the following four ratings.

A: Vertical alignment was observed over the entire area including edges etc.

B: A very small number of alignment defects were found, but the level of the alignment defects was acceptable.

C: A large number of alignment defects were found even at edges etc., and the level of the alignment defects was not acceptable.

D: Alignment was very poor.

(Evaluation Test for Pretilt Angle Formation)

While an AC rectangular wave of 10 V and 100 Hz was applied to the liquid crystal cell used above (in the evaluation test for vertical alignment), a high-pressure mercury lamp was used to irradiate the cell with UV light with an illuminance of 100 m/cm² at 365 nm for 200 seconds. Then a physical external force was applied to the cell while an AC rectangular wave of 10 V and 100 Hz was applied. After the cell was left to stand for several minutes, the cell was observed under crossed Nicols, and the stability of white display was evaluated using the following four ratings.

A: Vertical alignment was observed over the entire area including edges etc.

B: A very small number of alignment defects were found, but the level of the alignment defects was acceptable.

C: A large number of alignment defects were found even at edges etc., and the level of the alignment defects was not acceptable.

D: Alignment was very poor.

(Storage Stability Test)

The cell was stored at room temperature (25° C.) and −15° C. for one week, and the presence of precipitation was visually checked.

The results of the evaluation test for vertical alignment showed uniform vertical alignment (level A). The results of the evaluation test for pretilt angle formation showed a very small number of defects (level B). The storage stability of the composition LC-1M1 was not problematic.

(Example 9) Preparation of Liquid Crystal Composition 0.6 Parts by mass of the compound represented as compound (P-1-23) synthesized in Example 2 was added to 100 parts by mass of liquid crystal composition (LC-1) to prepare liquid crystal composition (LC-1M2).

Liquid crystal composition (LC-1M2) was subjected to the same evaluation tests as those in Example 8. The results of the evaluation test for vertical alignment showed uniform vertical alignment (level A). The results of the evaluation test for pretilt angle formation showed uniform vertical alignment (level A). The storage stability of the composition LC-1M2 was not problematic.

(Example 10) Preparation of Liquid Crystal Composition 0.6 Parts by mass of the compound represented as compound (P-1-24) and synthesized in Example 3 was added to 100 parts by mass of liquid crystal composition (LC-1) to prepare liquid crystal composition (LC-1M3).

Liquid crystal composition (LC-1M3) was subjected to the same evaluation tests as those in Example 8. The results of the evaluation test for vertical alignment showed uniform vertical alignment (level A). The results of the evaluation test for pretilt angle formation showed uniform vertical alignment (level A). The storage stability of the composition LC-1M3 was not problematic.

(Example 11) Preparation of Liquid Crystal Composition 0.6 Parts by mass of the compound represented by compound (P-1-26) and synthesized in Example 5 was added to 100 parts by mass of liquid crystal composition (LC-1) to prepare liquid crystal composition (LC-1M4).

Liquid crystal composition (LC-1M4) was subjected to the same evaluation tests as those in Example 8. The results of the evaluation test for vertical alignment showed uniform vertical alignment (level B). The results of the evaluation test for pretilt angle formation showed uniform vertical alignment (level B). The storage stability of the composition LC-1M4 was not problematic.

Comparative Example 1

0.6 Parts by mass of a compound represented by formula (21) below was added to 100 parts by mass of liquid crystal composition (LC-1) to prepare liquid crystal composition (LC-1M5).

[Chem. 90]

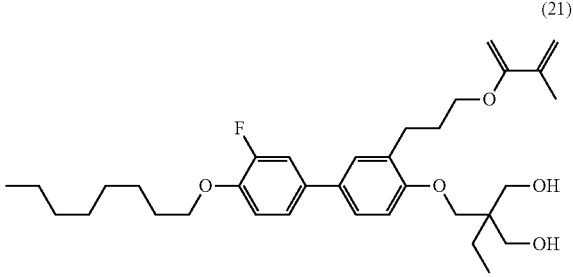

(21)

Liquid crystal composition (LC-1M5) was subjected to the same evaluation tests as those in Example 8. The results of the evaluation test for vertical alignment showed uniform vertical alignment (level B). The results of the evaluation test for pretilt angle formation showed defects, and the level of the defects was unacceptable (level C).

The storage stability of the composition LC-1M5 was not problematic.

Comparative Example 2

0.6 Parts by mass of a compound represented by formula (22) below was added to 100 parts by mass of liquid crystal composition (LC-1) to prepare liquid crystal composition (LC-1M6)

[Chem. 91]

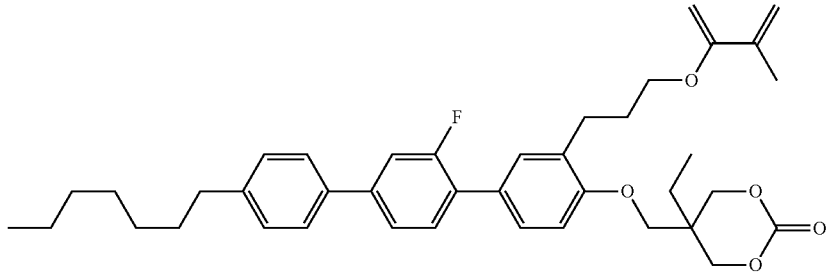

(22)

Liquid crystal composition (LC-1M6) was subjected to the same evaluation tests as those in Example 8. The results of the evaluation test for vertical alignment showed uniform vertical alignment (level B). The results of the evaluation test for pretilt angle formation showed defects, and the level of the defects was unacceptable (level C). The storage stability of the composition LC-1M6 was not problematic.

Comparative Example 3

0.6 Parts by mass of a compound represented by formula (23) below was added to 100 parts by mass of liquid crystal composition (LC-1) to prepare liquid crystal composition (LC-1M7). However, the prepared liquid crystal composition was precipitated at room temperature and could not be evaluated.

[Chem. 92]

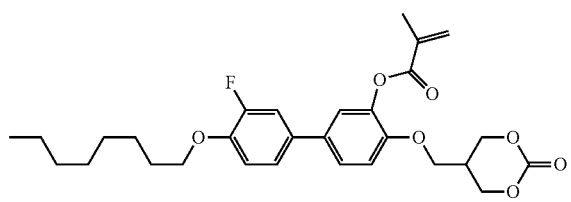

(23)

Comparative Example 4

0.6 Parts by mass of a compound represented by formula (24) below was added to 100 parts by mass of liquid crystal composition (LC-1) to prepare liquid crystal composition (LC-1M8).

[Chem. 93]

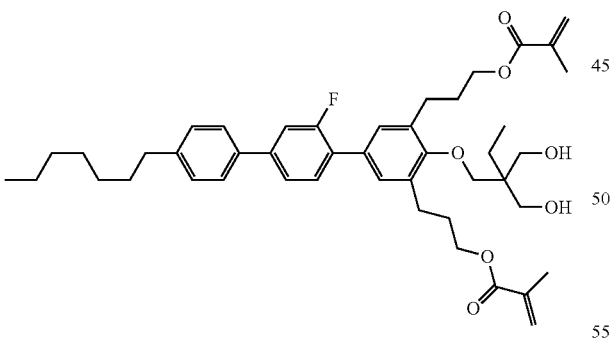

(24)

Liquid crystal composition (LC-1M8) was subjected to the same evaluation tests as those in Example 8. The results of the evaluation test for vertical alignment showed uniform vertical alignment (level A). The results of the evaluation test for pretilt angle formation showed defects, and the level of the defects was unacceptable (level C). The storage stability of the composition LC-1M8 was not problematic.

As described above, the compounds in the present invention can provide liquid crystal compositions having good alignment and pretilt angle stability and excellent in storage stability.

The invention claimed is:
1. A compound represented by general formula (i):

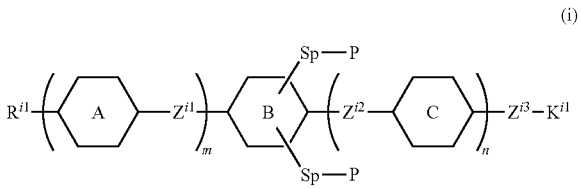

(i)

wherein
$R^{i1}$ represents a hydrogen atom, P-Sp-, a linear alkyl group having 1 to 30 carbon atoms, a branched alkyl group having 3 to 20 carbon atoms, a linear halogenated alkyl group having 1 to 30 carbon atoms, or a branched halogenated alkyl group having 3 to 20 carbon atoms, any —$CH_2$— group in the alkyl group or the halogenated alkyl group being optionally replaced by —CH═CH—, —C≡C—, —O—, —NH—, —COO—, —OCO—, or —OCOO—, provided that no —O— groups are adjacent to each other;
ring A and ring C each independently represent a divalent aromatic group, a divalent cyclic aliphatic group, a divalent heterocyclic compound group, a divalent condensed ring, or a divalent condensed polycyclic ring, any hydrogen atom in theses ring structures being optionally replaced by $L^{i1}$, $L^{i1}$ representing a halogen atom, a cyano group, a nitro group, P-Sp-, a monovalent organic group having a substituent represented by general formula $K^{i1}$, a linear alkyl group having 1 to 30 carbon atoms, or a linear halogenated alkyl group having 1 to 30 carbon atoms, any —$CH_2$— group in the alkyl group or the halogenated alkyl group being optionally replaced by —CH═CH—, —C≡C—, —O—, —NH—, —COO—, —OCO—, or —OCOO—, provided that no —O— groups are adjacent to each other;
ring B represents a phenylene group or a naphthylene group, ring B having at least two P-Sp- groups;
$Z^{i1}$ and $Z^{i2}$ each independently represent a single bond, —O—, —CH═CH—, —CF═CF—, —C≡C—, —COO—, —OCO—, —OCOO—, —OOCO—, —$CF_2$O—, —$OCF_2$—, —CH═CHCOO—, —OCOCH═CH—, —CH═C($CH_3$)COO—, —OCOC($CH_3$)═CH—, —$CH_2$—CH($CH_3$)COO—, —OCOCH($CH_3$)—$CH_2$—, —$OCH_2CH_2O$—, or an alkylene group having 1 to 10 carbon atoms, one —$CH_2$— group or two or more non-adjacent —$CH_2$— groups in the alkylene group being optionally replaced by —O—, —COO— or —OCO—;
$Z^{i3}$ represents a single bond, —O—, —CH═CH—, —COO—, —OCO—, —OCOO—, —OOCO—, —CH═CHCOO—, —OCOCH═CH—, —CH═C($CH_3$)COO—, —OCOC($CH_3$)═CH—, —$CH_2$—CH($CH_3$)COO—, —OCOCH($CH_3$)—$CH_2$—, or a linear alkylene group having 1 to 20 carbon atoms, one —$CH_2$— group or two or more non-adjacent —$CH_2$— groups in the alkylene group being optionally replaced by —O—, —COO—, or —OCO—; and $K^{i1}$ represents a group represented by any of general formulas (K-1) to (K-17):

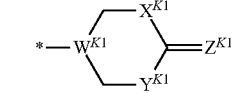 (K-1)

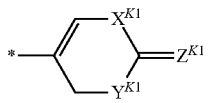 (K-2)

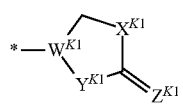 (K-3)

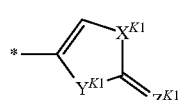 (K-4)

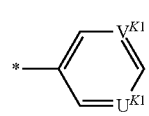 (K-5)

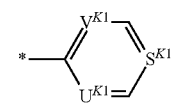 (K-6)

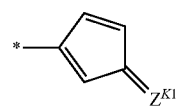 (K-7)

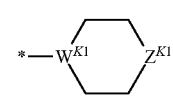 (K-8)

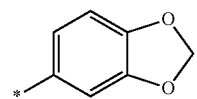 (K-9)

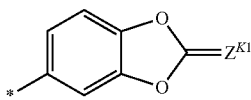 (K-10)

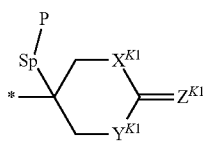 (K-11)

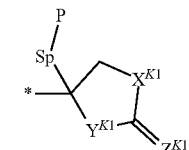 (K-12)

-continued

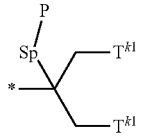 (K-13)

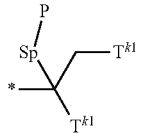 (K-14)

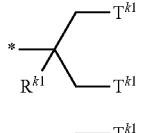 (K-15)

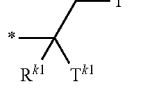 (K-16)

(K-17)

wherein $X^{K1}$ and $Y^{K1}$ each independently represent —CH$_2$—, an oxygen atom, or a sulfur atom; $Z^{K1}$ represents an oxygen atom or a sulfur atom; $W^{K1}$, $U^{K1}$, $V^{K1}$, and $S^{K1}$ each independently represent a methine group or a nitrogen atom; $R^{K1}$ represents a hydrogen atom or a linear alkyl group having 1 to 6 carbon atoms; and $T^{K1}$ each independently represent a group represented by any of general formulas (T-1) to (T-6):

—OH (T-1)

—COOH (T-2)

 (T-3)

—SH (T-4)

—NH$_2$ (T-5)

(T-6)

wherein $S^{T1}$ represents a single bond, a linear alkylene group having 1 to 15 carbon atoms, or a linear alkenylene group having 2 to 18 carbon atoms, any —CH$_2$— group in the alkylene group or the alkelene group being optionally replaced by —O—, —COO—, —C(=O)—, —C(=CH$_2$)—, or —OCO—, provided that no oxygen atoms are directly adjacent to each other; $R^{T1}$ represents an alkyl group having 1 to 5 carbon atoms, any —CH$_2$— group in the alkyl group being optionally replaced by —O—, —COO—, —C(=O)—, —C(=CH$_2$)—, or —OCO—, provided that no oxygen atoms are directly adjacent to each other; and $R^{T2}$ and $R^{T3}$ each independently represent a hydrogen atom or an alkyl group having 1 to 5 carbon atoms, and wherein a plurality of P each represent a polymerizable group; a plurality of Sp each represent a spacer group or a single bond; m represents an integer of 1 to 4; n represents 0 or 1; P are each independently the same or different; S are each independently the same or different; when a plurality of A, C, $Z^1$, $Z^2$, and $K^{i1}$ are present, they are each independently the same or different; and, when $K^{i1}$ represents any of general formulas (K-15), (K-16), and (K-17) and each $T^{k1}$ represents any of (T-1), (T-4), and (T-5), at least one Sp represents a single bond.

2. The compound according to claim 1, wherein A and C in general formula (i) each represent a ring structure selected from a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a 1,2,3,4-tetrahydronaphthalene-2,6-diyl group, and a 1,3-dioxane-2,5-diyl group, the ring structure being unsubstituted or representing a group optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or P-Sp-.

3. The compound according to claim 1, wherein each P in general formula (i) represents a substituent selected from the group consisting of substituents represented by general formula (P-1) to general formula (P-14) below:

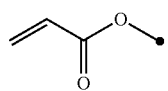
(P-1)

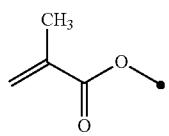
(P-2)

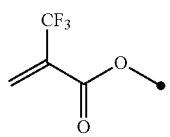
(P-3)

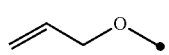
(P-4)

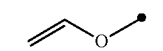
(P-5)

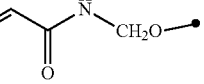
(P-6)

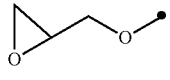
(P-7)

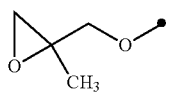
(P-8)

-continued

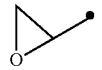
(P-9)

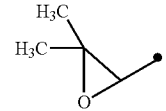
(P-10)

(P-11)

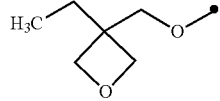
(P-12)

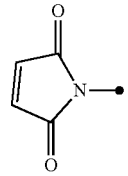
(P-13)

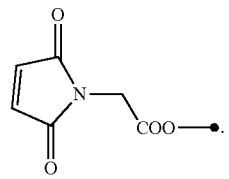
(P-14)

4. The compound according to claim 1, wherein $K^{i1}$ in general formula (i) represents general formula (K-1), (K-3), (K-11), or (K-13).

5. A liquid crystal composition comprising: the compound according to claim 1, the compound being represented by general formula (i); a polymerizable compound different from the compound represented by general formula (i); and a non-polymerizable liquid crystal compound.

6. The liquid crystal composition according to claim 5, wherein the liquid crystal composition contains, as the polymerizable compound, one or two or more compounds represented by general formula (P):

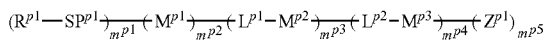
(P)

wherein $Z^{p1}$ represents a fluorine atom, a cyano group, a hydrogen atom, an alkyl group which has 1 to 15 carbon atoms and in which any hydrogen atom is optionally replaced by a halogen atom, an alkoxy group which has 1 to 15 carbon atoms and in which any hydrogen atom is optionally replaced by a halogen atom, an alkenyl group which has 1 to 15 carbon atoms and in which any hydrogen atom is optionally replaced by a halogen atom, an alkenyloxy group which has 1 to 15 carbon atoms and in which any hydrogen atom is optionally replaced by a halogen atom, or -$Sp^{p2}$-$R^{p2}$;

$R^{p1}$ and $R^{p2}$ each independently represent any of the following formula (R-I) to formula (R-VIII):

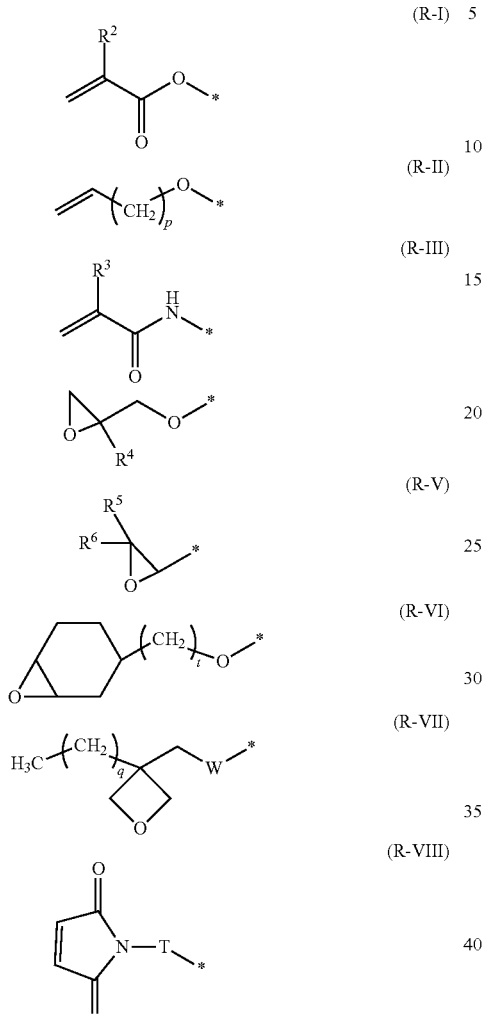

wherein
* represents a bond to $Sp^{p1}$;
$R^2$ to $R^6$ each independently represent a hydrogen atom, an alkyl group having 1 to 5 carbon atoms, or a halogenated alkyl group having 1 to 5 carbon atoms;
W represents a single bond, —O—, or a methylene group;
T represents a single bond or —COO—; and
p, t, and q each independently represent 0, 1, or 2);
$Sp^{p1}$ and $Sp^{p2}$ each represent a spacer group;
$L^{p1}$ and $L^{p2}$ each independently represent a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^a$—, —NR$^a$—CO—, —SCH$_2$—CH$_2$S—, —CH=CR$^a$—COO—, —CH=CR$^a$—OCO—, —COO—CR$^a$=CH—, —OCO—CR$^a$=CH—, —COO—CR$^a$=CH— COO—, —COO—CR$^a$=CH—OCO—, —OCO— CR$^a$=CH—COO—, —OCO—CR$^a$=CH— OCO—, —(CH$_2$)$_z$—C(=O)—O—, —(CH$_2$)$_z$—O— (C=O)—, —O—(C=O)—(CH$_2$)$_z$—, —(C=O)— O—(CH$_2$)$_z$—, —CH$_2$(CH$_3$)C—C(=O)—O—, —CH$_2$(CH$_3$)C—O—(C=O)—, —O—(C=O)—C (CH$_3$)—CH$_2$, —(C=O)—O—C(CH$_3$)—CH$_2$, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C—, wherein R$^a$ each independently represent a hydrogen atom or an alkyl group having 1 to 4 carbon atoms, and z represents an integer of 1 to 4;
$M^{p2}$ represents a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a 1,2,3,4-tetrahydronaphthalene-2,6-diyl group, a 1,3-dioxane-2,5-diyl group, or a single bond, $M^{p2}$ being unsubstituted or optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —R$^{p1}$;
$M^{p1}$ represents any of the following formulas (i-11) to (ix-11):

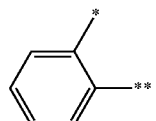
(i-11)

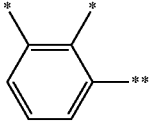
(iv-11)

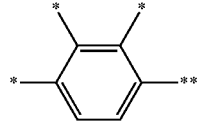
(vii-11)

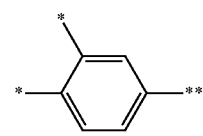
(ii-11)

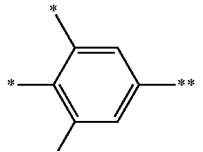
(v-11)

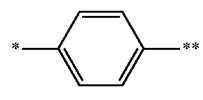
(viii-11)

(iii-11)

(vi-11)
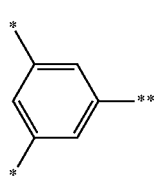

(ix-11)
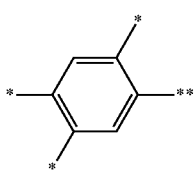

wherein * represents a bond to $Sp^{p1}$, and ** represents a bond to $L^{p1}$, $L^{p2}$, or $Z^{p1}$;

$M^{p3}$ represents any of the following formulas (i-13) to (ix-13):

(i-13)
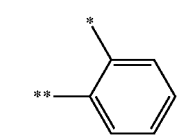

(iv-13)
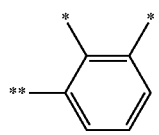

(vii-13)
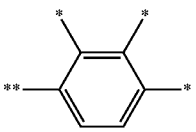

(ii-13)
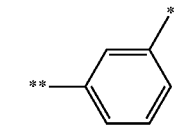

(v-13)
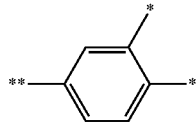

(viii-13)
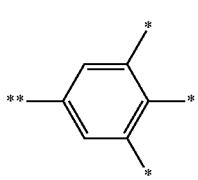

(iii-13)
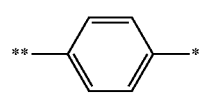

(vi-13)
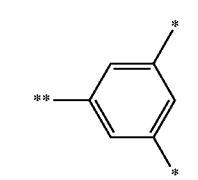

(ix-13)
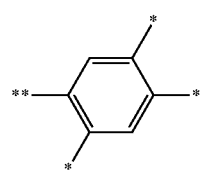

wherein * represents a bond to $Z^{p1}$, and ** represents a bond to $L^{p2}$;

$m^{p2}$ to $m^{p4}$ each independently represent 0, 1, 2, or 3;

$m^{p1}$ and $m^{p5}$ each independently represent 1, 2, or 3;

when a plurality of $Z^{p1}$ are present, they are each independently the same or different; when a plurality of $R^{p1}$ are present, they are each independently the same or different; when a plurality of $R^{p2}$ are present, they are each independently the same or different; when a plurality of $Sp^{p1}$ are present, they are each independently the same or different; when a plurality of $Sp^{p2}$ are present, they are each independently the same or different; when a plurality of $L^{p1}$ are present, they are each independently the same or different; and when a plurality of $M^{p2}$ are present, they are each independently the same or different.

7. A liquid crystal display device comprising two substrates each using the liquid crystal composition according to claim 5, wherein at least one of the two substrates includes no alignment film.

* * * * *